US007094398B1

(12) United States Patent
Lieber et al.

(10) Patent No.: US 7,094,398 B1
(45) Date of Patent: Aug. 22, 2006

(54) RECOMBINANT ADENOVIRAL VECTORS EXPRESSING CHIMERIC FIBER PROTEINS FOR CELL SPECIFIC INFECTION AND GENOME INTEGRATION

(75) Inventors: André Lieber, Seattle, WA (US); Dmitry M Shayakhmetov, Seattle, WA (US); Denise R Farrer, Seattle, WA (US); Thalia Papayannopoulou, Seattle, WA (US); George Stamatoyannopoulos, Seatte, WA (US)

(73) Assignee: University of Washington, Seattle, WA (US)

( * ) Notice: Subject to any disclaimer, the term of this patent is extended or adjusted under 35 U.S.C. 154(b) by 16 days.

(21) Appl. No.: 09/980,564

(22) PCT Filed: Jun. 1, 2000

(86) PCT No.: PCT/US00/15442

§ 371 (c)(1),
(2), (4) Date: Nov. 30, 2001

(87) PCT Pub. No.: WO00/73478

PCT Pub. Date: Dec. 7, 2000

Related U.S. Application Data

(60) Provisional application No. 60/137,213, filed on Jun. 1, 1999, provisional application No. 60/161,097, filed on Oct. 22, 1999.

(51) Int. Cl.
| | |
|---|---|
| *A01N 63/00* | (2006.01) |
| *C12N 15/00* | (2006.01) |
| *C12N 15/63* | (2006.01) |
| *C12N 15/86* | (2006.01) |
| *C12P 21/06* | (2006.01) |

(52) U.S. Cl. ............... 424/93.2; 424/93.21; 435/320.1; 435/69.1; 435/455; 435/456; 536/23.2; 536/24.1
(58) Field of Classification Search ............... 424/93.2; 435/235.1, 69, 320.1, 456; 536/23.2, 24.1
See application file for complete search history.

(56) References Cited

U.S. PATENT DOCUMENTS 5,856,152 A * 1/1999 Wilson et al. ............... 435/457

FOREIGN PATENT DOCUMENTS

| WO | WO94/06920 | 3/1994 |
|---|---|---|
| WO | WO97/38723 | 10/1997 |
| WO | WO98/54346 | 12/1998 |
| WO | WO 00/70071 | 11/2000 |

OTHER PUBLICATIONS

Davison et al, Genetic content and evolution of adenoviruses, Journal of General Virology, 2003, vol. 84, pp. 2895-2908.*

Chow and Broker, The spliced structures of adenovirus 2 fiber message and the other late mRNAs, Cell, Oct. 1978, vol. 15(2), pp. 497-510.*

Alexander, Ian E. et al., "DNA-Damaging Agents Greatly Increase the Transduction of Nondividing Cells by Adeno-Associated Virus Vectors," *Journal of Virology*, 68:8282-7, 1994 (Exhibit 5).

Alexander, Ian E. et al., "Effects of Gamma Irradiation on the Transduction of Dividing and Nondividing Cells in Brain and Muscle of Rats by Adeno-Associated Virus Vectors," *Human Gene Therapy*, 7:841-50, 1996 (Exhibit 6).

Antoniou, Michael et al., "Efficient 3'-end formation of human β-globin mRNA *in vivo* requires sequences with the last intron but occurs independently of the splicing reaction," *Nucleic Acids Research*, 26:721-9, 1998 (Exhibit 7).

Balagué, Cristina et al., "Adeno-Associated Virus Rep78 Protein and Terminal Repeats Enhance Integration of DNA Sequences into the Cellular Genome," *Journal of Virology*, 71:3299-306, 1997 (Exhibit 8).

Balagué, Cristina et al., "Sustained high-level expression of a full-length human factor VIII and restoration of clotting activity in hemophilic mice using a minimal adenovirus vector," *Blood*, 95:820-8, 2000 (Exhibit 9).

Bhatia, Mickie et al., "A newly discovered class of human hematopoeitic cells with SCID-repopulating activity," *Nature Medicine*, 4:1038-45, 1998 (Exhibit 10).

Becker, Pamela S. et al., "Adhesion receptor expression by hematopoietic cell lines and murine progenitors: Modulation by cytokines and cell cycle status," *Experimental Hematology*, 27:533-41, 1999 (Exhibit 11).

Bergelson, Jeffrey M. et al., "Isolation of a Common Receptor for Coxsackie B Viruses and Adenoviruses 2 and 5," *Science*, 275:1320-3, 1997 (Exhibit 12).

Berns, Kenneth I., "*Pavoviridae*: The Viruses and Their Replication," *Fields Virology*, 3rd Edition, B.N. Fields et al. (eds.), Lippincott-Raven Publishers, PA, 2:2173-97, 1996 (Exhibit 13).

Blau, C. Anthony et al., "Fetal Hemoglobin in Acute and Chronic States of Erythroid Expansion," *Blood*, 81:227-33, 1993 (Exhibit 14).

Boyer, Julie et al., "Adenovirus E4 34k and E4 11k Inhibit Double Strand Break Repair and Ar Physically Associated with the Cellular DNA-Dependent Protein Kinase," *Virology*, 263:307-12, 1999 (Exhibit 15).

Bregni, M. et al., "Adenovirus vectors for gene transduction into mobilized blood CD34+ cells," *Gene Therapy*, 5:465-72, 1998 (Exhibit 16).

(Continued)

*Primary Examiner*—Dave Trong Nguyen
(74) *Attorney, Agent, or Firm*—Townsend and Townsend and Crew LLP

(57) ABSTRACT

The present invention provides for novel chimeric Ad-vectors carrying transgene, or portions of transgenes for stable and efficient gene transfer into diverse cell types or tissues in a CAR- and/or $\alpha_v\beta_{3/5}$-independent manner. Also provided are methods for producing such vectors and the use thereof for gene therapy to target a specific cell type or tissue.

25 Claims, 34 Drawing Sheets

OTHER PUBLICATIONS

Burcin, Mark M. et al. "Adenovirus-mediated regulable target gene expression *in vivo*," *Proc Natl Acad Sci USA*, 96:355-60, 1999 (Exhibit 17).

Byk, Tamara et al., "Lipofectamine and Related Cationic Lipids Strongly Improve Adenoviral Infection Efficiency of Primitive Human Hematopoietic Cells," *Human Gene Therapy*, 9:2493-502, 1998 (Exhibit 18).

Cantwell, Mark J. et al., "Adenovirus Vector Infection of Chronic Lymphocytic Leukemia B Cells," *Blood*, 88:4676-83, 1996 (Exhibit 19).

Case, Scott S. et al., "Stable transduction of quiescent $CD34^{+}CD38^{-}$ human hematopoietic cells by HIV-1-based lentiviral vectors," *Proc Natl Acad Sci USA*, 96:2988-93, 1999 (Exhibit 20).

Cerami, Carla et al., "The Basolateral Domain of the Hepatocyte Plasma Membrane Bears Receptors for the Circumsporozoite Protein of *Plamsodium falciparum* Sporozoites," *Cell*, 70:1021-33, 1992 (Exhibit 21).

Challberg, Sharon S. and Gary Ketner, "Deletion Mutants of Adenovirus 2: Isolation and Initial Characterization of Virus Carrying Mutations Near the Right End of the Viral Genome," *Virology*, 114:196-209, 1981 (Exhibit 22).

Chartier, C. et al., "Efficient Generation of Recombinant Adenovirus Vectors by Homologous Recombination in *Escherichia coli,"* *Journal of Virology*, 70:4805-10, 1996 (Exhibit 23).

Chatterjee, Shyama et al., "A Conserved Peptide Sequence of the *Plasmodium falciparum* Circumsporozoite Protein and Anitpeptide Antibodies Inhibit *Plasmodium berghei* Sporozoite Invasion of Hep-G2 Cells and Protect Immunized Mice against *P. berghei* Sporozoite Challenge," *Infection and Immunity*, 63:4375-81, 1995 (Exhibit 24).

Chen, Hsiaoli et al., "Analysis of enhancer function of the HS-40 core sequence of the human α-globin cluster," *Nucleic Acids Research*, 25:2917-22, 1997 (Exhibit 25).

Chillon, Miguel et al., "Group D Adenoviruses Infect Primary Central Nervous System Cells More Efficiently than Those from Group C," *Journal of Virology*, 73:2537-40, 1999 (Exhibit 26).

Chroboczek, J. et al., "Adenovirus Fiber," *Current Topics in Microbiology and Immunology*, W. Doerfler and P. Böhm (eds.), Springer, 1:163-200, 1995 (Exhibit 27).

Chung, Jay H. et al., "Characterization of the chicken β-globin insulator," *Proc Natl Acad Sci USA*, 94:575-80, 1997 (Exhibit 28).

Crompton, Janet et al., "Expression of a foreign epitope on the surface of the adenovirus hexon," *The Journal of General Virology*, 75:133-9, 1994 (Exhibit 29).

Dao, Mo A. et al., "Engraftment and Retroviral Marking of $CD34^{+}$ and $CD34^{+}CD38^{-}$ Human Hematopoietic Progenitors Assessed in Immune-Deficient Mice," *Blood*, 91:1243-55, 1998 (Exhibit 30).

Davison, A. J. et al., "The DNA Sequence of Adenovirus Type 40," *Journal of Molecular Biology*, 234:1308-16, 1993 (Exhibit 31).

Dayhoff, M. O. et al., "A Model of Evolutionary Change in Proteins," *Atlas of Protein Sequence and Structure*, Supplement 3, 5:345-52, 1978 (Exhibit 32).

Defer, Christine et al., "Human Adenovirus-Host Cell Interactions: Comparative Study with Members of Subgroups B and C," *Journal of Virology*, 64:3661-73, 1990 (Exhibit 33).

Doi, N. and H. Yanagawa, "Screening of comformationally constrained random polypeptide libraries displayed on a protein scaffold," *Cellular and Molecular Life Sciences*, 54:394-404, 1998 (Exhibit 34).

Dunaway, Marietta et al., "The Activity of the scs and scs' Insulator Elements Is Not Dependent on Chromosomal Context", *Molecular and Cellular Biology*, 17:182-9, 1997 (Exhibit 35).

Ellerby, H. Michael et al., "Anti-cancer activity of targeted pro-apoptotic peptides," *Nature Medicine*, 5:1032-8, 1999 (Exhibit 36).

Ellis, James et al., "A dominant chromatin-opening activity in 5' hypersensitive site 3 of the human β-globin locus control region," *The EMBO Journal*, 15:562-8, 1996 (Exhibit 37).

Ellis, James et al., "Evaluation of β-globin gene therapy constructs in single copy transgenic mice," *Nucleic Acid Research*, 25:1296-302, 1997 (Exhibit 38).

Emery, David W. et al., "Analysis of γ-Globin Expression Cassettes in Retrovirus Vectors," *Human Gene Therapy*, 10:877-888, 1999 (Exhibit 39).

Everitt, E. and E. Rodríguez, "Adenovirus cellular receptor site recirculation of HeLa cells upon receptor-mediated endocytosis is not low pH-dependent," *Archives of Virology*, 144:787-95, 1999 (Exhibit 40).

Felsenfeld, Gary et al., "Chromatin structure and gene expression," *Proc Natl Acad Sci USA*, 93:9384-8, 1996 (Exhibit 41).

Fiering, Steven N. et al., "Improved FACS-Gal: Flow Cytometric Analysis and Sorting of Viable Eukaryotic Cells Expressing Reporter Gene Constructs," *Cytometry*, 12:291-301, 1991 (Exhibit 42).

Floch, Virginie, et al., "Cationic Phosphonolipids as non Viral Vectors for DNA Transfection in Hematopoietic Cell Lines and $CD34^{+}$ Cells," *Blood Cells, Molecules & Diseases*, 23:69-87, 1997 (Exhibit 43).

Flomenberg, Phyllis R. et al., "Molecular Epidemiology of Adenovirus Type 35 Infections in Immunocompromised Hosts," *The Journal of Infectious Diseases*, 155:1127-34, 1987 (Exhibit 44).

Flomenberg, Phyllis et al., "Increasing Incidence of Adenovirus Disease in Bone Marrow Transplant Recipients," *The Journal of Infectious Diseases*, 169:775-81, 1994 (Exhibit 45).

Forrester, William C. et al., "A developmentally stable chromatin structure in the human β-globin gene cluster," *Proc Natl Acad Sci USA*, 83:1359-63, 1986 (Exhibit 46).

Fraser, Peter and Frank Grosveld, "Locus control regions, chromatin activation and transcription," *Current Opinion in Cell Biology*, 10:361-5, 1998 (Exhibit 47).

Gall, Jason et al., "Adenovirus Type 5 and 7 Capsid Chimera: Fiber Replacement Alters Receptor Tropism without Affecting Primary Immune Neutralization Epitopes," *Journal of Virology*, 70:2116-23, 1996 (Exhibit 48).

Gonzales, R. et al., "Increased gene transfer in acute myeloid leukemic cells by an adenovirus vector containing a modified fiber protein," *Gene Therapy*, 6:314-20, 1999 (Exhibit 49).

Goddell, Margaret A. et al., " Dye efflux studies suggest that hematopoietic stem cells expressing low or undetectable levels of CD34 antigen exist in multiple species," *Nature Medicine*, 3:1337-45, 1997 (Exhibit 50).

Grosveld, Frank et al., "The Dynamics of Globin Gene Expression and Gene Therapy Vectors," *Seminars in Hematology*, 35:105-111, 1998 (Exhibit 51).

Gruber, William C. et al., "Fiber Gene and Genomic Origin of Human Adenovirus Type 4," *Virology*, 196:603-611, 1993( Exhibit 52).

Heffelfinger, Sue C. et al., "SK HEP-1: A Human Cell Line of Endothelial Origin," *In vitro Cellular and Developmental Biology*, 28A:136-42, 1992 (Exhibit 53).

Hitt, Mary M. et al., "Human Adenovirus Vectors for Gene Transfer into Mammalian Cells," *Advances in Pharmacology*, J. Thomas August (ed.), Academic Press, 40:137-206, 1997 (Exhibit 54).

Horwitz, Marshall S., "Adenoviruses," *Fields Virology*, 3rd Edition, B.N. Fields et al. (eds.), Lippincott-Raven Publishers, PA, 2:2149-71, 1996 (Exhibit 55).

Hsu, Kuo-Hom Lee et al., "A Monoclonal Antibody Specific for the Cellular Receptor for the Group B Coxsackieviruses," *Journal of Virology*, 62:1647-52, 1988 (Exhibit 56).

Huang, Shuang et al., "Upregulation of Integrins αvβ3 and αvβ5 on Human Monocytes and T Lymphocytes Facilitates Adenovirus-Mediated Gene Delivery," *Journal of Virology*, 69:2257-63, 1995 (Exhibit 57).

Huang, Shuang et al., "Adenovirus Interaction with Distinct Integrins Mediates Separate Events in Cell Entry and Gene Delivery to Hermatopoietic Cells," *Journal of Virology*, 70:4502-8 1996 (Exhibit 58).

Ikuta, Koichi and Irving L. Weissman, "Evidence that hematopoietic stem cells express mouse c-*kit* but do not depend on steel factor for their generation," *Proc Natl Acad Sci USA*, 89:1502-6, 1992 (Exhibit 59).

Kay, Mark A. et al., " Therapeutic Serum Concentrations of Human Alpha-1-Antitrypsin After Adenoviral-Mediated Gene Transfer Into Mouse Hepatocytes," *Hepatology*, 21:815-9, 1995 (Exhibit 60).

Kirby, Ian et al., "Identification of Contact Residues and Definition of the CAR-Binding Site of Adenovirus Type 5 Fiber Protein," *Journal of Virology*, 74:2804-3, 2000 (Exhibit 61).

Klehr, Degmar et al., "Scaffold-Attached Regions from the Human Interferon β Domain Can B Used To Enhance the Stable Expression of Genes under the Control of Various Promoters," *Biochemistry*, 30:1264-70, 1991 (Exhibit 62).

Koivunen, Erkki et al., "Phage Libraries Displaying Cyclic Peptides with Different Ring Sizes: Ligand Specificities of the RGD-Directed Integrins," *Bio/Technology*, 13:265-70, 1995 (Exhibit 63).

Koivunen, Erkki et al., "Tumor targeting with a selective gelatinase inhibitor," *Nature Biotechnology*, 17:768-74, 1999 (Exhibit 64).

Krasnykh, Victor N. et al., "Generation of Recombinant Adenovirus Vectors with Modified Fibers for Altering Viral Tropism," *Journal of Virology*, 70:6839-46, 1996 (Exhibit 65).

Krasnykh, Victor et al., "Characterization of an Adenovirus Vector Containing a Heterologous Peptide Epitope in the HI Loop of the Fiber Knob," *Journal of Virology*, 72:1844-52, 1998 (Exhibit 66).

Krause, Diane S. et al., "Regulation of CD34 expression in differentiating M1 cells," *Experimental Hematology*, 25:1051- 61, 1997 (Exhibit 67).

Kwoh, T. Jesse et al., "Introduction and expression of the bacterial *PaeR7* methylase gene in mammalian cells," *Proc Natl Acad Sci USA*, 83:7713-7, 1986 (Exhibit 68).

Langer, Stephen J. and Jerome Schaack, "293 Cell Lines That Inducibly Express High Levels of Adenovirus Type 5 Precursor Terminal Protein," *Virology*, 221:172-9, 1996 (Exhibit 69).

Legrand, V. et al., "Fiberless Recombinant Adenoviruses: Virus Maturation and Infectivity in the Absence of Fiber," *Journal of Virology*, 73:907-19, 1999 (Exhibit 70).

Li, Qiliang et al., "Development of Viral Vectors for Gene Therapy of β-Chain Hemoglobinopathies: Optimization of a γ-Globin Gene Expression Cassette," *Blood*, 93:2208-16, 1999 (Exhibit 71).

Lieber, André et al., "Adenovirus-Mediated Transfer of the Amphotropic Retrovirus Receptor cDNA Increases Retroviral Transduction in Cultured Cells;" *Human Gene Therapy*, 6:5-11, 1995 (Exhibit 72).

Lieber, André and Mark A. Kay, "Adenovirus-Mediated Expression of Ribozymes in Mice," *Journal of Virology*, 70:3153-8, 1996 (Exhibit 73).

Lieber, André et al., "Elimination of Hepatitis C Virus RNA in Infected Human Hepatocytes by Adenovirus-Mediated Expression of Ribozymes," *Journal of Virology*, 70:8782-91, 1996 (Exhibit 74).

Lieber, André et al., "Recombinant Adenoviruses with Large Deletions Generated by Cre-Mediat d Excision Exhibit Different Biological Properties Compared with First-Generation Vectors in Vitro and In Vivo," *Journal of Virology*, 70:8944-60, 1996 (Exhibit 75).

Lieber, André et al., "The Role of Kupffer Cell Activation and Viral Gene Expression in Early Liver Toxicity after Infusion of Recombinant Adenovirus Vectors," *Journal of Virology*, 71:8798-807, 1997 (Exhibit 76).

Lieber, André et al., "Inhibition of NF-κB Activation in Combination with Bcl-2 Expression Allows for Persistence of First-Generation Adenovirus Vectors in the Mouse Liver," *Journal of Virology*, 72:9267-77, 1998 (Exhibit 77).

Lieber, André et al., "Integrating Adenovirus—Adeno-Associated Virus Hybrid Vectors Devoid of All Viral Genes," *Journal of Virology*, 73:9314-24, 1999 (Exhibit 78).

Lietner, Agnes et al., "Lack of DNA synthesis among CD34+ cells in cord blood and in cytokine-mobilized blood," *British Journal of Haematology*, 92:255-62, 1996 (Exhibit 79).

Lyu, Yi Lisa et al., "Inversion/Dimerization of Plasmids Mediated by Inverted Repeats," *Journal of Molecular Biology*, 285:1485-501, 1999 (Exhibit 80).

Maizel, Jacob V., Jr. et al., "The Polypeptides of Adenovirus—Evidence of Multiple Protein Components in the Virion and a Comparison of Types 2, 7A, and 12," *Virology*, 36:115-25, 1968 (Exhibit 81).

Malik, Punam et al., "Recombinant Adeno-Associated Virus Mediates a High Level of Gene Transfer but Less Efficient Integration in the K562 Human Hematopoietic Cell Line," *Journal of Virology*, 71:1776-83, 1997 (Exhibit 82).

Martin, David I. K. et al., "Regulation of β-globin gene expression: straightening out the locus," *Current Opinion in Genetics & Development*, 6:488-95, 1996 (Exhibit 83).

Mathias, P. et al., "Multiple Adenovirus Serotypes Use αv-Integrins for Infection," *Journal of Virology*, 68:6811-4, 1994 (Exhibit 84).

Matsunaga, Takuya et al., "Thrombopoietin Promotes the Survival of Murine Hematopoietic Long-Term Reconstituting Cells: Comparison With the Effects of FLT3/FLK-2 Ligand and Interleukin-6," *Blood*, 92:452-61, 1998 (Exhibit 85).

May, Gillian and Tariq Enver, "Targeting gene expression to haemopoietic stem cells: a chromatin-dependent upstream element mediates cell type-specific expression of the stem cell antigen CD34," *The EMBO Journal*, 14:564-74, 1995 (Exhibit 86).

McGuckin, Colin P. et al., "A novel approach to investigating the erythroid lineage, using both receptor analysis and haemoglobin detection," *British Journal of Haematology*, 95:457-60, 1996 (Exhibit 87).

Michael, S. I. et al., "Addition of a short peptide ligand to the adenovirus fiber protein," *Gene Therapy*, 2:660-8, 1995 (Exhibit 88).

Mitani, Kohnoske et al., "Transduction of Human Bone Marrow by Adenoviral Vector," *Human Gene Therapy*, 5:941-8, 1994 (Exhibit 89).

Mittereder, Nanette et al., "Evaluation of the Concentration and Bioactivity of Adenovirus Vectors for Gene Therapy," *Journal of Virology*, 70:7498-509, 1996 (Exhibit 90).

Miyazawa, Naoki et al., "Fiber Swap between Adenovirus Subgroups B and C Alters Intracellular Trafficking of Adenovirus Gene Transfer Vectors," *Journal of Virology*, 73:6056-65, 1999 (Exhibit 91).

Mizuguchi, Hiroyuki and Mark A. Kay, "Efficient Construction of a Recombinant Adenovirus Vector by an Improved *In Vitro* Ligation Method," *Human Gene Therapy*, 9:2577-83, 1998 (Exhibit 92).

Mohler, William A. and Helen M. Blau, "Gene expression and cell fusion analyzed by *lacZ* complementation in mammalian cells," *Proc Natl Acad Sci USA*, 93:12423-7, 1996 (Exhibit 93).

Moore, Kateri A. et al., "In Vitro Maintenance of Highly Purified, Transplantable Hematopoietic Stem Cells," *Blood*, 89:4337-47, 1997 (Exhibit 94).

Neering, Sarah J. et al., "Transduction of Primitive Human Hematopoietic Cells With Recombinant Adenovirus Vectors," *Blood*, 88:1147-55, 1996 (Exhibit 95).

Nelson, James E. and Mark A. Kay, "Persistence of Recombinant Adenovirus In Vivo Is Not Dependent on Vector DNA Replication," *Journal of Virology*, 71:8902-7, 1997 (Exhibit 96).

Neu, Stefan et al., "Isolation and Phenotypic Characterization of CD117-Positive Cells," *Leukemia Research*, 20:963-71, 1996 (Exhibit 97).

Nicolás, Andrea L. et al., "Creation and Repair of Specific DNA Double-Strand Breaks *in Vivo* Following Infection with Adenovirus Vectors Expressing *Saccharomyces cerevisiae* HO Endonuclease," *Virology*, 266:211-24, 2000 (Exhibit 98).

Osawa, Masatake et al., "Long-Term Lymphohematopoietic Reconstitution by a Single CD34-Low/Negative Hematopoietic Stem Cell," *Science*, 273:242-5, 1996 (Exhibition 99).

Papayannopoulou, Thalia et al., "Insights into the cellular mechanisms of erythropoietin-thrombopoietin synergy," *Experimental Hematology*, 24:660-9, 1996 (Exhibit 100).

Papayannopoulou, T. and C. Craddock, "Homing and Trafficking of Hemopoietic Progenitor Cells," *Acta Haematologica*, 97:97-104 1997 (Exhibit 101).

Pasqualini, Renate and Erkki Ruoslahti, "Organ targeting *in vivo* using phage display peptide libraries," *Nature*, 380:364-6, 1996 (Exhibit 102).

Pring-Åkerblom, Patricia et al., "Molecular Characterization of Hemagglutination Domains on the Fibers of Subgenus D Adenoviruses," *Journal of Virology*, 72:2297-304, 1998 (Exhibit 103).

Qing, Keyun et al., "Adeno-Associated Virus Type 2-Mediated Gene Transfer: Correlation of Tyrosine Phosphorylation of the Cellular Single-Stranded D Sequence-Binding Protein with Transgene Expression in Human Cells In Vitro and Murine Tissues In Vivo," *Journal of Virology*, 72:1593-9, 1998 (Exhibit 104).

Recchia, Alessandra et al., "Site-specific integration mediated by a hybrid adenovirus/adeno-associated virus vector," *Proc Natl Acad Sci USA*, 96:2615-20 1999 (Exhibit 105).

Roberts, Andrew W. and Donald Metcalf, "Noncycling State of Peripheral Blood Progenitor Cells Mobilized by Granulocyte Colony-Stimulating Factor and Other Cytokines," *Blood*, 86:1600-5, 1995 (Exhibit 106).

Roelvink, Peter W. et al., "Comparative Analysis of Adenovirus Fiber-Cell Interaction: Adenovirus Type 2 (Ad2) and Ad9 Utilize the Same Cellular Fiber Receptor but Use Different Binding Strategies for Attachment," *Journal of Virology*, 70:7614-21, 1996 (Exhibit 107).

Roelvink, Peter W. et al., "The Coxsackievirus-Adenovirus Receptor Protein Can Function as a Cellular Attachment Protein for Adenovirus Serotypes from Subgroups A, C, D, E, and F," *Journal of Virology*, 72:7909-15, 1998 (Exhibit 108).

Rouet, Philippe et al., "Expression of a site-specific endonuclease stimulates homologous recombination in mammalian cells," *Proc Natl Acad Sci USA*, 91:6064-8, 1994 (Exhibit 109).

Roy, Vivek and Catherine M. Verfaillie, "Expression and function of cell adhesion molecules on fetal liver, cord blood and bone marrow hematopoietic progenitors: Implications for anatomical localization and developmental stage specific regulation of hematopoiesis," *Experimental Hematology*, 27:302-12, 1999 (Exhibit 110).

Russell, David W. et al., "Adeno-associated virus vectors preferentially transduce cells in S phase," *Proc Natl Acad Sci USA*, 91:8915-9, 1994 (Exhibit 111).

Russell, David W. et al., "DNA synthesis and topoisomerase inhibitors increase transduction by adeno-associated virus vectors," *Proc Natl Acad Sci USA*, 92:5719-23, 1995 (Exhibit 112).

Rutledge, Elizabeth A. and David W. Russell, "Adeno-Associated Virus Vector Integration Junctions," *Journal of Virology*, 71:8429-36, 1997 (Exhibit 113).

Samulski, Richard Jude et al., "Helper-Free Stocks of Recombinant Adeno-Associated Viruses: Normal Integration Does Not Require Viral Gene Expression," *Journal of Virology*, 63:3822-8 1989 (Exhibit 114).

Sánchez, Mariá-José et al., "Characterization of the First Definitive Hematopoietic Stem Cells in the AGM and Liver of the Mouse Embryo," *Immunity*, 5:513-25, 1996 (Exhibit 115).

Schiedner, Gudrun et al., "Genomic DNA transfer with a high-capacity adenovirus vector results in improved *in vivo* gene expression and decreased toxicity," *Nature Genetics*, 18:180-3, 1998 (Exhibit 116).

Shakibaei, Mehdi and Ute Frevert, "Dual Interaction of the Malaria Circumsporozoite Protein with the Low Density Lipoprotein Receptor-related Protein (LRP) and Heparan Sulfate Proteoglycans," *The Journal of Experimental Medicine*, 184:1699-711, 1996 (Exhibit 117).

Shenk, Thomas, "*Adenoviridae*: The Viruses and Their Replication," *Fields Virology*, 3rd Edition, B.N. Fields et al. (eds.), Lippincott-Raven Publishers, PA, 2:2111-48, 1996 (Exhibit 118).

Shields, Anthony F. et al., "Adenovirus Infections in Patients Undergoing Bone-Marrow Transplantation," *The New England Journal of Medicine*, 312:529-33, 1985 (Exhibit 119).

Shtrichman, Ronit and Tamar Kleinberger, "Adenovirus Type 5 E4 Open Reading Frame 4 Protein Induces Apoptosis in Transformed Cells," *Journal of Virology*, 72:2975-82, 1998 (Exhibit 120).

Simmons, Paul J. et al., "*c-kit* is expressed by primitive human hematopoietic cells that give rise to colony-forming cells in stroma-dependent for cytokine-supplemented culture," *Experimental Hematology*, 22:157-65, 1994 (Exhibit 121).

Steinwaerder, Dirk S. et al., "Generation of Adenovirus Vectors Devoid of All Viral Genes by Recombination between Inverted Repeats," *Journal of Virology*, 73:9303-13, 1999 (Exhibit 122).

Stevenson, Susan C. et al., "Human Adenovirus Serotypes 3 and 5 Bind to Two Different Cellular Receptors via the Fiber Head Domain," *Journal of Virology*, 69:2850-7, 1995 (Exhibit 123).

Stevenson, Susan C. et al., "Selective Targeting of Human Cells by a Chimeric Adenovirus Vector Containing a Modified Fiber Protein," *Journal of Virology*, 71:4782-90, 1997 (Exhibit 124).

Tiemessen, Caroline T. and Alistair H. Kidd, "The subgroup F adenoviruses," *The Journal of General Virology*, 76:481-97, 1995 (Exhibit 125).

Tollefson, Ann E. et al., "The Adenovirus Death Protein (E3-11.6K) Is Required at Very Late Stages of Infection for Efficient Cell Lysis and Release of Adenovirus from Infected Cells," *Journal of Virology*, 70:2296-306, 1996 (Exhibit 126).

Tomko, Richard P. et al., "HCAR and MCAR: The human and mouse cellular receptors for subgroup C adenoviruses and group B coxsackieviruses," *Proc Natl Acad Sci USA*, 94:3352-6, 1997 (Exhibit 127).

Van der Vliet, P. C., "Adenovirus DNA Replication," *Current Topics in Microbiology and Immunology*, W. Doerfler and P. Böhm (eds.), Springer, 2:1-30, 1995 (Exhibit 128).

Watanabe, Tsutomu et al., "Gene Transfer Into Human Bone Marrow Hematopoietic Cells Mediated by Adenovirus Vectors," *Blood*, 87:5032-9, 1996 (Exhibit 129).

Wickham, Thomas J. et al., "Integrins $\alpha v \beta 3$ and $\alpha v \beta 5$ Promote Adenovirus Internalization but Not Virus Attachment," *Cell*, 73:309-19, 1993 (Exhibit 130).

Wickham, T. J. et al., "Targeting of adenovirus penton base to new receptors through replacement of its RGD motif with other receptor-specific peptide motifs," *Gene Therapy*, 2:750-6, 1995 (Exhibit 131).

Wickham, Thomas J. et al., "Targeted Adenovirus Gene Transfer to Endothelial and Smooth Muscle Cells by Using Bispecific Antibodies," *Journal of Virology*, 70:6831-8, 1996 (Exhibit 132).

Wickham, Thomas J. et al., "Adenovirus targeted to heparan-containing receptors increases its gene delivery efficiency to multiple cell types," *Nature Biotechnology*, 14:1570-3, 1996 (Exhibit 133).

Xiao, Xiao et al., "A Novel 165-Base-Pair Terminal Repeat Sequence Is the Sole *cis* Requirement for the Adeno-Associated Virus Life Cycle," *Journal of Virology*, 71:941-8, 1997 (Exhibit 134).

Yamaguchia, Yuji et al., "Functional characterization of the promoter for the gene encoding murine CD34," *Biochimica et Biophysica Acta*, 1350:141-6, 1997 (Exhibit 135).

Yang, C. C. et al., "Cellular Recombination Pathways and Viral Terminal Repeat Hairpin Structures Are Sufficient for Adeno-Associated Virus Integration In Vivo and In Vitro," *Journal of Virology*, 71:9231-47, 1997 (Exhibit 136).

Yang, Yiping et al., "Cellular immunity to viral antigens limits E1-deleted adenoviruses for gene therapy," *Proc Natl Acad Sci USA*, 91:4407-11, 1994 (Exhibit 137).

Zanjani, Esmail D. et al., "Human bone marrow CD34⁻ cells engraft in vivo and undergo multilineage expression that includes giving rise to CD34⁺ cells," *Experimental Hematology*, 26:353-60, 1998 (Exhibit 138).

* cited by examiner

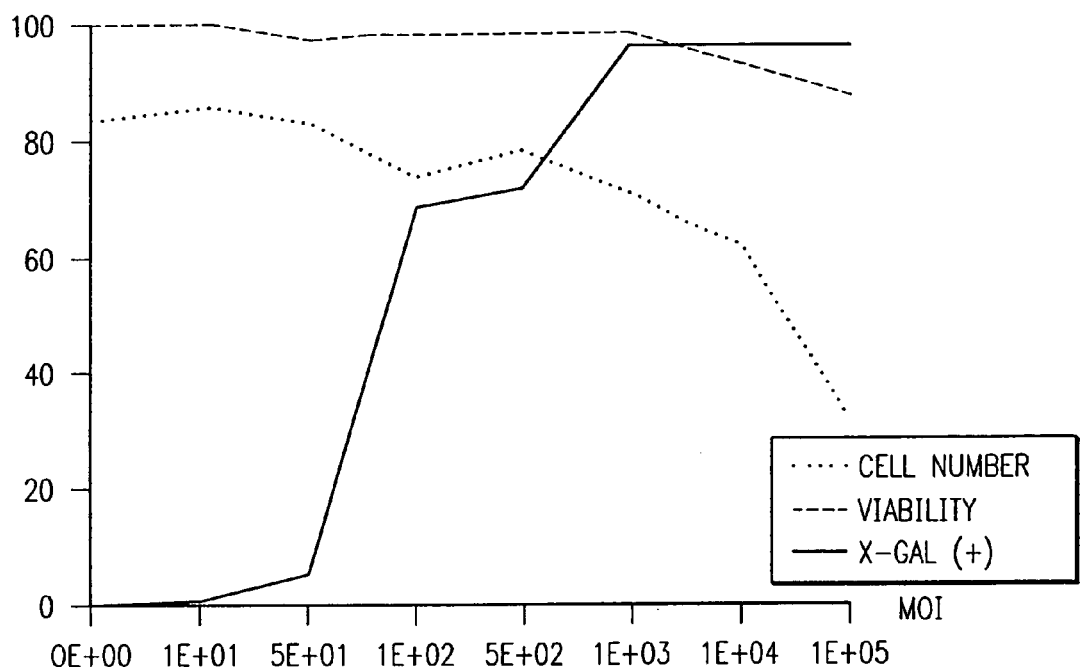
FIG. 4A  K562
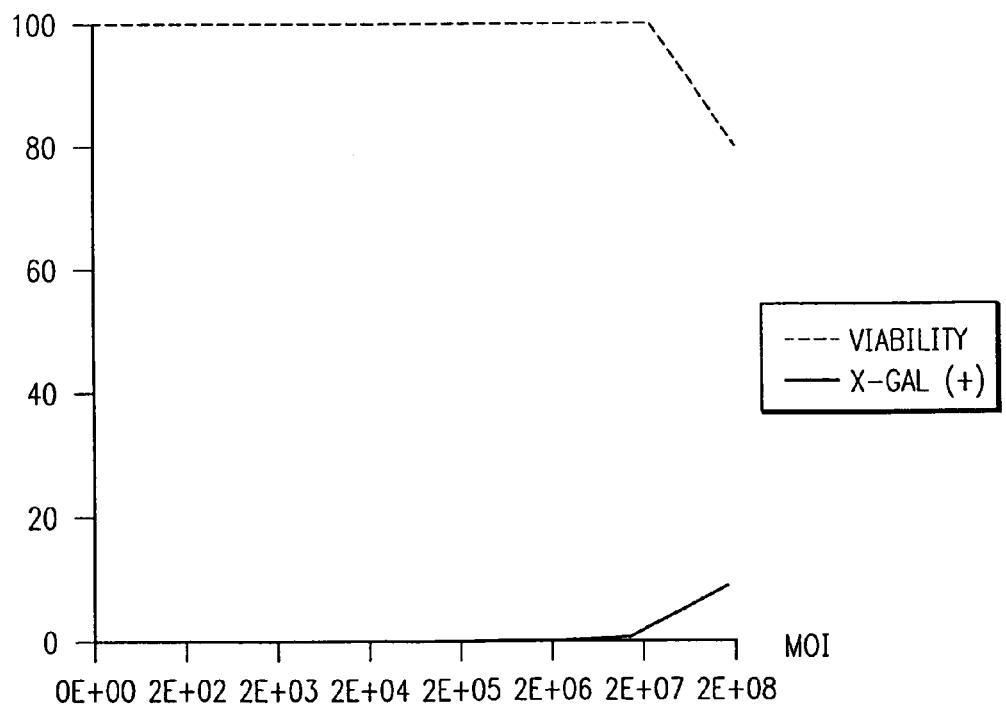
FIG. 4B  CD34+

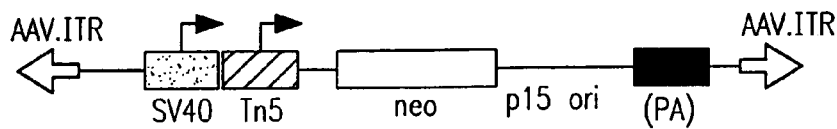
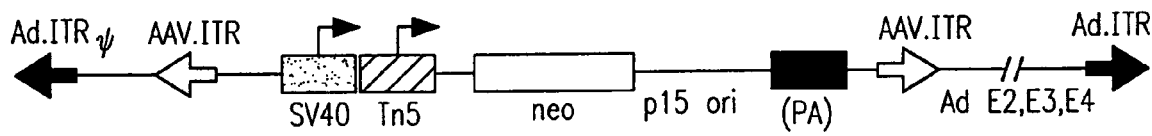
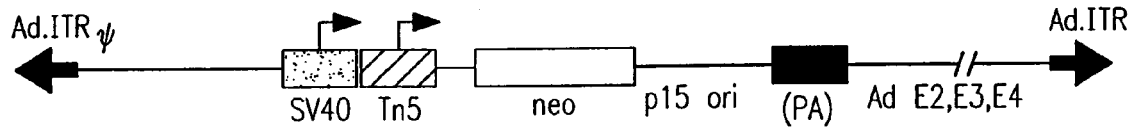
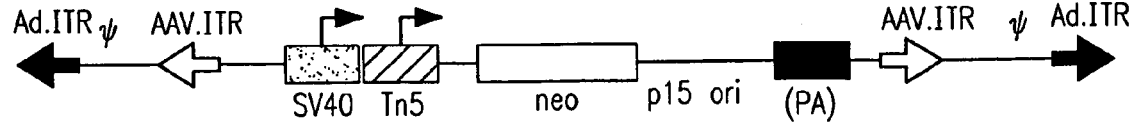
FIG. 8A

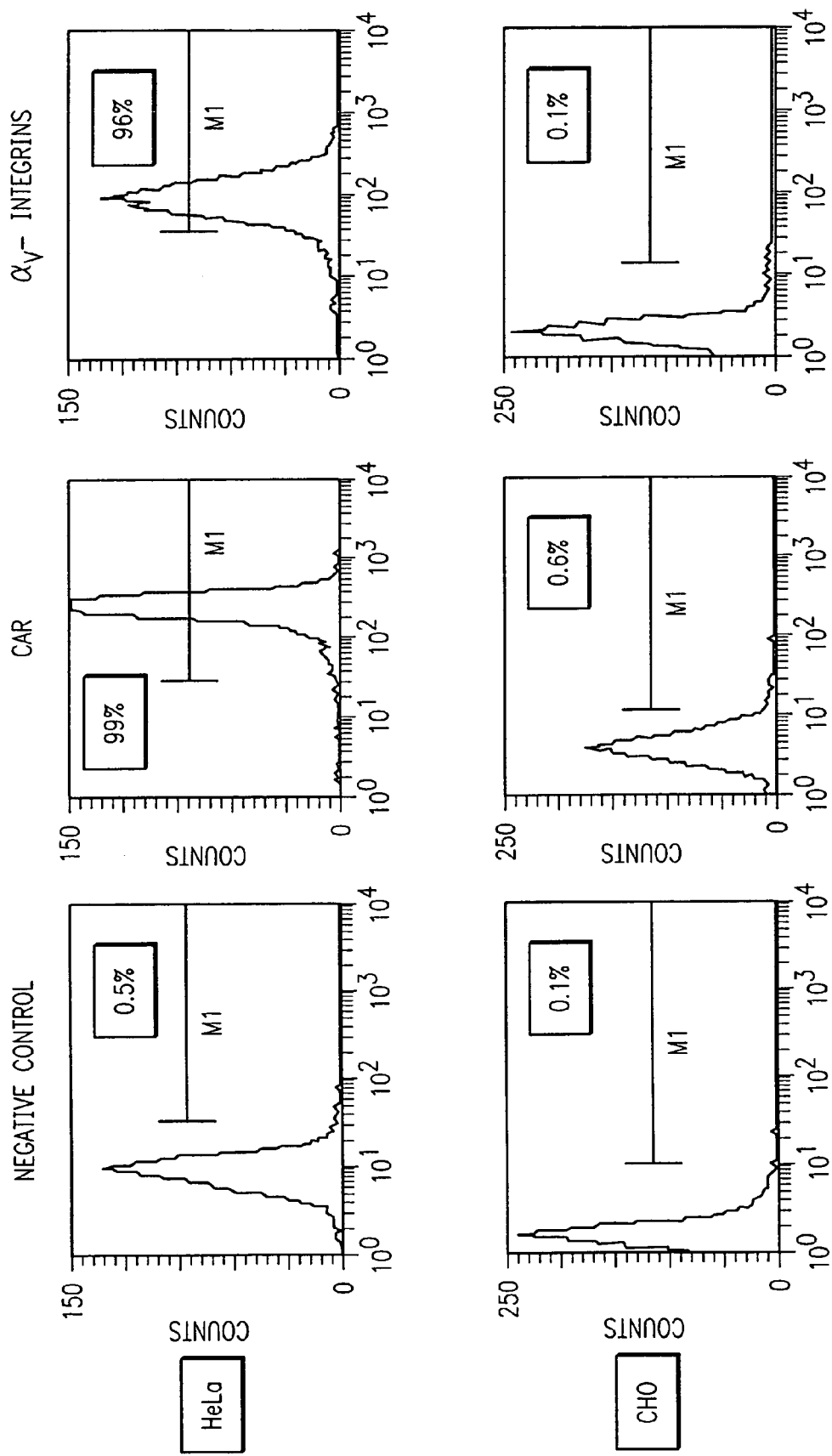
FIG. 10-i

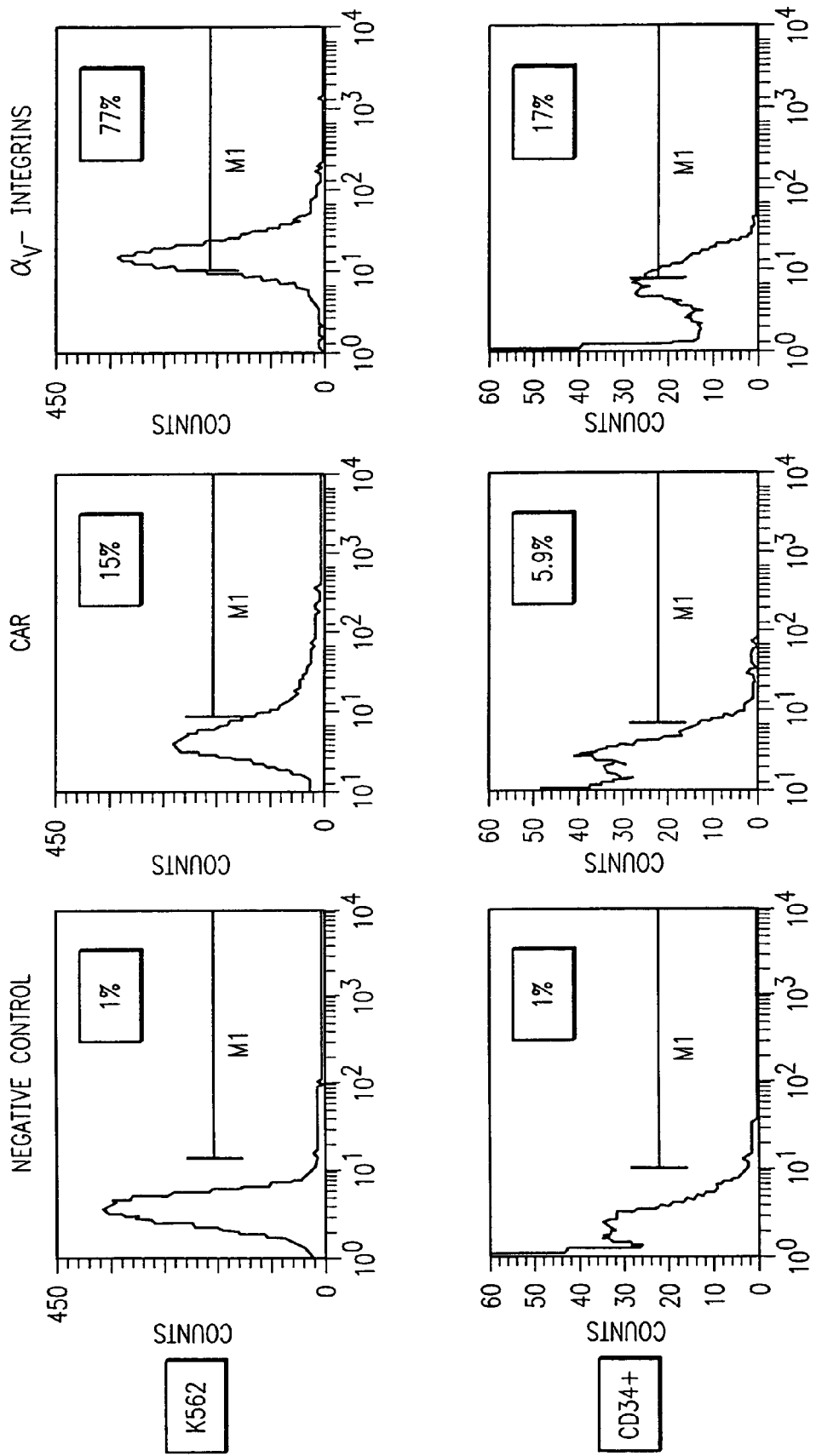
FIG. 10-ii

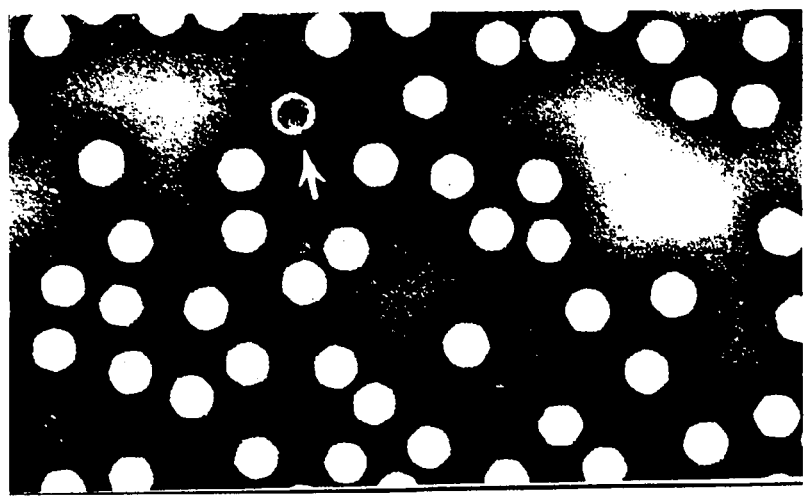
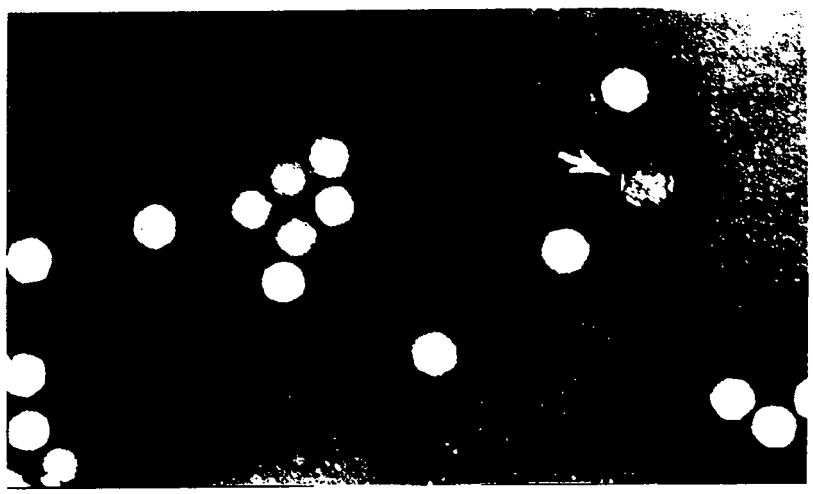
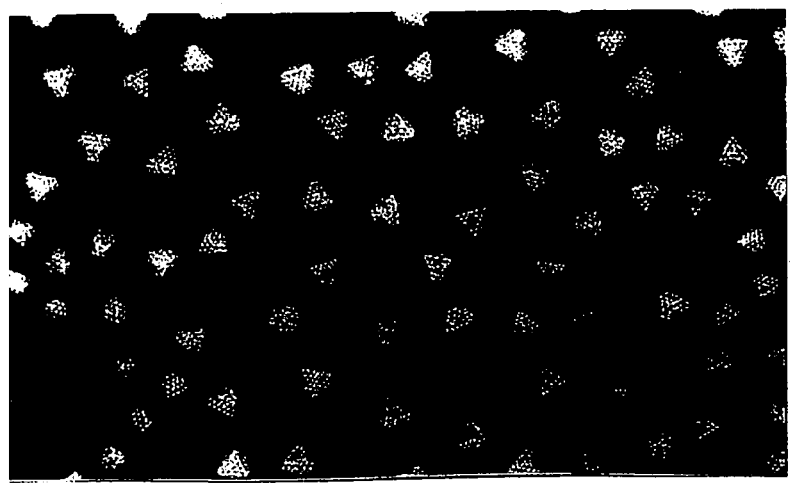
FIG. 11

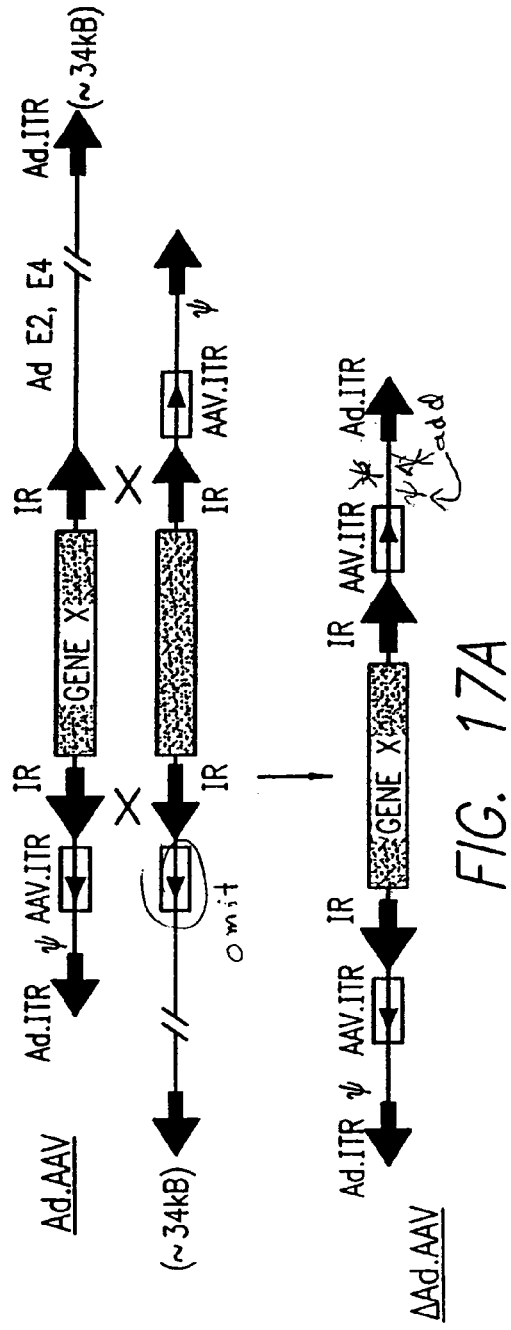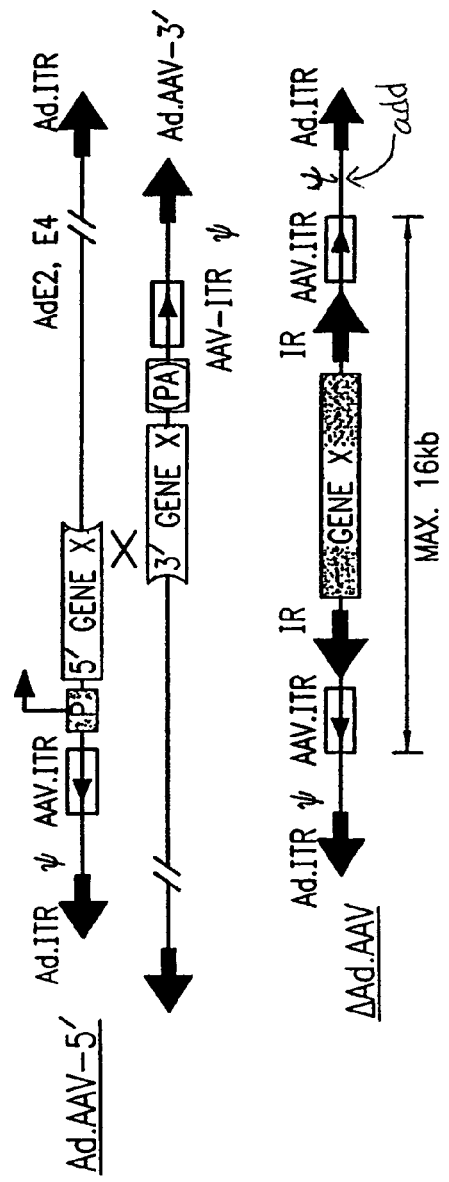

STRUCTURE AND FEATURES OF CHIMERIC ADENOVIRUS VECTORS.

| Adeno vector | Ad 5L | Ad 5S | Ad 5/9L | Ad 5/9S | Ad 5/35L | Ad 5/35S |
|---|---|---|---|---|---|---|
| Binding to CAR | YES | YES | YES | YES | NO | NO |
| genome/PFU ratio | 13 | 143 | 29 | 582 | 17 | 14 |
| Attachment to/internalization into | | | | | | |
| 293 | +++ | ++ | ++ | +/− | +++ | +++ |
| K562 | −/+ | −/+ | −/+ | −− | +++ | +++ |
| Y79 | ++ | + | + | +/− | + | + |
| Gene transfer efficiency | | | | | | |
| 293 | +++ | ++ | ++ | +/− | +++ | +++ |
| K562 | −/+ | −/+ | −/+ | −− | +++ | +++ |
| Y79 | ++ | + | + | +/− | + | + |

FIG. 25

SEQUENCE LISTING

<160> NUMBER OF SEQ ID NOS: 18

<210> SEQ ID NO 1
<211> LENGTH: 27
<212> TYPE: DNA
<213> ORGANISM: Homo sapiens

<400> SEQUENCE: 1
ggcgttactt aagctagagc ttatctg                27

<210> SEQ ID NO 2
<211> LENGTH: 26
<212> TYPE: DNA
<213> ORGANISM: Homo sapiens
<300> PUBLICATION INFORMATION:
<301> AUTHORS: Andre Lieber
<303> JOURNAL: Virology
<304> VOLUME: 73
<306> PAGES: 9314-24
<307> DATE: 1999

<400> SEQUENCE: 2
ctctctagtt ctagcctcga tctcac                26

<210> SEQ ID NO 3
<211> LENGTH: 30
<212> TYPE: DNA
<213> ORGANISM: Human Ad5

<400> SEQUENCE: 3
gcccaagaat aaagaatcgt ttgtgttatg             30

<210> SEQ ID NO 4
<211> LENGTH: 31
<212> TYPE: DNA
<213> ORGANISM: Human Ad5

<400> SEQUENCE: 4

```
agctggtcta gaatggtggt ggatggcgcc a                              31

<210> SEQ ID NO 5
<211> LENGTH: 54
<212> TYPE: DNA
<213> ORGANISM: Human Chimeric Ad5/9

<400> SEQUENCE: 5
aatgggtttc aagagagtcc ccctggagtc ctgtcactca aactagctga ccca     54

<210> SEQ ID NO 6
<211> LENGTH: 57
<212> TYPE: DNA
<213> ORGANISM: Human Chimeric Ad5/9

<400> SEQUENCE: 6
cataacacaa acgattcttt attcttgggc ttcattcttg ggcgatatag gaaaagg  57

<210> SEQ ID NO 7
<211> LENGTH: 54
<212> TYPE: DNA
<213> ORGANISM: Human Chimeric Ad5/35

<400> SEQUENCE: 7
aatgggtttc aagagagtcc ccctggagtt cttactttaa aatgtttaac ccca     54

<210> SEQ ID NO 8
<211> LENGTH: 59
<212> TYPE: DNA
<213> ORGANISM: Human Chimeric Ad5/35

<400> SEQUENCE: 8
cataacacaa acgattcttt attcttgggc attttagttg tcgtcttctg taatgtaag  59

<210> SEQ ID NO 9
<211> LENGTH: 27
<212> TYPE: DNA
<213> ORGANISM: Human Ad5

<400> SEQUENCE: 9
cgcgatatcg attggatcca ttaacta                                   27

<210> SEQ ID NO 10
<211> LENGTH: 25
<212> TYPE: DNA
<213> ORGANISM: Human Ad5

<400> SEQUENCE: 10 caggggact ctcttgaaac ccatt                                      25

<210> SEQ ID NO 11
<211> LENGTH: 7
<212> TYPE: PRT
<213> ORGANISM: Artificial
<220> FEATURE:
<223> OTHER INFORMATION: FLAG peptide

<400> SEQUENCE: 11

Asp Tyr Asp Asp Asp Asp Lys
1               5

<210> SEQ ID NO 12
<211> LENGTH: 6
<212> TYPE: PRT
```

```
<213> ORGANISM: Plasmodium falciparum
<300> PUBLICATION INFORMATION:
<301> AUTHORS: C. Cerami
<303> JOURNAL: Cell
<304> VOLUME: 70
<306> PAGES: 1021-33
<307> DATE: 1992
<300> PUBLICATION INFORMATION:
<301> AUTHORS: S. Chatterjee
<303> JOURNAL: Infection and Immunity
<304> VOLUME: 63
<306> PAGES: 4375-81
<307> DATE: 1995

<400> SEQUENCE: 12

Lys Leu Lys Gln Pro Gly
1               5

<210> SEQ ID NO 13
<211> LENGTH: 18
<212> TYPE: PRT
<213> ORGANISM: Plasmodium falciparum
<300> PUBLICATION INFORMATION:
<301> AUTHORS: C. Cerami
<303> JOURNAL: Cell
<304> VOLUME: 70
<306> PAGES: 1021-33
<307> DATE: 1992
<300> PUBLICATION INFORMATION:
<301> AUTHORS: S. Chatterjee
<303> JOURNAL: Infection and Immunity
<304> VOLUME: 63
<306> PAGES: 4375-81
<307> DATE: 1995

<400> SEQUENCE: 13

Glu Trp Ser Pro Cys Ser Val Thr Cys Gly Asn Gly Ile Gln Val Arg
1               5                   10                  15
Ile Lys

<210> SEQ ID NO 14
<211> LENGTH: 11
<212> TYPE: PRT
<213> ORGANISM: Artificial
<220> FEATURE:
<223> OTHER INFORMATION: Adeno 5 wt GH-loop

<400> SEQUENCE: 14

Val Tyr Leu Asn Gly Asp Lys Thr Lys Pro Val
1               5                   10

<210> SEQ ID NO 15
<211> LENGTH: 11
<212> TYPE: PRT
<213> ORGANISM: Artificial
<220> FEATURE:
<223> OTHER INFORMATION: Adeno 5/9 GH-loop chimera

<400> SEQUENCE: 15

Val Tyr Leu Gly Gly Lys Pro Asp Gln Pro Val
1               5                   10

<210> SEQ ID NO 16
<211> LENGTH: 11
<212> TYPE: PRT
<213> ORGANISM: Artificial
<220> FEATURE:
<223> OTHER INFORMATION: Adeno 5 GH-Cys1

<400> SEQUENCE: 16
```

```
Val Tyr Leu Asn Gly Cys Gly Ser Cys Pro Val
1               5                   10

<210> SEQ ID NO 17
<211> LENGTH: 12
<212> TYPE: PRT
<213> ORGANISM: Artificial
<220> FEATURE:
<223> OTHER INFORMATION: Adeno 5 GH-Cys2

<400> SEQUENCE: 17

Val Tyr Leu Asn Gly Cys Gly Ser Gly Cys Pro Val
1               5                   10

<210> SEQ ID NO 18
<211> LENGTH: 21
<212> TYPE: PRT
<213> ORGANISM: Artificial
<220> FEATURE:
<223> OTHER INFORMATION: Adeno 5 GH-peptide
<220> FEATURE:
<221> NAME/KEY: MISC_FEATURE
<222> LOCATION: (8)..(17)
<223> OTHER INFORMATION: Xaa is any amino acid

<400> SEQUENCE: 18

Val Tyr Leu Asn Gly Cys Gly Xaa Xaa Xaa Xaa Xaa Xaa Xaa Xaa
1               5                   10                  15

Xaa Gly Cys Pro Val
            20
```

RECOMBINANT ADENOVIRAL VECTORS EXPRESSING CHIMERIC FIBER PROTEINS FOR CELL SPECIFIC INFECTION AND GENOME INTEGRATION

This application is an application filed under 35 U.S.C. §371 which is based on International Application No. PCT/US00/15442, filed Jun. 1, 2000, which claims the priorities of provisional applications U.S. Ser. No. 60/137,213, filed Jun. 1, 1999 and U.S. Ser. No. 60/161,097, filed Oct. 22, 1999, the contents of all of which are hereby incorporated by reference in their entirety into the present application.

This invention was made, at least in part, with funding from the National Institutes of Health (Grant Nos. R01 CA 80192-01 and R21 DK 55590-01). Accordingly, the United States Government has certain rights in this invention.

FIELD OF THE INVENTION

This invention relates to the field of gene therapy, and in particular, to novel adenovirus (Ad) vectors that selectively infect cells for gene therapy, and to Ad vectors containing modifications of the fiber protein to allow retargeting of any adenovirus serotype.

BACKGROUND OF THE INVENTION

Gene transfer vectors require the efficient transduction of target cells, stable association with the host genome, and adequate transgene expression in the appropriate target cell, without associated toxic or immunological side effects. Currently available viral vector systems, including recombinant retroviruses, adenoviruses and adeno-associated viruses, are not suitable for efficient gene transfer into many cell types. Retroviral vectors require cell division for stable integration. Recombinant adenoviruses are not able to infect many cell types important for gene therapy, including hematopoietic stem cells, monocytes, T- and B-lymphocytes. Moreover, recombinant adeno-associated vectors (AAV) integrate with a low frequency.

First generation adenoviruses have a number of properties that make them an attractive vehicle for gene transfer (Hitt, M. M. et al. 1997 *Advances in Pharmacology* 40:137–205). These include the ability to produce purified virus at high titers in concert with highly efficient gene transfer of up to 8 kb long expression cassettes into a large variety of cell types in vivo, including non-dividing cells. Limitations of first generation adenoviruses include the development of immune responses to expressed viral proteins resulting in toxicity and virus clearance. The episomal status of adenoviral DNA within transduced cells is another limitation of first generation Ad vectors. Stable integration of adenovirus DNA into the host genome is reported only for wild-type forms of specific subtypes and appears not to occur in a detectable manner with E1/E3-deleted Ad 5 (adenovirus serotype 5) vectors widely used for gene transfer in vitro and in vivo [Hitt, M. M. et al. 1997 *Advances in Pharmacology* 40:137–205].

Recombinant AAV vectors (rAAV) integrate with a low frequency (about 1 out of 20,000 genomes) randomly as cocatemers into the host genome (Rutledge, E. A.; Russel, D. W. 1997 *J. Virology*, 71, 8429–8436). The presence of two AAV inverted terminal repeats (ITRs) and as yet unknown host cellular factors seem to be the only requirement for vector integration (Xiao, X., et al, 1997, *J. Virology*, 71, 941–948; Balague, C., et al. 1997, *J. Virology*, 71, 3299–3306; Yang, C. C. 1997, *J. Virology*, 71, 9231–9247). In the presence of the large AAV Rep proteins, AAV integrates preferentially into a specific site at human chromosome 19, called AAVS1 (Berns, K. I., 1996, *Fields Virology*, Fields, B. N. et al. (ed) Vol. 2, Lippincott-Raven, Philadelphia, Pa., 2173–2220). The AAV capsid is formed by three coat proteins (VP1–3), which interact with specific heparin sulfates on the cell surface and probably with specific receptor(s). However, many cell types, including hematopoietic stem cells, lack these structures so that rAAV vectors based on AAV2 cannot infect or transduce these cells (Malik P. et al., 1997, *J. Virology*, 71, 1776–1783; Quing, K. Y., et al. 1998, *J. Virology*, 72, 1593–1599). Other disadvantages of rAAV vectors include the limited insert size (4.5–5 kb) that can be accommodated in rAAV vectors lacking all viral genes and low transducing titers of rAAV preparations.

Adenovirus infection is initiated by attaching to the cell surface of Ad 5 via its fiber protein (for a review, see Shenk, T. 1996 *Fields Virology*, Vol. 2, Fields, B. N. et al. (ed) Vol. 2, Lippincott-Raven, Philadelphia, Pa., 2111–2148). The distal, C-terminal domain of the trimeric fiber molecule terminates in a knob, which binds to a specific cellular receptor identified recently as the coxackie-adenovirus receptor (CAR) (Bergelson, J. M. et al. *Science*, 275, 1320–1323). After binding, in an event independent of virus attachment, Arg-Gly-Asp (RGD) motifs in the penton base interact with cellular integrins of the $\alpha 3$ and $\beta 5$ types. This interaction triggers cellular internalization whereby the virion achieves localization within the endosome. The endosomal membrane is lysed in a process mediated by the penton base, releasing the contents of the endosome to the cytoplasm. During these processes, the virion is gradually uncoated and the adenoviral DNA is transported to the nucleus where replication takes place. The terminal protein, which is covalently attached to the viral genome and the core protein V that is localized on the surface of the cores have nuclear localization signals (NLSs) (van der Vliet, B. 1995, *The Molecular Repertoir of Adenoviruses*, Vol. 2, Doerfler, W. and Boehm, P. (ed.), Springer Verlag, Berlin, 1–31). These NLSs play a crucial role in directing the adenoviral genome to the nucleus and probably represent the structural elements which allow adenovirus to transduce non-dividing cells. When the double-stranded, linear DNA reaches the nucleus, it binds to the nuclear matrix through its terminal protein.

Since the cell types that can be infected with Ad5 or Ad2 vectors are restricted by the presence of CAR and specific integrins, attempts have been made to widen the tropism of Ad vectors. Genetic modification of adenovirus coat proteins to target novel cell surface receptors have been reported for the fiber (Krasnykh, V. et al. 1998 *J. Virology*, 72, 1844–1852, Krasnykh, V. et al. 1996 *J. Virology*, 70, 6839–6846, Stevenson, S. D., et al. 1997, *J. Virology*, 71, 4782–4790), penton base (Wickham, T. J., et al. 1996, *J. Virology*, 70, 6831–6838; Wickham, T. J., et al. 1995, *Gene Therapy*, 69, 750–756), and hexon proteins (Crompton, J., et al. 1994, *J. Gen. Virol.* 75, 133–139). The most promising modification seems to be the functional modification of the fiber protein or more specifically of the fiber knob as the moiety, which mediates the primary attachment. Two groups have reported the generation of fibers consisting of the Ad5 tail/shaft and the knob domain of Ad3 (Krasnykh, V. et al. 1996 supra, Stevenson, S. D., et al. 1997, supra). Recently, recombinant adenoviruses with fibers containing C-terminal poly-lysine, gastrin-releasing peptide, somatostatin, E-selectin-binding peptide, or oligo-Histidines were produced in order to change the native tropism of Ad5. Krasnikh et al. found (Krasnykh, V. et al. 1998 supra) that heterologous peptide ligands could be inserted into the H1 loop of the fiber knob domain without affecting the biological function of the fiber. Based on studies with other Ad serotypes, it appears that the length of the fiber shaft is a critical element, determining the efficiency of interaction with cell surface integrins and the internalization process. Thus far, there is no reported data demonstrating successful retargeting of Ad5 vectors for a specific cell type.

Therefore, there is a present need for an improved adenovirus vector which can be targeted efficiently to a variety of cell types and tissues and remain stably integrated in the host genome with minimal antigenicity to the host. The present invention discloses novel chimeric adenoviral (Ad) Ad-AAV vectors, which express a modified fiber protein on their capsid, for specifically targeting the vector. Methods of making, uses and advantages of these vectors are described. In addition, the alteration described for the knob and shaft domains of the fiber protein provide a novel approach to retarget any adenovirus serotype for cell specific infection.

SUMMARY OF THE INVENTION

The present invention provides for novel chimeric Ad-vectors carrying transgene, or portions of transgenes for stable and efficient gene transfer into diverse cell types or tissues in a CAR- and/or $\alpha_v\beta_{3/5}$-independent manner. Also provided are methods for producing such vectors and the use thereof for gene therapy to target a specific cell type or tissue.

The recombinant adenovirus vectors of the invention (Example I) provide a novel design that allows for the easy production and delivery of a "gutless" adenoviral vector with the added advantage of stable integration of the transgene into the host genome of different cell type. The adenoviral vector described is devoid of all adenoviral sequences except for the 5' and 3' cis elements necessary for replication and virion encapsidation. The adenovirus-associated virus sequences of the invention comprising the 5' (right) and 3' (left) inverted terminal repeats (ITRs) flank the transgene gene cassette such that they direct homologous recombination during viral replication and viral integration into the host genome. In one embodiment AAV-ITR flanking sequences are used. The vector also contains a selected transgene(s) operably linked to a selected regulatory element and a polydenylation stop signal, which is in turn flanked by the flanking sequences described above. The selected transgene(s) can be linked under the same regulatory elements or under separate regulatory elements in the same orientation or in opposite orientations with respect to each other. The selected transgene(s) are any gene or genes which are expressed in a host cell or tissue for therapeutic, reporter or selection purposes. This vector is characterized by high titer transgene delivery to a host cell and the ability to stably integrate the transgene into the host genome. Also provided is a method to improve the integration frequency and site specific integration by incorporating an AAV rep protein into the recombinant hybrid vector.

The invention also provides chimeric fiber proteins (Example II), which includes naturally occurring fiber proteins in which a portion or portions of the sequence are modified to alter cell or tissue specificity of infection. Altered fiber protein sequences can include fiber protein domains (the knob domain, the shaft domain, and the tail domain) from other or the same adenovirus serotypes or from randomly selected peptides. A chimeric fiber protein can be entirely composed of non-naturally occurring sequences. The invention further relates to nucleic acid sequences encoding the chimeric fiber proteins. These nucleic acid sequences can be naturally occurring, a mixture of naturally occurring and non-naturally occurring sequences, or entirely non-naturally occurring sequences.

The heterologous fiber protein sequences described herein can be inserted into any adenovirus based vector which contains a capsid, rendering the virus capable of specifically infecting a given cell or tissue. Adenoviral vectors having such a heterologous fiber sequence can be used to direct gene transfer into desired cells. For stable integration of the transgene cassette into the host gemone, the chimeric Ad-AAV vector described in the invention is the preferred vector of use.

The invention also includes a library of adenoviruses displaying random peptides in their fiber knobs can be used as ligands to screen for an adenovirus variant with tropism to a particular cell type in vitro and in vivo.

The chimeric Ad-vectors described herein include the Ad.AAV genome with a modified fiber protein expressed on its capsid. These chimeric vectors are designed to infect a wide variety of cells, in particular, the cells which can only be poorly transduced by the commonly used retroviral, AAV and adenoviral vectors. These cells include, but not limited to, hematopoietic stem cells, lung epithelial cells, dendritic cells, lymphoblastoid cells, and endothelial cells. Hematopoietic stem cells such as CD34+ cells can be targeted for gene therapy of sickle cell anemia and thalasemia using the vector described herein. The chimeric Ad-AAV vector capable of transducing genes into endothelial cells can be used in gene therapy for vascular diseases such as atherosclerosis or restinosis after coronary artery surgery.

BRIEF DESCRIPTION OF THE FIGURES

FIG. 2A shows Ad.AAV1 and FIG. 2B shows ΔAd.AAV1.

FIGS. 4A and 4B show response of K562 and CD34+ cells respectively after infection with ΔAd.AAVBG. Cells are incubated for 6 hours with virus under agitation. At day 3 after infection, transduction frequency is calculated based on the number of X-Gal positive cells. Viability is tested by trypan blue exclusion. N=3, SEM<10%.

FIGS. 8A–8B shows vectors for transduction studies with SNori as expression unit and analysis of vector integration on genomic DNA from a small cell number. Analgous vector sets can be generated with β-galactosidase (BG) or green fluorescence protein (GFP) as reporter genes.

FIG. 10 shows the expression of CAR and $\Delta_v$-integrins on test cells. For flow cytometry analysis, HeLa, CHO, K562, and CD34+ cells were incubated with monoclonal anti-CAR (RmcB, 1:400 dilution) or anti-$\Delta_v$-integrin antibodies (L230, 1:30 dilution). As a negative control, cells were incubated with an irrelevant mouse monoclonal antibody (anti-BrdU, 1:100 dilution). The binding of primary antibodies was developed with anti-mouse IgG-FITC labeled conjugates (1:100 dilution). Data shown represent the average results of quadruplicate analyses performed on $10^4$ cells.

FIG. 11 shows the electron microscopy of adenovirus particles. Purified particles from Ad5, 9, and 35 were negative contrast stained and analyzed at a magnification of 85,000×. Defective particles are highlighted by arrows.

FIG. 17A–17B shows the generation of ΔAd.AAV genomes by recombination between inverted homology regions. A) Recombination between two inverted repeats (IRs) present in separate Ad.AAV vectors. The upper first-generation Ad.AAV vector (~34 kb) contains two 1.2 kb IRs flanking Gene X. An AAV-ITR ("AAV.ITR") is located between the Ad packaging signal (Ψ) and the left IR. The lower Ad.AAV vector, shown in the opposite orientation, contains the same IRs flanking a transgene cassette. An AAV-ITR is located between the left IR and the Ad packaging signal. During Ad replication, recombination between an IR on each vector (indicated by an X) mediates the formation of ΔAd.AAV genomes (lower portion of panel A) with the transgene flanked by IRs, AAV-ITRs, Ad packaging signals, and Ad ITRs. These genomes are efficiently packaged into Ad capsids. The other recombination product (not shown) is a defective Ad.AAV vector lacking packaging signals. B) Recombination between homology regions of Gene X present in separate Ad.AAV vectors. The upper Ad.AAV vector contains a promoter (P) operably linked to the 5' portion of Gene X. An AAV-ITR is inserted between the Ad packaging signal (T) and the promoter. The lower Ad.AAV vector, shown in the opposite orientation, contains the 3' portion of Gene X linked to a poly-adenylation region (PA). An AAV-ITR is inserted between the Ad packaging signal (T) and the polyadenylation region. The 5' portion of Gene X in the upper vector has a region of overlapping homology with the 3' portion of Gene X in the lower vector. Recombination between the overlapping homology regions (indicated by an X) mediates the formation of ΔAd.AAV genomes with the assembled Gene X flanked by AAV-ITRs, Ad packaging signals, and Ad ITRs.

Figure 1:
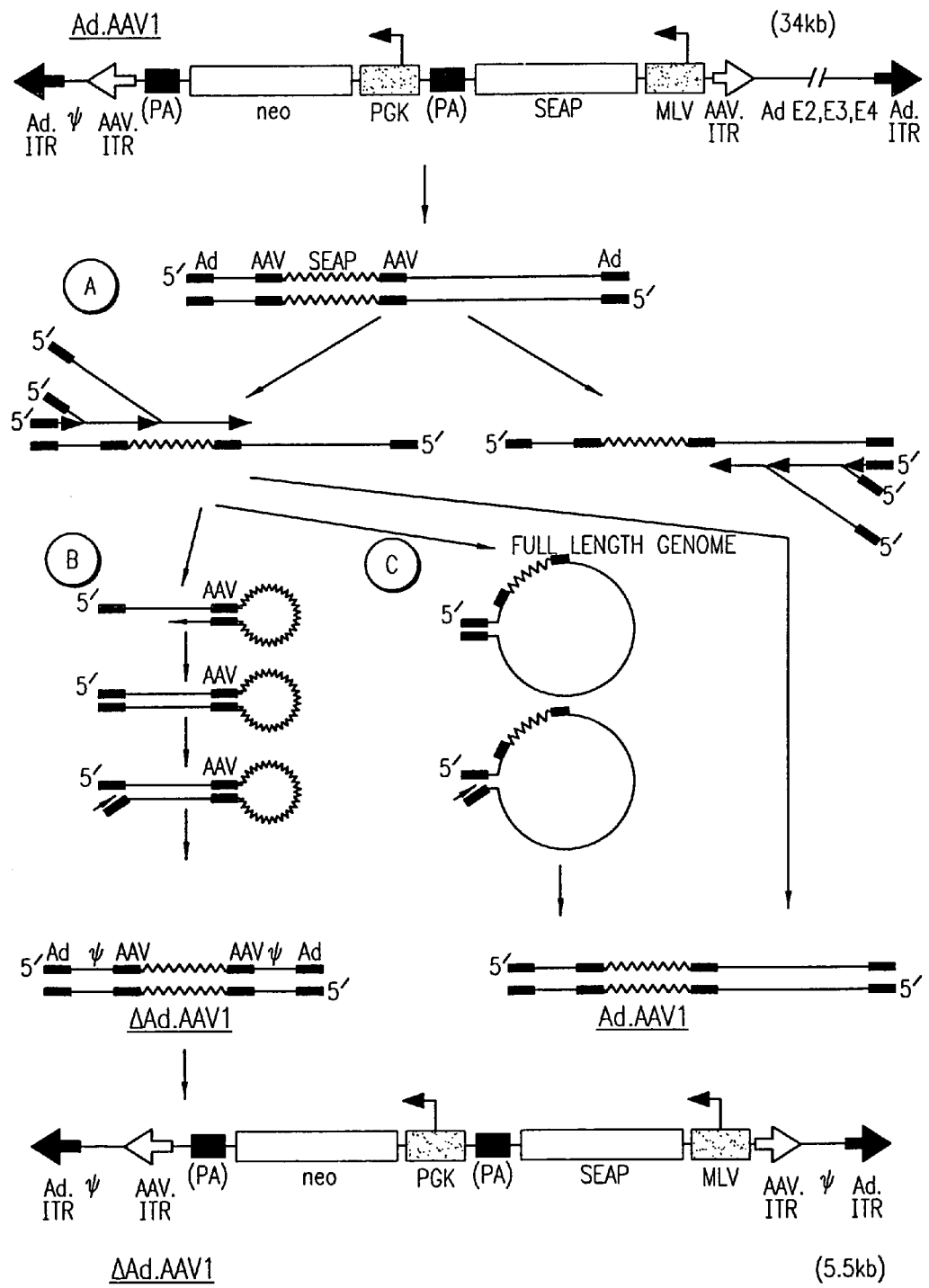
FIGS. 1A–1C display a proposed mechanism for forming of ΔAd.AAV1 genome.

A conserved stretch of amino acids TLWT marks the boundary between the last β-sheet of Ad35 shaft and the globular knob. The Ad35 fiber chain termination codon is followed by the Ad5 fiber poly-adenylation signal.

FIG. 19 shows the cross-competition for attachment and internalization of labeled Ad5GFP, Ad35, and chimeric Ad5GFP/F35 virions with unlabeled viruses, and with anti-CAR or anti-$\alpha_v$-integrins Mab. (A) For attachment studies, $10^5$ K562 cells were pre-incubated with a 100-fold excess of unlabeled competitor virus at 4° C. for 1 h. Then, equal amounts of [$^3$H]-labeled viruses, at a dose equivalent to an MOI of 100 pfu per cell determined for Ad5GFP, were added to cells followed by incubation at 4° C. for 1 h. Cells were then washed with ice-cold PBS, pelleted and the percentage of attached virus (cell-associated counts per minute) was determined. For analysis of cross-competition for internalization, cells were pre-incubated with a 100-fold excess of competitor virus at 37° C. for 30 min before labeled virus was added. After an additional incubation at 37° C. for 30 min, cells were treated with trypsin-EDTA for 5 min at 37° C., washed with ice-cold PBS, pelleted, and the percentage of internalized virus was determined. For controls, cells were incubated with labeled viruses without any competitors. Preliminary experiments had shown that the conditions chosen for competition studies allowed for saturation in attachment/internalization on K562 cells for all unlabeled competitors. (B) $10^5$ K562 cells were pre-incubated for 1 hour at 4° C. with anti-CAR MAb (RmcB, diluted 1:100) or with anti-$\alpha_v$-integrin MAb (L230, diluted 1:30), followed by incubation with labeled viruses according to the protocols for attachment or for internalization as described above. For each particular serotype, the percentage of attached/internalized virus was compared to the control settings, where cells were preincubated under the same conditions with a 1:100 dilution of an irrelevant antibody (anti-BrdU Mab) before addition of the labeled virus. Note that the specific competitors but not the corresponding controls significantly inhibited Ad5 internalization to a degree that is in agreement with published data (59). N>/=4. (C) In internalization studies, Ad5 did not inhibit internalization of Ad35 or Ad5GFP/F35 into K562 cells. (D) In internalization studies, L230 monoclonal antibody did not inhibit internalization of Ad35 or Ad5GFP/F35 into K562 cells.

FIG. 20. Cross-competition for attachment and internalization of [$^3$H]-labeled Ad5GFP, Ad35, and chimeric Ad5GFP/F35 virions with unlabeled Ad3 virus (A), and of [$^3$H]-labeled Ad3 virions with unlabeled viruses (B). $10^5$ K562 cells were pre-incubated with a 100-fold excess of unlabeled viral particles according to attachment or internalization protocols described for FIG. 6. Equal amounts of [$^3$H]-labeled Ad5GFP, Ad5GFP/F35, or Ad35 (A) or [$^3$H]-labeled Ad3 (B) were added to cells at a dose equivalent to an MOI of 100 pfu per cell for Ad5GFP. In control settings, cells were incubated with labeled viruses without any competitors. N=4. (C) In attachment studies, Ad35 does not significantly inhibit attachment of Ad3 to K562 cells. (D) In internalization studies, cells pre-incubated with Ad35 significantly inhibit internalization of Ad3.

Figure 21:
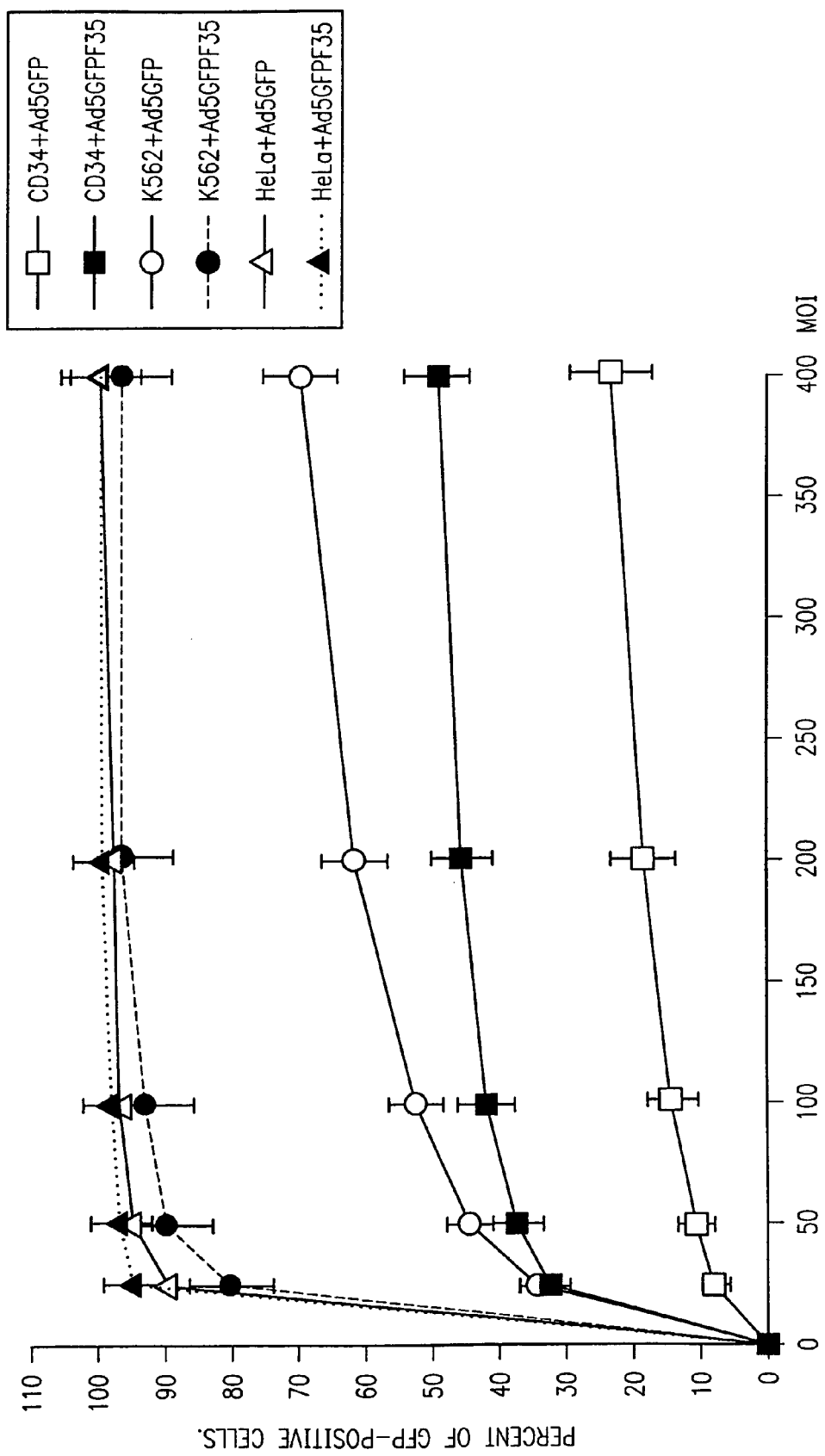

FIG. 21 shows the transduction of CD34+, K562, and HeLa cells with Ad5GFP and chimeric Ad5GFP/F35 vectors. $1\times10^5$ cells were infected with different MOIs (pfu/cell) of viruses in 100 μl of media for 6 hours at 37° C. Virus containing media was then removed, and the cells were resuspended in fresh media followed by incubation for 18 h at 37° C. The percentage of GFP expressing cells was determined by flow cytometry. N=3

Figure 22:
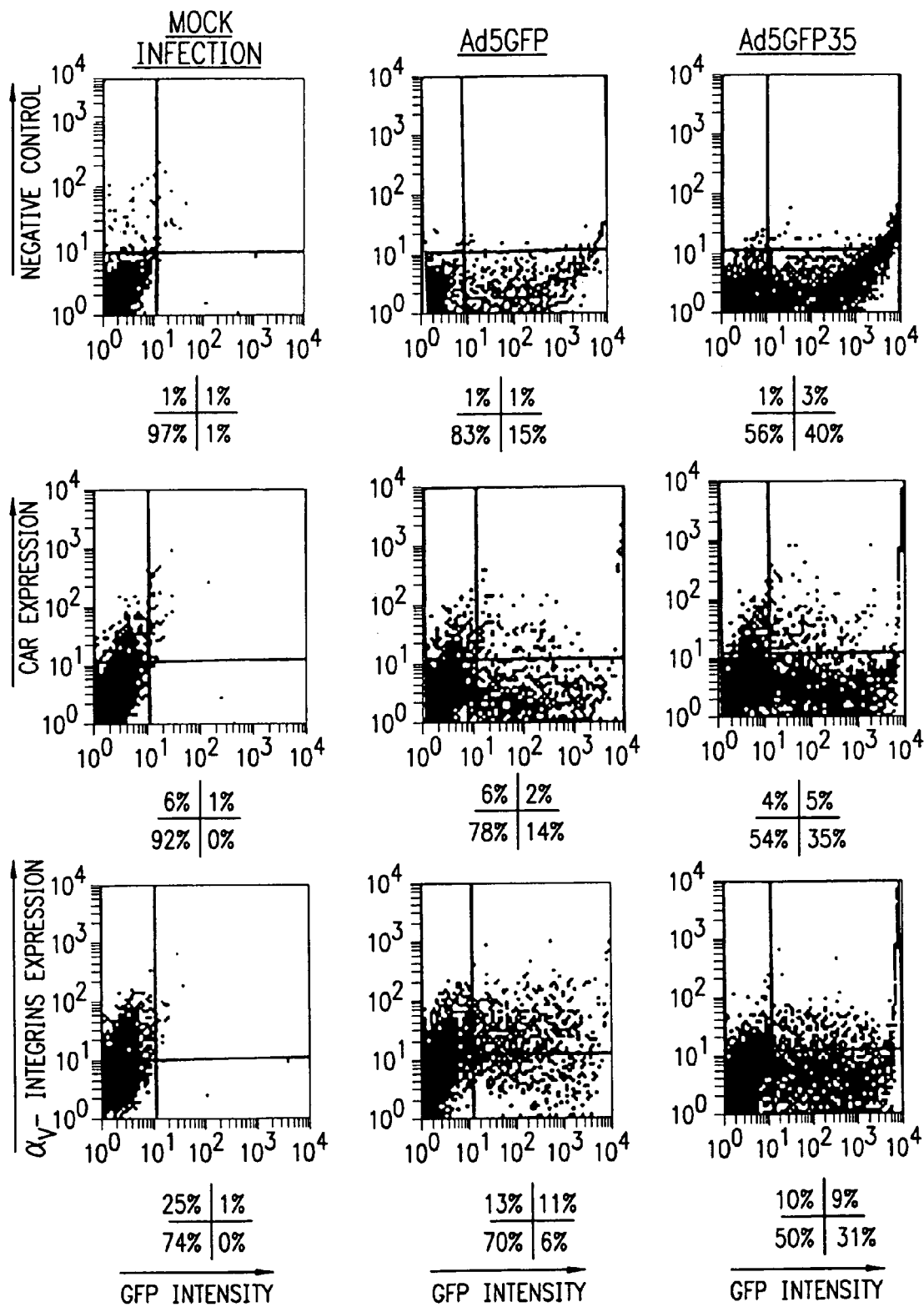

FIG. 22 shows the distribution of GFP-positive cells in subpopulations of human CD34+ cells expressing CAR or $\alpha_v$-integrins. $1\times10^5$ CD34+ cells were infected with Ad5GFP or Ad5GFP/F35 at an MOI of 200 pfu/cell. Twenty-four hours after infection, cells were incubated with anti-CAR (1:100 final dilution) or anti-$\alpha_v$-integrin (1:30 final dilution) primary MAbs for 1 h at 37° C. Binding of primary antibodies was developed with anti-mouse IgG-PE labeled secondary MAbs (1:100 final dilution) at 4° C. for 30 min. For each variant, $10^4$ cells were analyzed by flow-cytometry. The mock infection variants represent cells incubated with virus dilution buffer only. The quadrant borders were set based on the background signals obtained with both the GFP- and PE-matched negative controls. The percentages of stained cells found in each quadrant are indicated. The data shown were representative for three independent experiments.

Figure 23A:
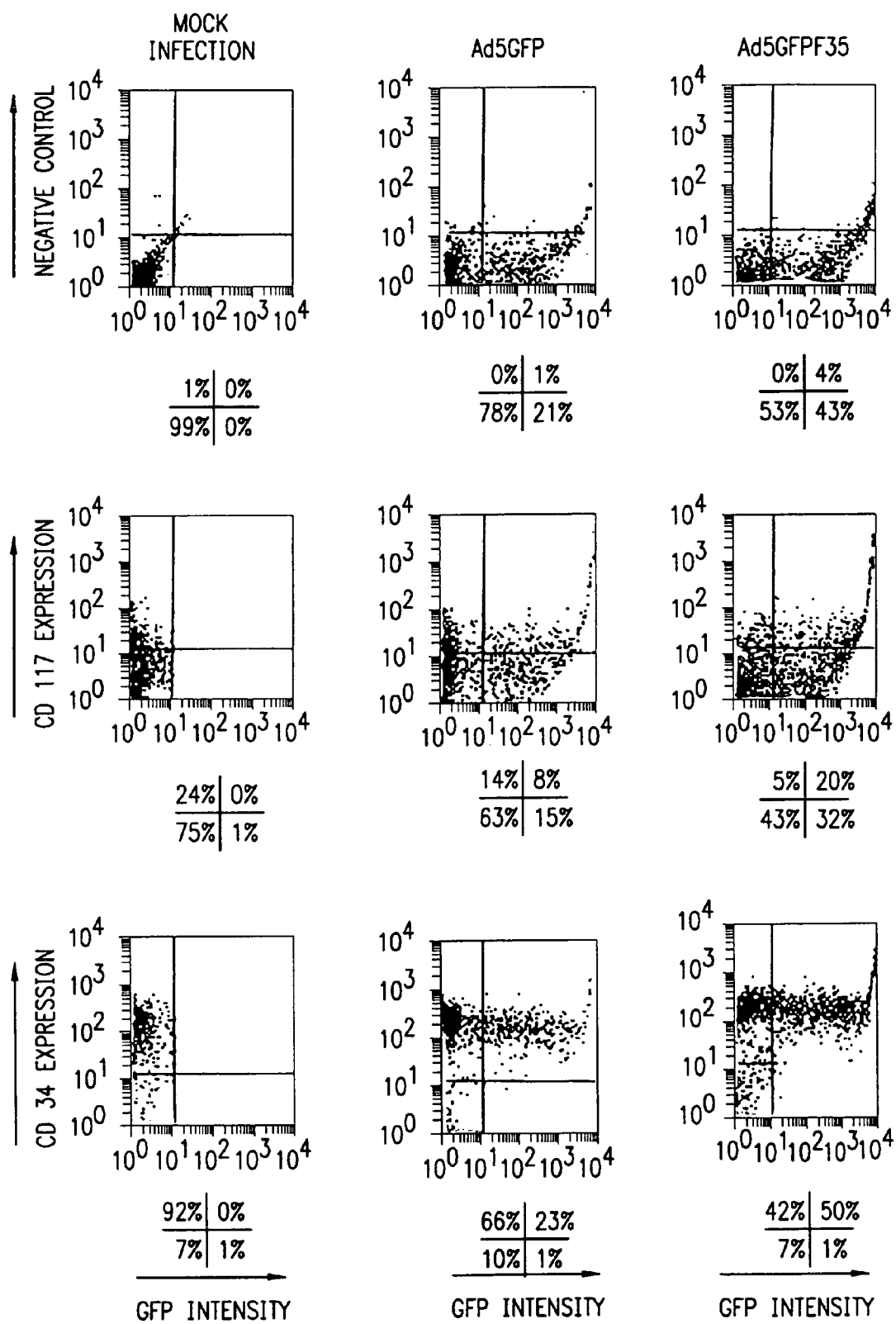
Figure 23B:
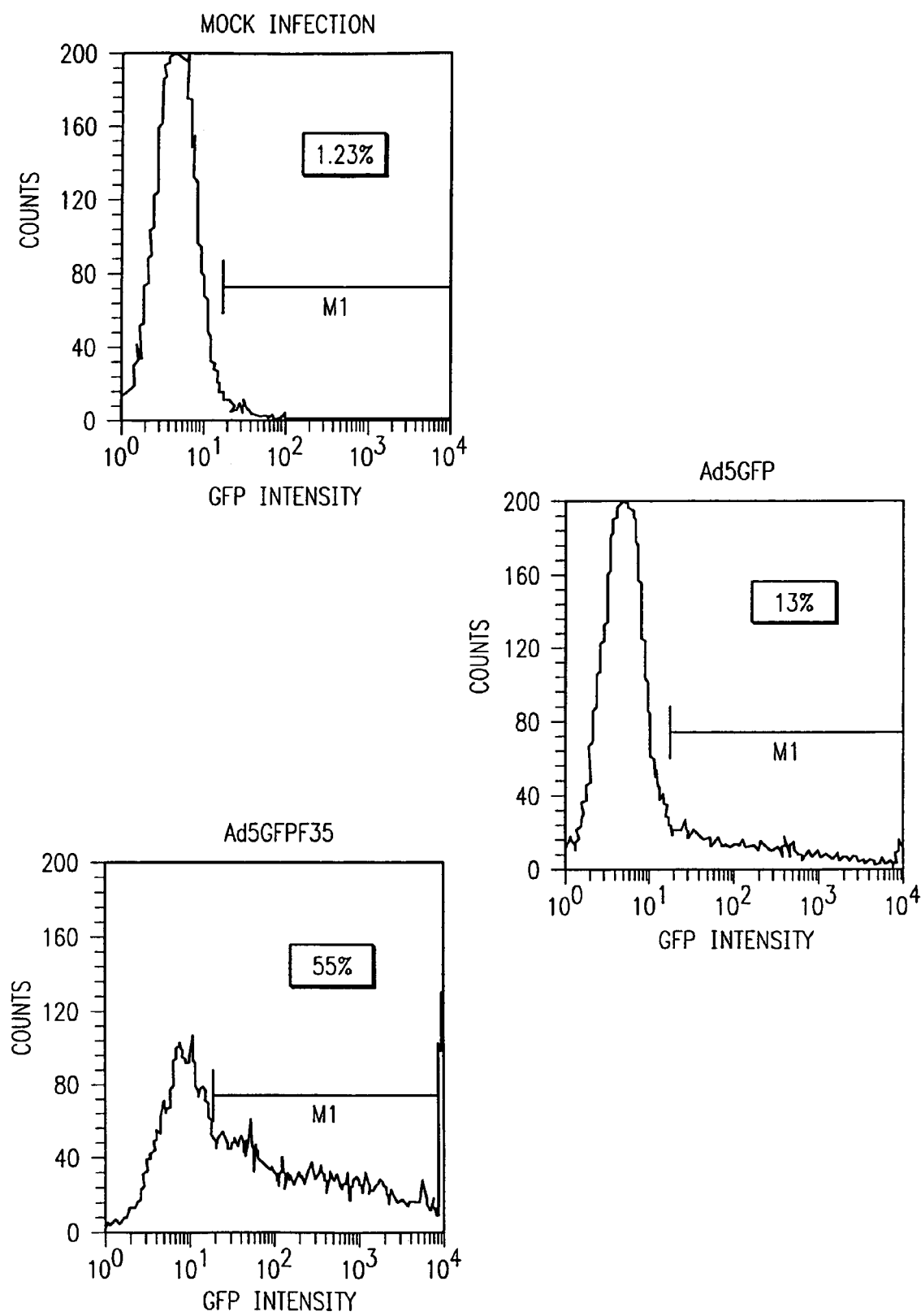

FIGS. 23A–23B shows the distribution of GFP-positive cells in a subpopulation of human CD34+ cells, expressing CD34 and CD117 (c-kit). (A) Co-localization of GFP expression with CD34 or CD117: CD34+ cells were infected with Ad5GFP or Ad5GFP/F35 at an MOI of 200 pfu per cell under the conditions. Twenty-four hours after infection, cells were incubated with anti-CD34 PE-conjugated MAbs (final dilution 1:2) or with anti-CD117 PE-conjugated MAbs (final dilution 1:5) for 30 min on ice, and $10^4$ cells per variant were subjected to two-color flow cytometry analysis. For negative control staining, no antibodies were added to the cells before analysis. The mock infection variants represent cells incubated with virus dilution buffer only. The quadrant borders were set based on the background signals obtained with both the GFP- and PE-matched negative controls. The percentages of stained cells found in each quadrant are indicated. The experiment was performed two times in triplicates, and typically obtained results are shown. The SEM was less than 10% of the statistical average. (B) Transduction of CD34+/CD117+ cells with Ad5GFP and chimeric Ad5GFP/F35 virus vectors: CD34+ cells, cultured overnight before staining in media without SCF, were incubated with PE-labeled anti-CD117 MAb for 30 min on ice. The fraction of CD117-positive cells was sorted by FACS. More than 97% of sorted cells were positive for CD117. $1 \times 10^5$ CD117+/CD34+ cells were infected with Ad5GFP or Ad5GFP/F35 at an MOI of 200 pfu per cell. Twenty-four hours post infection, the percentage of GFP positive was determined by flow cytometry. For mock infection, CD117+/CD34+ cells were incubated with virus dilution buffer only. The infections were done in triplicates, and the average percentage of GFP-expressing cells is indicated on the corresponding histogram. The SEM was less than 10% of the statistical average.

FIG. 24 shows the southern analysis of viral genomes in GFP-positive and GFP-negative fractions of CD34+ cells infected with the Ad5GFP and chimeric Ad5GFP/F35 vectors. CD34+ cells were infected with viruses at an MOI of 100 as described for FIG. 21. Twenty four-hours post infection, cells were sorted by FACS for GFP positive and GFP negative fractions. $10^5$ cells from each fraction were used to isolate genomic DNA, together with viral DNA. Before cell lysis, a rigorous treatment with trypsin and DNase followed by washing was performed to exclude that genomic DNA samples were contaminated by extracellular viral DNA. A) The upper panel shows the ethidium bromide stained 1% agarose gel before blotting demonstrating that similar amounts of genomic DNA were loaded. This amount corresponded to DNA isolated from ~25,000 GFP+ or GFP− cells. The lane labeled Aload@ represents viral DNA purified from Ad5GFP or Ad5GFP/F35 virions mixed with pBluescript plasmid DNA (Stratagene) as a carrier and applied on a gel at the amount that was actually used to infect 25,000 cells. As a concentration standard, a serial dilution of Ad5GFP genomes was loaded on the gel (left side). For Southern analysis (lower panel), an 8 kb-long HindIII fragment corresponding to the E2 region of Ad5 was used as a labeled probe. Hybridized filters were subjected to PhosphoImager analyis and then exposed to Kodak-X-OMAT film for 48 h at B70° C. The cellular/viral genomic DNA is indicated by an arrow. (B) To detect Ad5GFP genomes in transduced cells, PCR amplification followed by Southern blot hybridization was performed on the same samples that were used for quantitative Southern blot hybridization in (A). DNA purified from ~2,500 cells was subjected to PCR (95° CB1 min, 53° C-1 min, 72° CB 1 min, 20 cycles with primers Ad5-F1 and Ad5-R1). One fifth of the PCR reaction was subjected to agarose gel electrophoresis (upper panel). A 0.9 kb-long DNA fragment, specific to the E4 region of Ad5 was detected for transduced Ad5GFP/F35 genomes. DNA then was blotted onto Nybond-N+ membrane and Southern blot hybridization (lower panel) with an Ad5 E4 specific DNA probe was performed. In addition to the 0.9 kb DNA fragment, the PCR primers generated a smaller 0.5 kb-long fragment that also hybridized with with the E4 region probe.

FIG. 25 shows the role of fiber shaft length in Ad infection strategies. CAR binding (Ad5 and Ad9) variants and Ad35, which interacts with a non-CAR receptor were analyzed on CAR expressing cells (293, Y79) and K562 cells which do not express significant CAR amounts. All vectors contain a GFP expression cassette packaged into an Ad5 capsid with modified fibers.

Figure 26:
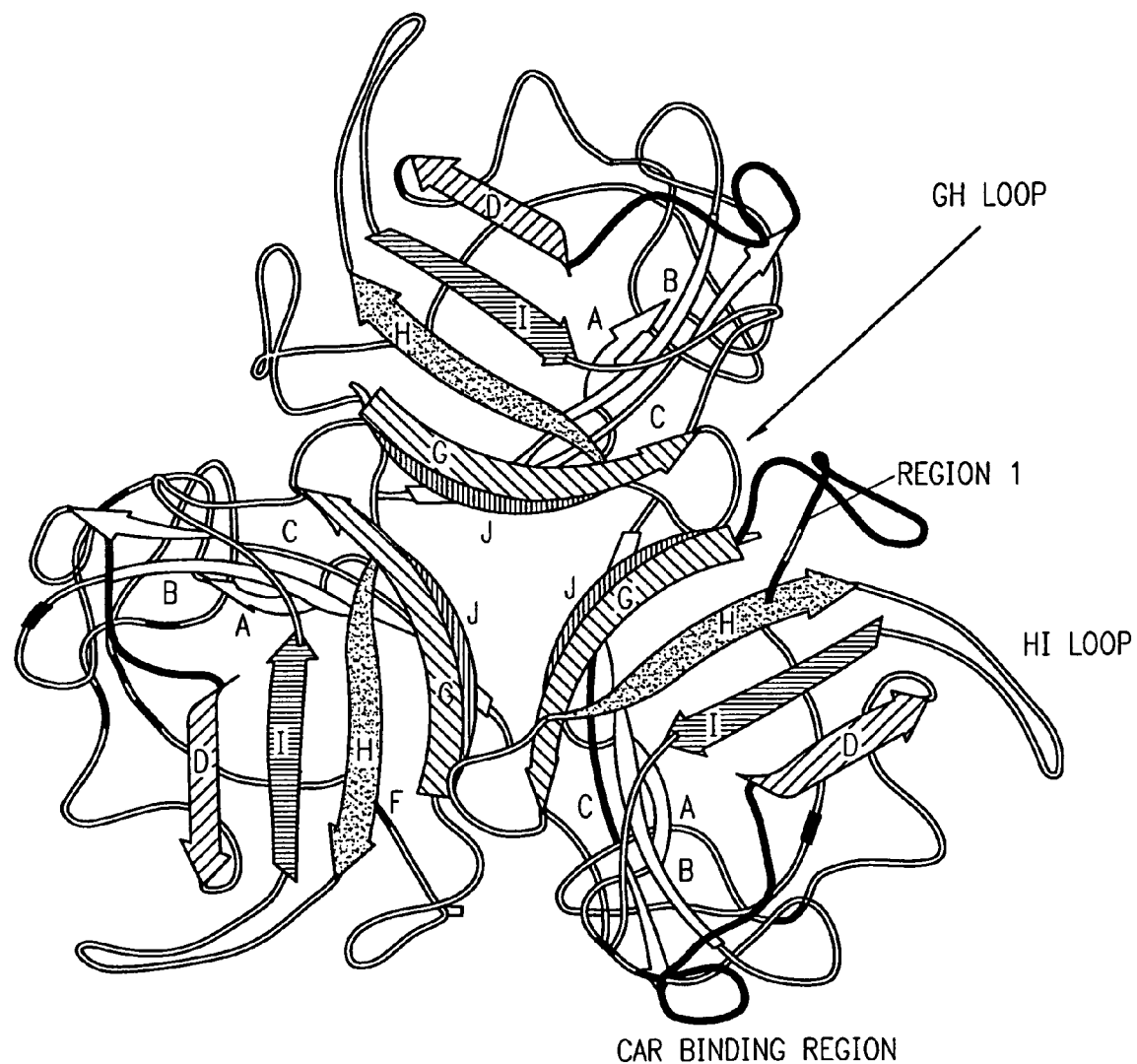

FIG. 26 shows the tertiary structure of Ad5 knob: localization of CAR binding sites, H—I loop and G-H loop.

Figure 27:
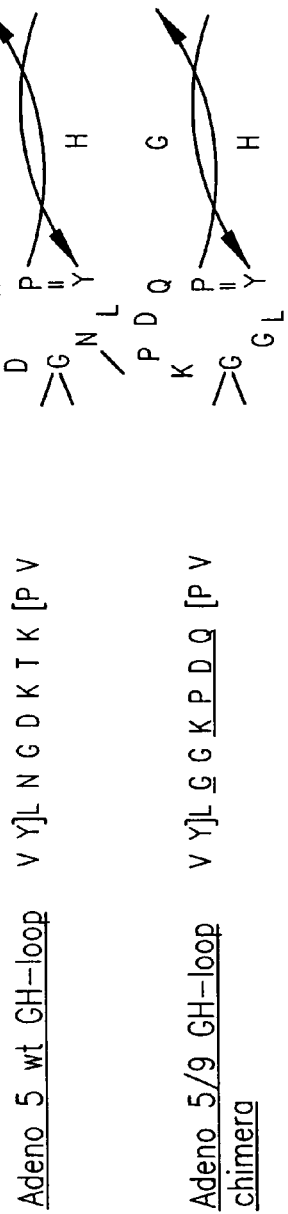

FIG. 27 shows the substitution of the G-H loop with heterologous peptides (SEQ ID NOs.: 14–18).

Figure 28:
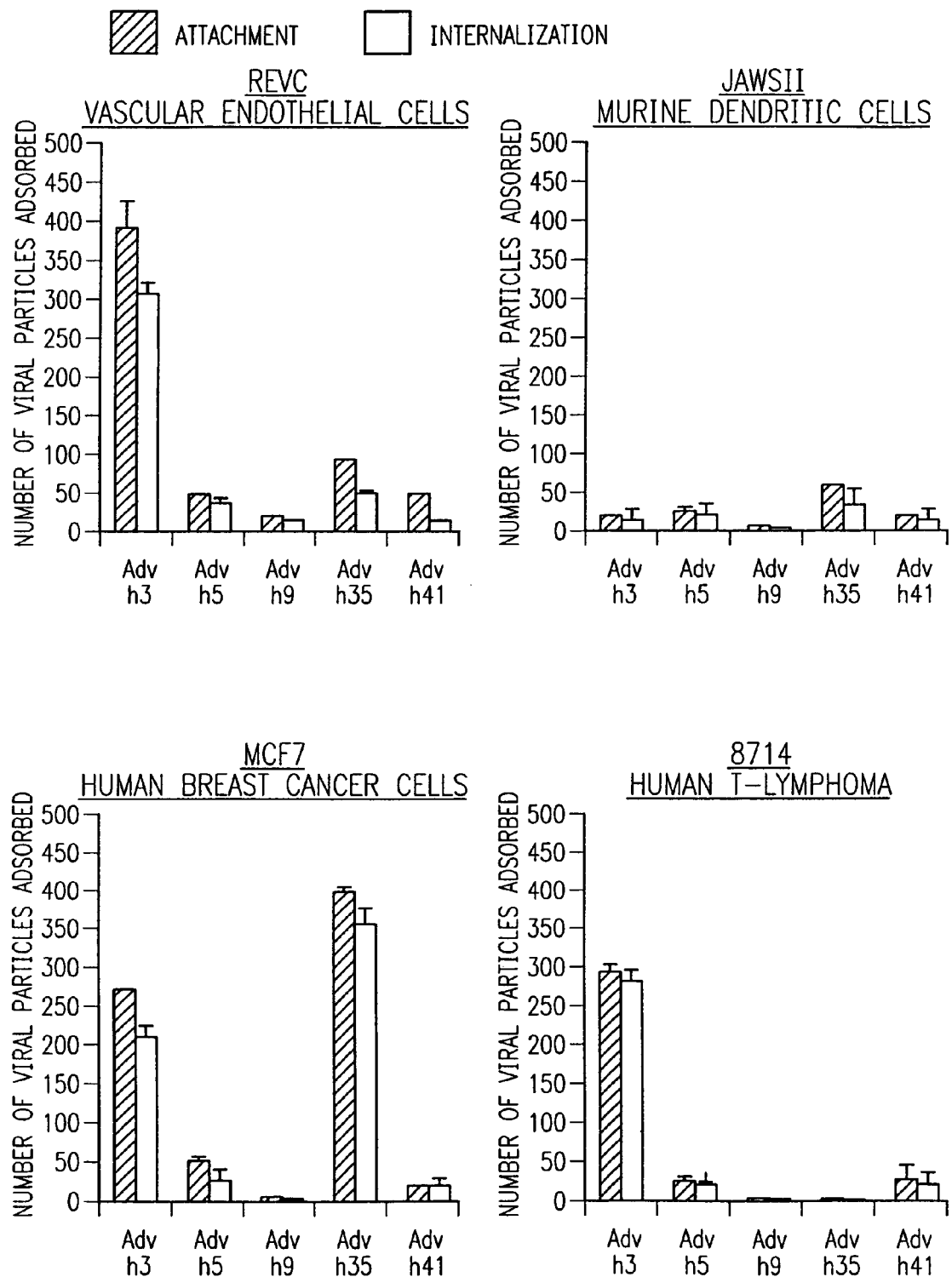
Figure 29A:
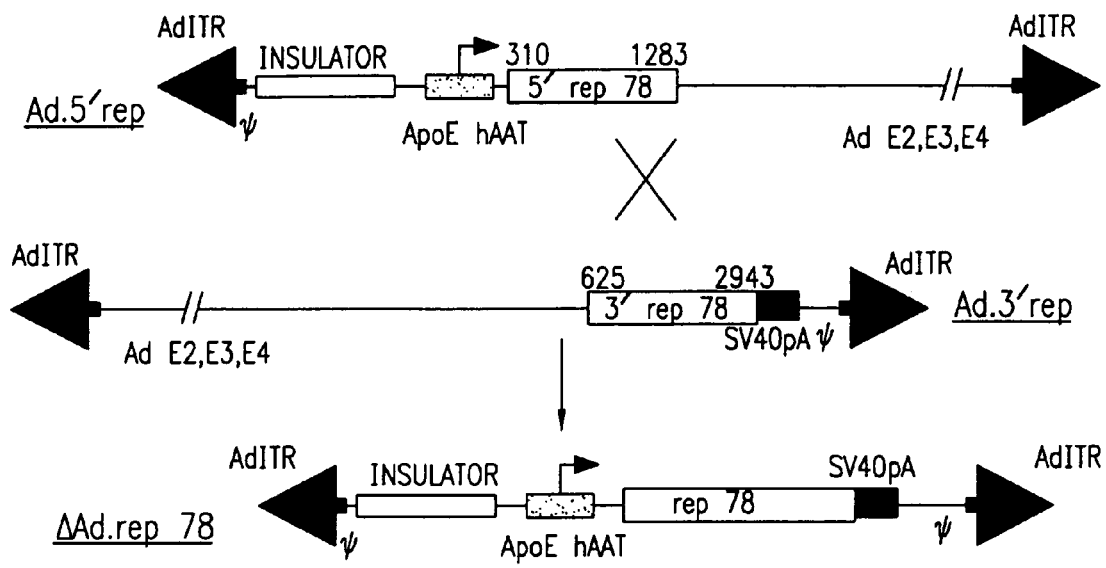
Figure 29B:
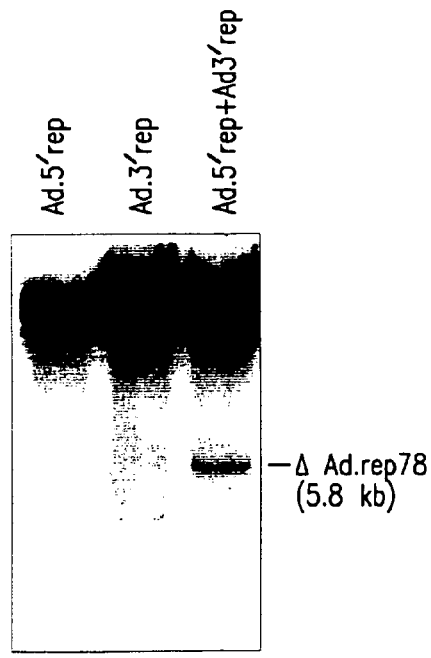
Figure 29C:
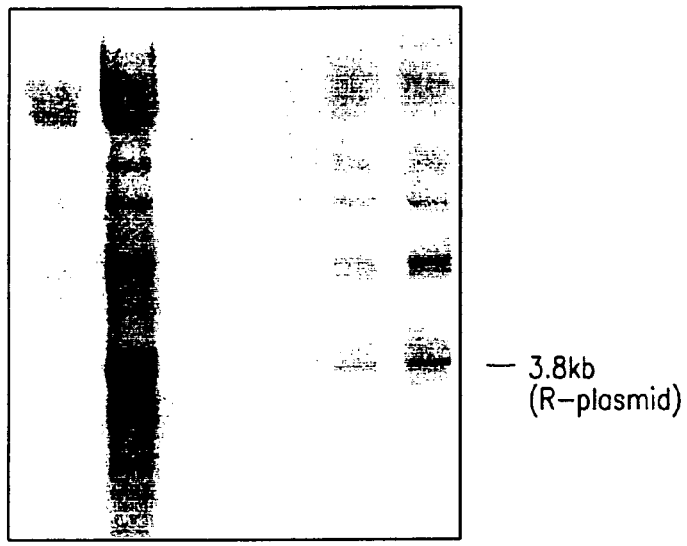
Figure 29D:
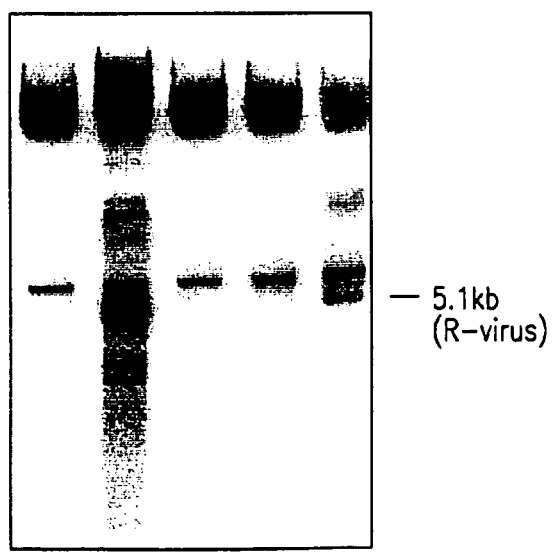

FIG. 28 shows the attachment and internalization of metabolically labeled serotypes with human cell lines.

FIGS. 29A–29D shows the generation of Rep78 expressing Ad vectors by recombination between two vectors. (A) The same strategy outlined in FIG. 15 was employed for vectors with rep 78 as a transgene. The Ad5'rep vector also contained the ApoEhAAT promoter shielded by an HS-4 insulator. The region of homology between the two fragments of the rep78 gene was 658 nt in length. The Rep78 ORF was deleted for the p5 promoter. The internal Rep 40/52 start codon (at position 993) was mutated to abolish production of the small Rep proteins. Furthermore, the splice site at nt 1905 was deleted eliminating production of Rep68. The individual expression of Rep 78 was demonstrated. (B) Formation of ΔAd.rep78 genomes. The expected 5.8 kb ΔAd.rep78 genome was only observed upon coninfection of both Ad5'rep and Ad3'rep into 293 celss as demonstrated by Southern. (C) Southern blot analysis for rescue of the recombinant AAV genome from plasmid DNA by Rep78 expressed from pCMVrep78 and ΔAd.rep78. The expected rescue product is 3.8 kb (R-plasmid). (D) Southern blot analysis for rescue of the recombinant AAV genome from Ad.AAV viral vector genomes.

DETAILED DESCRIPTION OF THE INVENTION

All scientific and technical terms used in this application have meanings commonly used in the art unless otherwise specified. As used in in the present invention, the following words or phrases have the meanings specified.

The term vector includes, but is not limited to, plasmids, cosmids, phagemids, and artificial chromosomes. The vector sequence may be designated as the viral "base vector" sequence. The base vector sequence is dependent upon the particular type of virus and serotype that the base vector sequence was derived from. The base vector sequence may be linked to non-vector or transgene sequences (e.g., heterologous sequences).

The transgene sequences may include sequences that confer compatibility with prokaryote or eukaryote host cells, where compatibility relates to vector replication within a host cell. Accordingly, the transgene sequence may be a replicon sequence that directs replication of the vector within the host cell, resulting in an autonomously replicating vector. Alternatively, the transgene sequence may permit vector replication that is dependent upon the host cell's replication machinery.

The base vector sequences may be a operatively linked to a transgene sequence that encodes a gene product, such as a polypeptide, rRNA, or tRNA. For example, the transgene may encode a polypeptide such as a viral capsid protein, or a viral fiber protein. The transgene may be derived from the same or different serotype as the base vector sequence.

Another example of a transgene includes a reporter gene that encodes a gene product that can be used as a selectable marker, such as drug resistance or a calorimetric marker. The reporter gene may encode a gene product which can be readily detected by, for example, a visual microscopic, immunochemical, or enzymatic assay. The preferred reporter gene encodes a gene product that can be detected by a non-destructive method that does not destroy the cell that expresses the reporter gene.

A therapeutic gene is another example of a transgene. A therapeutic gene encodes a gene product (e.g., polypeptide or RNA) which when expressed in a host cell provides a therapeutic benefit or desired function to the host cell or the tissue or the organ or the organism containing the host cell. The therapeutic benefit may result from modifying a functin of a gene in the host genome or from the additional function provided by the therapeutic protein, polypeptide or RNA.

The base vector sequence may be linked to a transgene sequence that is an regulatory element, such as a promoters, enhancers, transcription termination signals, polyadenylation sequences. The regulatory element may direct expression of the transgene sequence that encodes a gene product by direct transcription or translation. The regulatory element may regulate the amount or timing of expression of the transgene sequence. The regulatory element may direct expression of the transgene in certain host cells or tissues (e.g., host-specific or tissue-specific expression).

The base vector sequence may linked to a transgene sequence that permits the vector, to integrate into another nucleotide sequence. The integration sequence may direct integration of the whole vector or portions of the vector. The integration sequence may or may not be related to the base vector sequence. For example the integration and base vector sequences may be from the same or different viral serotype. The integration sequence may be inverted repeat sequences (ITRs) from adenovirus (Ad), adenovirus-associated virus (AAV), or HIV.

The base vector sequence may be linked to a transgene sequence that directs homologous recombination of the vector into the genome of a host cell. Such transgene sequences may or may not be from the same viral serotype as the base vector sequence.

The vector may be used to transport the heterologous sequence into a host cell or into a host cell's genome.

The vector may comprise multiple endonuclease restriction sites that enable convenient insertion of exogenous DNA sequences.

The term "hybrid vector" as used in the invention refers to a vector which comprises a nucleic acid sequence combined from two different viruses (e.g. Adenovirus and AAV).

"Chimeric vector" refers to a vector which contains nucleic acid sequences that are unnatural to the base vector (i.e. sequences not occurring naturally or sequences not in their natural background including heterologous sequences). A chimeric vector as used in the invention may also be a hybrid vector. An example of a chimeric vector is Ad.AAV expressing a modified fiber protein an its capsid.

The term "transduction" or "infection" refers to a method of introducing viral DNA within a virus particle into a host cell. The viral DNA herein is in the form of recombinant virus, which is generated by linking a segment of DNA of interest into the viral genome in such a way that the gene can be expressed as a functional protein.

The term "transfection" refers to a method of introducing a DNA fragment into a host cell.

The term "heterologous" as used herein means that a nucleic acid or peptide sequence is placed in a context that is not endogenous to the base adenovirus vector or to a transduced cell. For example, a peptide sequence can be transferred from a protein to another protein, the resulting protein is referred to herein as heterologous protein. A chimeric fiber protein, (e.g., a serotype 5 tail domain and a serotype 35 shaft and knob domain) is considered a "heterologous" to the Ad 5 vector. The term also includes nucleic acids (e.g. coding sequences) from one strain or serotype of adenovirus introduced into a different strain or serotype of adenovirus.

The term "regulatory elements" is intended to include promoters, enhancers, transcription termination signals, polyadenylation sequences, and other expression control sequences. Regulatory elements referred to in the invention include but are not limited to, those which direct expression of nucleic acid sequence only in certain host cells (e.g. tissue specific regulatory sequences).

The term "operably linked" indicates that a polynucleotide sequence (e.g., a coding sequence or gene) is linked to a regulatory element in such a way that the regulatory element sequence controls and regulates the transcription or translation or both of that polynucleotide sequence. The orientation of the regulatory element may vary (eg, be in reverse orientation with respect to the right ITR). The term also includes having an appropriate start signal (e.g., ATG) in front of the polynucleotide sequence to be expressed and maintaining the correct reading frame to permit expression of the polynucleotide sequence under the control of the expression control sequence and production of the desired polypeptide or protein. Regulatory sequences can also include 3' sequences which ensure correct termination (eg. polyadenylation stop signal).

The term "gene therapy" used herein, refers to a method which introduces a segment of exogenous nucleic acid into a cell in such a way that it results in functional modification to the recipient cell by expression of the exogenous nucleic acid. The exogenous nucleic acid is typically therapeutic in that the expression of the encoded protein, polypeptide or RNA corrects cellular dysfunction due to a genetic error or more generally counteracts any undesirable functions which are associated with a genetic or acquired disease. The term "exogenous nucleic acid" refers to DNA or RNA sequences not normally expressed in the treated transformed cell. The term also refers to DNA and RNA sequences which are expressed in a treated transformed cell at a higher, lower or in an otherwise different pattern than in the untreated, nontransformed cell. This non-natural expression can also be termed heterologous expression.

A "gene therapy vector" refers to a vector used for gene therapy. i.e. to introduce the exogenous nucleic acid into a recipient or host cell. The exogenous nucleic acid may be transiently expressed or integrated and stably expressed in the recipient or host cell.

The term "plasmid" as used herein refers to any nucleic acid molecule which replicates independently of the host, maintains a high copy number, and which can be used as a cloning tool.

The term "parallel strand of DNA" and "anti-parallel strand of DNA" refers to as each of the strands of DNA of the double stranded adenovirus. The Figures diagram the location of certain nucleotides on the parallel strand of DNA. The anti-parallel strand of DNA refers to the other of the two strands of DNA which is not depicted in the Figures. The fiber protein is encoded on the anti-parallel strand of DNA. To simplify the vector diagrams, the fiber sequences are shown on the parallel strand even though the gene is located on the anti-parallel strand.

The term "reporter gene" refers to any nucleic acid sequence which encodes a polypeptide or protein which can be readily detected by, for example, a visual, microscopic, immunochemical or enzymatic assay. Preferred reporter genes are those that can be detected by a non-destructive method that does not destroy the treated, transformed cells or tissue.

The term "selection gene" used herein refers to any nucleic acid fragment which encodes a polypeptide or protein whose expression is used to mark a cell as a transformed cell by a given vector.

The term "therapeutic gene" refers herein to a DNA fragment encoding a functional polypeptide, protein or RNA, which when expressed in a host cell provides a therapeutic benefit or desired function to the host cell or to the organ or organism containing the host cell. The therapeutic benefit may result from modification of a function of a native gene in a host or from the additional function provided by the therapeutic protein, polypeptide or RNA.

The term "host tissue" or "host cell" as used herein, refers to a tissue or cell in which a therapeutic gene is to be expressed to modify its function.

It is well-known in the biological arts that certain amino acid substitutions may be made in protein sequences without affecting the function of the protein. Generally, conservative amino acid substitutions or substitutions of similar amino acids are tolerated without affecting protein function. Similar amino acids can be those that are similar in size and/or charge properties, for example, aspartate and glutamate, and isoleucine and valine, are both pairs of similar amino acids. Similarity between amino acid pairs has been assessed in the art in a number of ways. For example, Dayhoff et al. (1978) in *Atlas of Protein Sequence and Structure, Volume* 5, Supplement 3, Chapter 22, pp. 345–352, which is incorporated by reference herein, provides frequency tables for amino acid substitutions which can be employed as a measure of amino acid similarity. Dayhoff et al's frequency tables are based on comparisons of amino acid sequences for proteins having the same function from a variety of evolutionarily different sources. Therefore, any obvious changes in the amino acid sequences (as described above) to the sequences of the invention are already contemplated.

Polypeptides which are "substantially similar" share sequences as noted above except that residue positions which are not identical may differ by conservative amino acid changes. Conservative amino acid substitutions refer to the interchangeability of residues having similar, side chains. For example, a group of amino acids having aliphatic side chains of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; a group of amino acids having sulfur-containing side chains is cysteine and methionine. Preferred conservative amino acids substitution groups include but are not limited to: valine-leucine-isoleucine, phenylalanine-tyrosine, lysine-arginine, alanine-valine, asparagine-glutamine, and aspartate-glutamate. Therefore, polypeptide substitution for "substantially similar" sequences (as described above) to the amino acid sequences described invention are already contemplated.

In order that the invention herein described may be more fully understood, the following description is set forth.

The present invention provides unique gene transfer vehicles which overcome many of the limitations of prior art vectors. The invention describes a first generation adenovirus vectors comprising left and right Ad ITRs, an Ad packaging sequence, a transgene cassette with regulatory elements, and a pair of cassette ITRs flanking the transgene cassette that direct predictable viral genomic rearrangements during viral replication as well as direct the integration of the transgene cassette into the host cell genome.

One predictable rearrangement that occurs during viral replication is the generation of a gutless adenovirus vector (also referred to herein as ΔAd) that comprises right and left Ad ITRs, an Ad packaging sequence, a transgene cassette flanked by cassette ITRs and the gutless vector is devoid of all other immunogenic viral genes.

The potential for site-specific integration is an important characteristic of the novel Ad vectors of the invention. In an embodiment of the invention, integration of the transgene cassette is directed by co-infection with an Ad vector expressing e.g., the rep 78 protein to achieve site-specific integration in the e.g., AAVS1 site on human chromosome 19.

The invention further describes a novel way of targeting these recombinant adenovirus vectors to selected cells by modifying the adenovirus fiber protein that is expressed on the capsid. Changes to both the fiber shaft and the fiber knob domain proved to successfully retarget the Ad vector to a desired cell type. In addition, the G-H loop within the fiber knob domain is identified as a novel site that affect the binding affinity and specificity of the recombinant adenovirus vector. Substitution of peptide sequences into the G-H loop retarget the gutless vector to a desired cell type.

An adenovirus display library has been generated that expresses random peptides within the G-H loop of the fiber protein. This type of a library is used as ligands to screen for adenovirus vectors that bind to desired cell types. One advantage of using an adenovirus display library versus a phage display library is that once adenovirus affinity to a desired cell is identified the targeted adenovirus vector is ready to accept a transgene cassette and can be used to generate a gutless adenovirus vector, for example for use in gene therapy.

The chimeric Ad vectors described below contain a modified fiber protein in the capsid of the adenovirus which renders the vector capable of infecting a desired cell types. Therefore, according to the invention, a gutless chimeric ΔAd-AAV vector can be generated to introduce any transgene(s) into any host cell or tissue which is normally refractory to most commonly used gene therapy viral vectors. In addition, the chimeric ΔAd.AAV vector of the invention, is devoid of adenoviral genes, and contains AAV ITR sequences that flank the transgene cassette, which direct stable transgene integration in the host genome allowing long term expression of the transgene.

The transgene cassette described in the invention may carry a transgene which is either a reporter gene, a selectable gene for in vitro or in vivo selection of transduced cells, or a therapeutic gene. In one embodiment of the invention the reporter trangene can be but is not limited to, Δgalactosidase. Many reporter genes are commonly used in the art, of which any could be carried as a transgene in the Ad.AAV vector of the invention. Other examples of reporter are genes are GFP and alkaline phosphatase.

The following describes an embodiment of the first generation Ad vectors of the invention having a wild-type capsid and a transgene cassette flanked by cassette ITR sequences; (b) fiber protein that is modified to retarget Ad vectors; and (c) the combination of both technologies that enables the production of chimeric ΔAd vector including a modified fiber protein expressed on the capsid which retargets the base vector to a desired cell type for infection and transgene integration.

A. Integrating Ad Hybrid Vectors of the Invention:

It has been shown that inverted repeats (IRs) inserted into the E1 region of AdE1-vectors can mediate predictable genomic rearrangements resulting in a gutless vector genome devoid of all viral genes. A specific embodiment of such IR-mediated rearrangements is the Adeno-AAV, first generation hybrid adenovirus vector containing AAV inverted terminal repeats (ITR) flanking a transgene cassette. The AAV ITRs mediate the formation of a genome similar to that of the ΔAd.IR genome (Steinwaerder et al., 2000 Journal of Virology). ΔAd vectors devoid of all viral genes stably integrate and transduce cultured cells with efficiencies comparable to e.g. rAAV vectors. The Examples demonstrate by Southern blot analysis that the ΔAd vectors integrate randomly into the host genome.

The Ad vectors of the invention comprise a left Ad ITR, an adenovirus packaging sequence located 3' to the Ad ITR; a transgene cassette located 3' to the packaging sequence comprising a polyadenylation signal, a transgene, and a heterologous promoter, and flanked by a pair of cassette ITRs. Adenoviral genes used for replication such as E1, E2, E3, E4 are located 3' to the right cassette ITR and a right Ad ITR is located 3' to the replication genes. The vectors of the invention are particularly suited to treat: genetic disorders, cancers, and infectious diseases (such as HIV, emboli, or malaria). Treatable genetic diseases such as hemophilia A and B; cystic fibrosis; muscular dystrophy, and $\overline{\alpha}_1$ antitrypsin disorder are ideal candidates for genetic disease that can be treated by vectors of the invention. A specific example of a therapeutic gene to combat a genetic disorder is gamma-globin to ameliorate sickle cell anemia.

To aid in the selection of transduced cells and characterize the intergration site of the transgene cassette, an embodiment of the invention includes the addition of a sequence comprising a bacterial for the origin of replication, plus a selectable gene. An embodiment of this is an SNori sequence added to the transgene cassette. This allows the ΔAd to be expressed in human and bacterial cells, therefore allowing selection of the transduced cells and characterization of the integration site in the genome of transduced mammalian cells.

The potential for site-specific integration is an important characteristic of the novel Ad vectors of the invention. In an embodiment of the invention, integration of the ΔAd.AAV is directed by co-infection with Ad AAV expressing the rep 78 protein in 293 cells to achieve site-specific integration in the AAVS1 site on human chromosome 19. For this type of site-specific integration to occur in cells other than 293 cells, E4 ORF6 expression is required. The co-infection of ΔAd.AAV, ΔAd. rep 78, and ΔAd. E4-orf6 allows for site specific integration of the ΔAd.AAV transgene cassette. The ΔAd. rep78 and the ΔAd. E4-orf6 genomes are degraded soon after transduction, thus avoiding potential side effects. Site-specific integration is preferred over random integration, which is seen with rAAV and ΔAd.AAV, in order to reduce the risk of insertional mutagenesis.

Integration of the transgene cassette contained in the adenoviral vectors into chromosomes may be associated with silencing (or blocking) of transgene expression. The silencing of transgenes can be overcome by adding insulator elements to the transgene cassette. For example, HS-4 insulator elements derived from the chicken-globin LCR can function in Ad vectors to shield heterologous promoters from adenoviral enhancers. HS-4 insulators or the *Drosophila* Gypsy gene can also be used to prevent silencing transgenes.

Another embodiment of the invention is to split the transgene cassette into two portions of the transgene each carried in a different recombinant adenoviral vector of the invention. Each portion of the same trangene has an overlapping region of homology. After infection with both vectors, each carrying the different but overlapping portion of the same transgene, homologous recombination event occurs resulting in the reconstitution of the complete transgene which is then expressed. This technique is used to produce hybrid adenoviral vectors that accommodate large inserts including, but not limited to a 13 kb genomic hAAT gene or a 12 kb γglobin LCRγglobin expression cassettes for ameliorating sickle cell anemia (or correcting γ-globin mutations). The formation of the hybrid ΔAd vector genomes, after recombination between two vectors, is more efficient if the overlapping region of homology within the transgene is longer.

An advantage of the present invention is a method to rapidly isolate pure gutless hybrid adenoviral vectors such as ΔAd.AAV or ΔAd.AAV$^{fx}$ vectors. To minimize the contamination of ΔAd with first generation vectors (Ad vectors) a strategy is described in Example I H. It is anticipated that these approaches will yield the same titer of ΔAd vectors, however the contamination with full-length genome vectors will be less. This improved isolation of the vectors is extremely important to avoid toxic side effects after in vivo application.

B. Tropism Modified Adenovirus Vectors:

The Ad vectors of the invention can be modified so that they target a host cell of interest. There are more than 50 human Ad serotypes (Appendix I), including variants with different tissue selectivity or tropism. It is accepted in the art that different Ad serotypes bind to different cellular receptors and use different entry mechanisms. Most recombinant adenovirus vectors use adenovirus serotype 5 as the base vector serotype 5 (Ad5) (Hitt, M. M., et all, 1997, Adv. in Pharmacology 40, 137–205). Ad5 infection is primarily mediated by its fiber protein binding to CAR and secondarily by its penton base protein binding to integrin. Due to the lack of CAR and/or integrin expression on many cell and tissue types, Ad5 mediated gene transfer is inefficient in a number of tissues which are important targets for gene therapy such as endothelia, smooth muscle, skin epithelia, differentiated airway epithelia, brain tissue, peripheral blood cells, or bone marrow. The following describes Ad5 vectors of the invention having a change in infectivity and tropism as a result of altering the fiber protein sequence.

The infectivity of different Ad serotypes is limited to a number of human cell lines. Infectivity studies revealed that Ad5 and Ad3 are particularly suitable for infecting and targeting endothelial or lymphoid cells, whereas Ad9, Ad11 and Ad35 efficiently infected human bone marrow cells. Therefore, the knob domain of the fiber protein of Ad9, Ad11 and Ad35 are excellent candidates for retargeting the Ad5 vector to human bone marrow cells. Other possible serotypes include Ad7.

In the modified fiber protein of the invention the fiber knob domain of the Ad5 fiber has been replaced with another Ad serotype fiber knob domain. An embodiment of the invention is the modified Ad5/35 fiber protein (a recombinant Ad5 vector expressing a modified fiber protein comprising of a fiber tail domain of Ad5 and the fiber shaft and knob domains of Ad35). The Ad5/35 chimeric fiber protein shows a broader spectrum of infection to a subset of CD34+ cells, including those with stem cell activity. The Ad5/11 chimeric fiber protein (a recombinant Ad5 vector expressing a modified fiber protein comprising the fiber tail domain of Ad5 and the fiber shaft and knob domains of Ad11) showed similar tropism.

Figure 3:
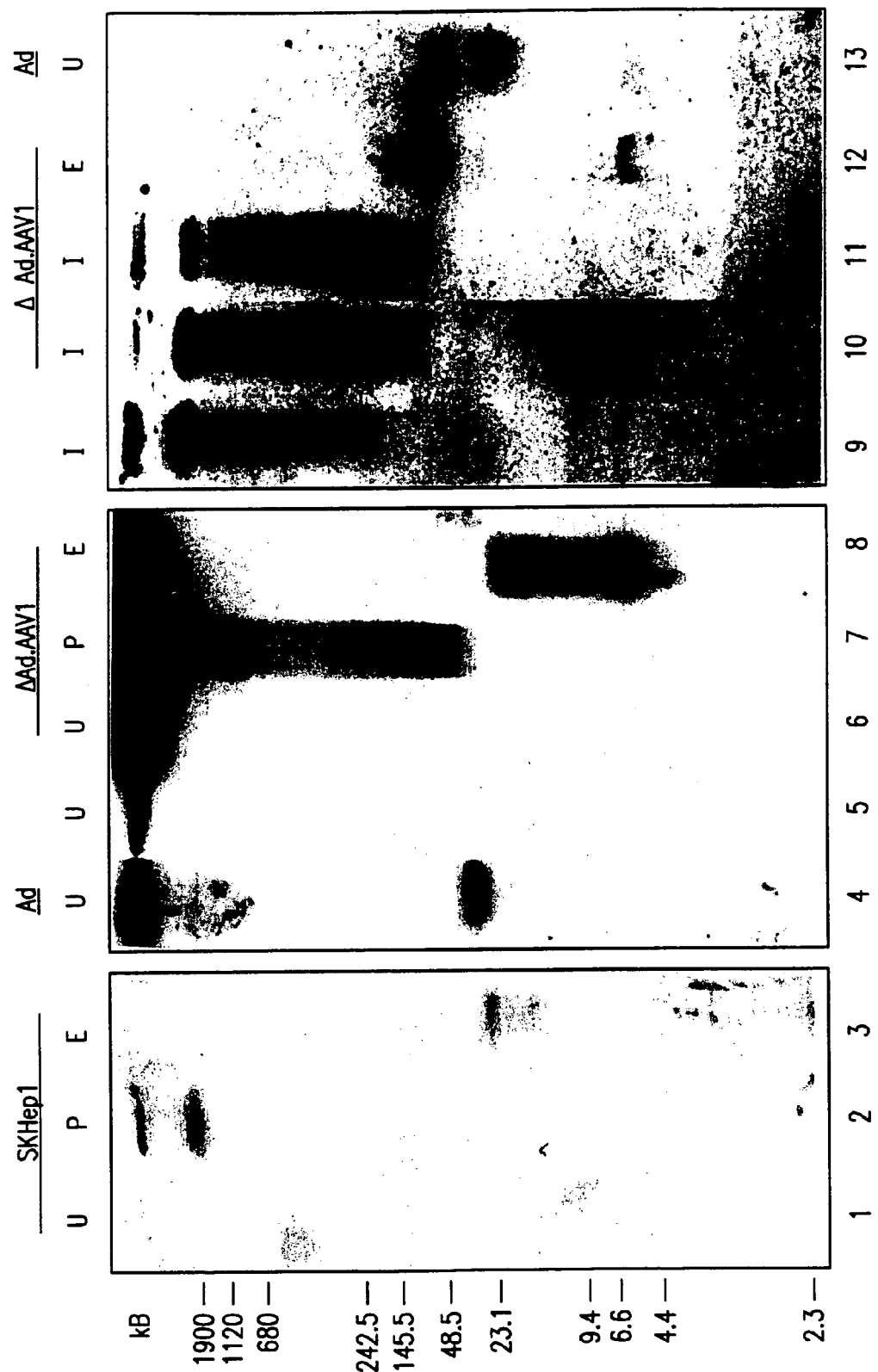
FIG. 3 illustrates analysis of ΔAd.AAV1 genomes after transduction of SKHep1 cells. Pulse field gel eletrophoresis (PFGE). 1×10$^6$ control Sk Hep1 cells (SKHep1) (lanes 1–3, 5, 9). SKHep1 cells from G418 resistant pools (ΔAd.AAV1) (infected with ΔAd.AAV1 and selected for 4 weeks) (lanes 6–8, 10–12), or SKHep1 cells collected at 3 days after infection with 2000 genomes Ad.AAV1 (Ad) lanes 4, 13) are sealed in agarose plaques, lysed in situ and subjected to PFGE with or without prior digestion with restriction endonucleases. Southern Blot is performed with a SEAP specific probe. U=undigested, P=digested with PI-Sce1, I=I-CeuI, E=EcoREI.

In addition to the knob domain modifications, the invention describes the added advantage of modifying both the fiber shaft domain and the fiber knob domain to produce a shortened fiber protein. The length of the fiber shaft domain plays a key role in the host receptors used for viral vector entry into the host cell. To show this Ad5, Ad5/9, and Ad5/35 variants were constructed with long (22β-sheets) and short-shafted (7β-sheets)-shafted fibers. These analyses demonstrated that efficient viral infection involving CAR as the primary receptor for Ad5, Ad5/9 requires a long-shafted fiber protein, whereas the cell entry strategy of Ad5/35 (which binds to an still uncharacterized non-CAR receptor) does not depend on the shaft length (FIG. 3). The modification in both the fiber shaft domain length (between 5>10 β-sheets) and the fiber knob domain (from a different Adserotype than the base vector is a novel mode of altering Ad vector tropism.

To broaden the repertoire of cell types that Ad vectors can infect, a specific binding region, the G-H loop, within the knob domain has been newly identified herein to improve binding affinity and specificity. Alteration within this region will redirect the Ad vector to a desired cell type. For example, the invention describes the G-H loop sequence within the fiber protein knob domain, which can be replaced with heterologous peptide ligand sequences without affecting the functionally important tertiary structure of the Ad fiber knob domain, while changing the binding affinity and specificity of the vector (FIG. 27). This G-H loop region is exposed on the central part of the knob surface and may be strategically a better site for incorporation of heterologous ligands than the peripheral H-I loop (Krasnykh, V. et al., 1998, *J. Virol.*, 72:1844–52.) of the knob C-terminus (Michael, S. I., et al., 1995, *Gene Ther.*, 2:660–8., Wickham, T. J. et al., 1996, *Nat. Biotechnol.*, 14:1570–3.), which are the substitution sites used by others. Therefore, these G-H loop modifications within the fiber knob domain will allow the Ad vector to be redirected to infect a desired cell type, as long as the G-H loop ligand sequence binds to at least one surface protein on the desired cell type. FIG. 27 shows some possible substitutions. Example II J demonstrates that the virion tolerates the insertion of a cycling peptide (12 amino acids) with a constrained secondary structure that allows the exposure on the knob surface. A defined ligand (RGD) can be inserted into the G-H and the H-I loop of an Ad5 capsid that is ablated for CAR, and integrin tropism. Infectivity studies show the potential advantage of this new insertion site.

Use of the Vectors of the Invention for "Gene Therapy"

The liver is the major organ for protein synthesis. Therefore an important goal of gene therapy is to target gene therapy vectors to the liver. To genetically correct many types of mutant proteins hepatocytes need to be infected with gene therapy vectors carrying a corrected transgene. Example II J describes a G-H loop substitution in the knob domain of the fiber protein with both RI and RII+ (of the malaria circumsporozite surface protein) in a short shafted fiber protein which directs the vector to have affinity and specificity to hepatocytes.

Example II K applies a similar protocol to alter the fiber knob domain in the G-H loop region with peptides that target the vector breast cancer cell lines (MDA-MB-435). These novel approaches to redirect vectors described in the invention allow lower doses of the gene therapy vectors to be administered with a higher safety profile.

In example II L a protocol for preparing an adenovirus display library is described that uses the fiber knob protein to display a library of random peptide sequences within the G-H loop. This library of adenoviruses with modified fiber proteins is screened for affinity and specificity for a desired cell type. There are two main advantages of using this adenovirus display library to screen for target peptides that allow binding to a desired cell type over a phage display library system. First, once a ligand peptide is identified that binds to the desired cell type it is already in the vector of choice for gene therapy delivery. The peptide does not need to be engineered into another vector, as is the case for the phage display library vectors. This reduces the steps required to identify a targeted fiber protein for a desired cell type. The second advantage of this method, is that the adenoviruses are able to display multiple copies of the modified fiber protein on their capsid. This allows for dimerization and trimerization of the fiber protein with the host cell receptor. The multimerization of fibers proteins is a realistic, in vivo interaction of the trimeric fiber protein with the host cell receptor. In contrast, phage vectors can only display one fiber peptide sequence on their surface, which significantly limits the ability of interaction with host cell surface receptors.

C. A Chimeric Adenovirus Vector with Selective Tropism:

The chimeric vectors of the invention combine two vectors: an Ad.ITR and a Ad. fx where fx describes a modified fiber protein. A first generation adenovirus vector of serotype 5 is the base vector that carries a transgene cassette flanked by heterologous ITRs. These specific inverted terminal repeat sequences, such as AAV ITRs direct stable integration of the transgene cassette into the host genome as well as control predictable genomic rearrangements that occur during viral replication. This vector can also carry a modified fiber gene (described in Examples II). During replication predictable genomic rearrangements occur which result in the generation of a gutless adenovirus vector (e.g. ΔAd.AAV$^{fx}$) which expresses the modified fiber protein on its capsid. The modified fiber protein allows the gutless vector to be targeted to a selected cell type. The targeted vector is a gutless adenovirus vector devoid of adenoviral genes which can integrate its transgene into the host genome. The transgene cassette can carry reporter, selectable, or therapeutic genes.

In one embodiment of the invention, the gutless targeted ΔAd.AAV$^{fx}$ carries the reporter gene of $\overline{A}$galactosidase ΔAd.AAV$^{fx}$-BG). For easy in vitro selection of human and bacterial cells that are transduced with the hybrid Ad vector, a bacterial sequence for the origin of replication can be added to the hybrid Ad vectors. An example of this is ΔAd.AAV$^{fx}$-Snori, in which a SNori sequence is added into the transgene cassette. This site allows for G418 selection on cells infected with ΔAd.AAV$^{fx}$-SNori. This in vitro selection provides a tool to analyze the site of transgene integration and the flanking chromosomal regions. Fluorescent in situ hybridization (FISH) is an alternative method to confirm vector integration.

An advantage of the ΔAd chimeric vector for gene transfer is the efficient and stable integration of a large transgene cassette up to e.g. 22 kb which is significantly larger than the capacity of retroviral vectors. This is of particular interest for gene therapy. For example, to ameliorate sickle cell anemia ΔAd.AAV$^{fx}$γglobin, an expression transgene cassette with the gamma-globin gene that targets and integrates, can be inserted into bone marrow stem cells for long term expression of the gamma-globin gene.

To achieve site-specific gene integration, rep78 protein is used for transgene integration into the AAVS1 site (described in Example 1D). However, this may silence transgene expression. To prevent the integrated transgene from being silenced by host genomic elements (such as positional effects or downstream enhancers), LCRs or insulator elements are incorporated into the transgene cassette.

The following examples are presented to illustrate the present invention and to assist one of ordinary skill in making and using the same. The examples are not intended in any way to otherwise limit the scope of the invention.

EXAMPLE I

Novel Adenoviral Vector Ad.AAV

A. Integrating ΔAd.AAV Hybrid Vectors Devoid of all Adenoviral Genes.

In vitro and in vivo studies with rAAV indicate that the only requirement for rAAV integration are the AAV ITRs and as yet unknown host cellular factors. It is thought that specific sequences or secondary structures present in AAV ITRs are prone to integration into host chromosomal DNA. In order to combine advantages of adenoviral vectors (high titer, high infectivity, large capacity) and the integration capability of AAV ITRs, AAV vector DNA with AAV ITRs flanking cassettes a secreted human placental alkaline phosphatase (SEAP)-neomycin phosphotransferase (neo) reporter gene cassette (Alexander, I. E., et al. 1996, *Gene Therapy*, 7, 841–850) is incorporated into the E1-region of E1/E3 deleted adenoviral vectors (Ad.AAV1) (FIG. 1, top).

Methods

Production/Characterization of Viral Vectors

Plasmids:

The AAV1 vector cassette containing AAV ITRs and SEAP/neo expression units is obtained by AseI/ScaI digestion of the plasmid pALSAPSN (Alexander, I. E. et al, 1996, *Human Gene Therapy*, 7:841–50). The 4.4 kb AAV vector fragment was cloned via NotI adapter linkers into pXJCL1 (Mirobix, Toronto, Canada) (pAd.AAV1). Another shuttle vector (pAd.AAV1-Δ2ITRs) lacking the AAV ITRs is generated by inserting the 3.7 kb AflII/BsmI fragment of pAL-APSN into pXJCL1. For pAd.AAV1Δ1ITR, a construct is used where a spontaneous deletion in the left AAV ITRs between the A and A' regions has occurred. To create a second hybrid vector (Ad.AAV2), the AAVSNori cassette developed by E. Rutledge is used. AAV vector DNA obtained is from pASNori (Rutledge, E. A., Russell, D. W. 1997. *Journal of Virology* 71:8429–8436) as a 3.4 kb BsaI/ScaI fragment and inserted into the EcoRV site of pXCJL1. As it is generally known for AAV vector plasmids, the AAV ITRs are prone to rearrangements. To minimize deletions in these functional critical regions, all constructs for generation of hybrid vectors are assembled in low copy-number plasmids which are grown in *E. coli* Top10, JC811, or XL1 Bluecells (Stragene, La Jolla, Calif.). Furthermore, after each cloning step or large-scale plasmid amplification, both AAV ITRs are carefully mapped by restriction analysis with enzymes that cut inside or adjacent to the ITRs (BssHII, AhdI, SmaI, BglI, BsmI, AflII, and ScaI).

Adenoviruses:

First-generation viruses with the different transgene cassettes incorporated into the E1 region are generated by recombination of the pΔE1aSpla- or pXCJL1-derived shuttle plasmids and pJM17 (Microbix) in 293 cells as described earlier (Lieber, A., et al., 1996, *J. of Virology*, 70, 8782–8791). For each virus, at least 20 plaques are picked, amplified, and analyzed by restriction digest. Viruses containing two AAV ITDRs tend to rearrange within the ITRs, with other adenoviral sequences, or with adenoviral sequences present in the 293 cell genome. Only plaques from viruses with intact ITRs are amplified, CsCl banded, and titered as described earlier (Kay, M. A., et al. 1995. *Hepatology* 21:815–819; Lieber, A., et al. 1996. *Journal of Virology* 70:8944–8960). All virus preparations tested are negative for RCA and bacterial endotoxin (Lieber, A., et al. 1997. *Journal of Virology* 71:8798–8807). Virus is stored at −80° C. in 10 mM Tris-Cl, pH 7.5–1 mM $MgCl_2$-10% glycerol.

To generate ΔAd.AAV, 293 cells are infected with Ad.AAV1 at an multiplicity of infection (MOI) of 25 and harvested 40 h after infection. Cells are lysed in PBS by 4 cycles of freeze/thawing. Lysates are centrifuged to remove cell debris and digested for 30 min at 37° C. with 500 units/ml DNaseI and 200 μg/ml RNaseA in the presence of 10 mM $MgCl_2$. 5 ml of lysate is layered on a CsCl step gradient (0.5 ml–1.5 $g/cm^3$, 2.5 ml–1.35 $g/cm^3$, 4 ml–1.25 $g/cm^3$) and ultracentrifuged for 2 h at 35,000 rpm (rotor SW41). CsCl fractions are collected by puncturing the tube and are analyzed for viral DNA (Lieber, A., et al. 1996. *Journal of Virology* 70:8944–8960; Steinwaerder, D. S., et al. 1999. *J Virol* 73:9303–13) or subjected to ultracentrifugation at 35,000 rpm for 18 hours in an equilibrium gradient with 1.32 $g/cm^3$ CsCl. The band containing the deleted viruses ΔAd.AAV is clearly separated (0.5 cm distance) from other banded viral particles containing full-length ad.AAV genomes. ΔAd.AAV1 fractions are dialyzed against 10 mM Tris-Cl, pH 7.5–1 mM $MgCl_2$-10% glycerol and stored at −80° C. The genome titer of ΔAd.AAV1 preparations is determined based on quantitative Southern analysis of viral DNA purified from viral particles in comparison to different concentrations of a 4.4 kb AseI/ScaI fragment of pALSAPSN according to a protocol described earlier (Lieber, A., et al., 1996, *J. of Virology*, 70, 8782–8791). In total, the production of $1 \times 10^{13}$ genome-particles of ΔAd.AAV1 requires less than 3 hours of actual work.

Titers routinely obtained are in the range of $3–8 \times 10^{12}$ genomes per ml. Assuming one genome is packaged per capsid, the genome titer equals the particle titer. The level of contaminating Ad.AAV1 is less than 0.1% as determined by Southern analysis, which is consistent with results obtained by plaque assay on 293 cells (fewer than 5 plaques per $10^6$ total genomes). The primers used for sequencing the left and right ITR-vector-junction are 5'GGCGTTACTTAAGCTAGAGCTTATCTG (SEQ ID NO.: 1), and

5'CTCTCTAGTTCTAGCCTCGATCTCAC (SEQ ID NO.:2).

SEQ ID NO: 1

SEQ ID NO: 2

The recombinant AAV virus stock containing the SEAP/neo cassette (AV2/ALSAPSN, [Alexander, I. E. et al, 1996, *Human Gene Therapy*, 7:841–50] used in these studies were obtained from Dusty Miller (FHCRC, Seattle). The stock was free of contaminating replication competent AAV (<50 particles/ml) and wildtype adenovirus (<100 particles/ml). The genome titer of the virus stock was obtained by quantitative Southern Blots as described by Russell et al. (Russell, D. et al. 1994 *Proc. Natl. Acad, Sci. USA* 91:8915–8919).

Electron Microscopy:

For examination of viral particles in the transmission electron microscopy studies, CsCl-purified virions are fixed with glutaraldehyde and stained with uranyl acetate as described previously (Lieber, A., et al. 1996. *Journal of Virology* 70:8944–8960).

Results

During replication of these hybrid vectors in 293 cells, a 5.5 kb genome (ΔAd.AAV1) is efficiently generated and packaged into adenovirus (Ad5) capsids. The ΔAd.AAV1 genome contains the left adenovirus ITR and the packaging signal followed by the AAV-vector cassette and a duplicate of the adenoviral packaging signal and ITR in reverse orientation (FIG. 1, bottom). The hybrid vector is devoid of all viral genes, thus eliminating toxic effects and the elicitation of cellular immune responses. The spontaneous formation of the small hybrid vector genome ΔAd.AAV1 requires the presence of two intact AAV ITRs and does not occur with partly deleted ITRs or oligo-dC and oligo-dG stretches flanking the expression cassette.

Hybrid Vectors Containing Different Transgenes:

To construct a hybrid vector with a transgene that can be detected in situ the SEAP/neo expression unit in Ad.AAV1 is replaced by the *E. coli* β-galactosidase gene. This hybrid vector is named ΔAd.AAV1. During generation of the corresponding plasmid constructs the AAV ITR sequences tend to rearrange and abolish their functional properties. This problem can be circumvented by using low copy number plasmids as cloning vectors grown in bacteria strains depleted for all recombination proteins (e.g. JC811). Furthermore, the intactness of both AAV ITRs after each cloning step can be examined for characteristic endonuclease digestion. Recently, another hybrid vector ΔAd.AAV1Nori has been generated which contains the neo gene under the control of both the simian virus 40 (SV40) early promoter and the transposon 5 (Tn5) promoter for expression in human and bacterial cells, as well as the p15A bacterial replication origin with the direction of the leading strand DNA synthesis opposite that of neo gene transcription. Thus, SNori can be used for, G418 selection of integrated vector in eukaryotic cells as well as for rescue of vector together with flanking host DNA after integration. The recovered plasmids can be propagated in *E. coli* under selection with kanamycin due to the bacterial origin and the neo gene. SNori containing vectors allow a rapid estimation of total integration events based on the number of G418 resistant colonies. Moreover, vector DNA together with flanking chromosomal DNA can be rescued as plasmids from single G418 resistant clones and can be used for sequencing to determine integration junctions. Both hybrid vectors are produced at a titer of about $3 \times 10^{12}$ genomes per ml. The ratio of genome titer to transducing particles for ΔAd.AAVBG is ~200:1 based on β-Gal expression.

Discussion

Figure 2:
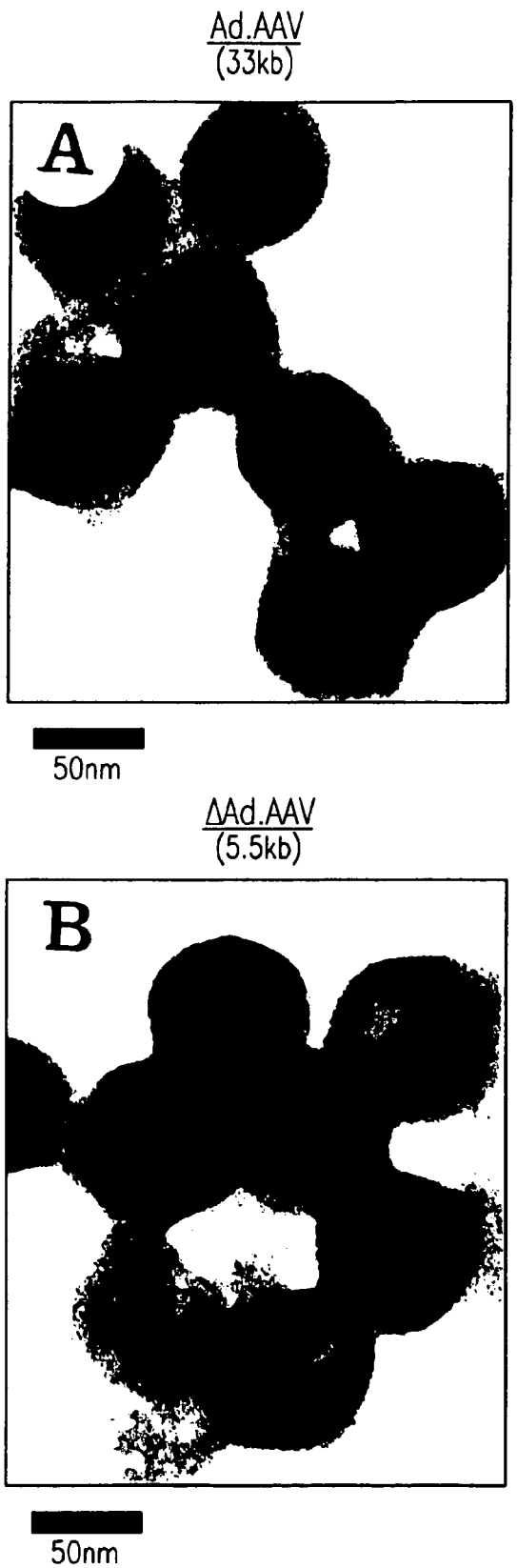
FIGS. 2A and 2B show electron photomicrographs of hybrid virus particles.

ΔAd.AAV1 could spontaneously form during adenovirus replication. Another possible mechanism of ΔAd.AAV1 formation is based on the unique mechanism by which adenovirus replicates its genome (van der Vliet, B., 1995, In w. Doerfler, et al. (eds.) vol. 2 p. 1–31, Springer-Verlag, Berlin) (see FIG. 1). Ad DNA replication is initiated by the TP/pTP (terminal protein) that binds to specific sites within the ITRs on both ends of the linear genome and catalyzes, in complex with Ad pol, the binding of the 5' CTP, the first nucleotide of the daughter strand. DNA synthesis proceeds in a continuous fashion to the other end of the genome (FIG. 1A). Only one of the DNA strands serves as template. One of the replication products is a single-stranded DNA that circularizes through annealing of its self-complementary ITRs. The resulting duplex "panhandle" has the same structure as the termini of the duplex viral genome that allows the binding of pTP and the initiation for synthesis of a complementary strand using the single-stranded "pandhandle" molecule as template (FIG. 1C). In the case of Ad.AAV1, the Ad pol synthesizes the single strand of the adenoviral genome starting from the left Ad ITR until it reaches the second AAV ITR. During synthesis of the second AAV ITR a certain percentage of the single-stranded molecules form a loop hybridizing to the complementary region within the first AAV ITR that was replicated earlier, allowing Ad pol to use the same viral DNA strand to read back towards the left ITR (FIG. 1B). The resulting "panhandle" structure can be resolved in a similar way as a full-length intermediate shown in FIG. 1C, generating a double stranded, linear molecule with the above described structure that can be packaged into Ad virions. The ratio of viral DNA to protein concentration in purified ΔAd.AAV1 particles is comparable to that obtained from Ad.AAV1 particles. This indicates that despite the smaller size, only one ΔAd.AAV1 genome is packaged, resulting in particles with a lighter buoyant density (~1.32 g/cm$^3$). Electron microscopy demonstrates the icosahedral shape of ΔAd.AAV1 particles (FIG. 2). Staining with uranyl acetate causes the central viral cores to appear electron dense. ΔAd.AAV1 virions have only a spotted luminal dark staining as expected with only one 5.5 kb genome being packaged per capsid.

B. In Vitro ΔAd.AAV1 Production:

Characteristics of Deleted adeno-AAV Vectors (ΔAd.AAV):

A number of experiments to clarify the mechanisms of ΔAd.AAV genome formation are carried out. Specifically, the presence of two intact AAV ITRs flanking a reporter gene cassette is required for the effective formation of ΔAd.AAV genomes. This process does not occur with partially deleted ITRs or oligo-dC and oligo-dG stretches flanking the expression cassette. Furthermore, in vitro transduction studies are performed with different genome titers of ΔAd.AAV1, Ad.AAV1, and Ad.AAV1-Δ2ITRs, (lacking the two AAV ITRs) which determine the number of G418 resistant colonies that formed after 4 weeks of selection (Table I).

ΔAd.AAV1 is routinely produced at a high titer ($5 \times 10^{12}$ genomes per ml with $>10^4$ produced genomes per 293 cell) and at a high purity with less than 0.1% contaminating full length Ad.AAV1 genomes by a technique normally used for amplification and purification of recombinant adenovirus.

In Vitro Transduction Studies with Hybrid Vectors on CD34+ Cells and Erythroleukemia Cells:

In order to test whether the hybrid vectors allow for gene transfer into cell types, that have to be targeted for sickle cell therapy, infection/transduction studies are performed using CD34+enriched human bone marrow cells, derived from mobilized peripheral blood and the human erythroleukemia cell line K562 which express ε and γ globin genes.

Methods

Cell Culture:

SKHep1 cells (HTB-52, American Type Culture Collection, Rockville, Md.), an endothelial cell line derived from human liver [Heffelfinger, S. C., et al., 1992, *In vitro Cell Dev. Biol.* 28A, 136-4-142], are grown in high-glucose Dulbecco's modified Eagle medium with 10% fetal calf serum. SKHep1 cells are analyzed for integrated AAV provirus by Southern analysis of genomic DNA using the AAV1 wild type genome obtained from pAAV/Ad (Samulski, R. J., et al. 1989. *Journal of Virology* 63:3822–3928) (gift from David Russell, University of Washington) as a probe. No specific bands are detected in undigested genomic SKHep1 DNA or after digestion with HindIII. For viral infection, confluent cells are incubated with different viral doses for 2 hours, followed by intensive washing. For G418 selection, 24 h after infection with ΔAd.AAV1, SKHep1 cells are trypsinized and plated at different dilutions under G418 selection (900 µg/ml active compound, Boehringer-Mannheim, Germany). G418 containing culture medium is changed every 3 days. The number of colonies with >1 cells is counted after 4 weeks of selection and divided by the number of initially seeded cells. This ratio is used to express the integration frequency of ΔAd.AAV1. Single colones are obtained by limiting dilutions of infected cells in 96 well plates. Colonies are expanded to $1 \times 10^6$ cells in the presence of G418. Immunofluorescence analysis for adenoviral proteins expressed in SKHep1 cells 3 days post-infection is performed as described earlier [Lieber, A., et al., 1996, *J. of Virology*, 70, 8782–8791].

Results 293 cells are infected with the first generation vector Ad.AAV1. During replication of Ad.AAV1, the small ΔAd.AAV1 genome forms spontaneously and is packaged into adenovirus capsid. At 36 hours after infection cells are harvested and virus is released by several cycles of freeze/thawing. The mixture of Ad.AAV1 and ΔAd.AAV1 particles in the cell lysate is then separated by ultracentrifugation in a CsCl step gradient. Due to its lighter buoyant density, the band containing the ΔAd.AAV1 particles is clearly separated (0.8 cm distance) from the band containing full-length virus (Lieber, A., et al. 1999. *J Virol* 73:9314–24). ΔAd.AAV1 is purified further by an additional CsCl equilibrium gradient and is stored in 10 mM Tris pH7.5, 10% glycerol, 1 mM $MgCl_2$ in 80° C. In total, the production of $2 \times 10^{13}$ (genome) particles of ΔAd.AAV1 requires less than 3 hours of work. All functions for ΔAd.AAV1 replication and particle formation are provided from Ad.AAV1 genomes amplified in the same cell. The efficiency of vector production measured on a genome-per-cell-basis is comparable or higher than labor-intensive, newer techniques for rAAV production, which have not yet been proven to be reliable. The estimated ratio of transducing/genome titer for ΔAd.AAV1 is 1:200 (based on SEAP expression at day 3 post-infection), whereas for the average rAAV preparation, it is in the range of $1:10^3$ to $1:10^4$. $1 \times 10^5$ confluent SKHep1 cells are infected with different MOIs of rAAV1 (stock: $1 \times 10^{10}$ genomes per ml), ΔAd.AAV1 (stock: $5 \times 10^{12}$ genomes per ml), Ad.ADAV1 (stock: $1 \times 10^{13}$ genomes per ml), and AdAAV1 2ITR (stock: $9 \times 10^{12}$ genomes per ml), in a volume of 100 ml 24 hours after infection, cells are washed, trypsinized, and plated at different dilutions. G418 is added 24 hours after plating and selection is performed for 4 weeks. G418 resistant colonies contain on average $>5 \times 10^4$ cells (at least 16 cell divisions). A significant number of small colonies visible at 2 weeks post-infection do not survive continued selection, probably due to episomal vector expression. Cells infected with first-generation adenoviruses with MOIs greater than $1 \times 10^4$ develop CPE during the first week of selection. The rAAV titer is not high enough to perform infection studies with MOIs greater than $10^4$. The colony formation is expressed as percentage of the number of colonies after selection to the number of cells initially seeded for selection (Table I).

TABLE I

Formation of G418 resistant colonies after infection with hybrid viruses in comparison with rAAV.

| MOI (genomes per cell) | Formation of G418 resistant colonies in % (SEM) (after 4 weeks of selection) | | | |
|---|---|---|---|---|
| | rAAV1 | Ad.AAV1 | Ad.AAV1 | Ad.AAV1 2ITRs |
| $10^1$ | 0 | 0 | 0 | 0 |
| $10^2$ | 0 | 0 | 0 | 0 |
| $10^3$ | 2.7 (1.6) | 1.3 (1) | 5.4 (3.0) | 0 |
| $10^4$ | 90.8 (7.0) | 48.0 (8.9) | 12.9 (7.2) | 0 |
| $10^5$ | N/A | 93.1 (5.4) | 3.8 (2.1) | 0 |
| $10^6$ | N/A | 100 | 0 | 0 |
| $10^7$ | N/A | 100 | 0 | 0 |

N = 3 (SEM is indicated in parentheses.)

K562 Cells are Infected with Different MOIs of ΔAd.AAVBG ($1-10^8$ Genomes per Cell):

Three days after infection, the total number of viable cells (based on Trypan blue staining) and the percentage of infected cells (based on X-Gal staining) are determined for all MOIs. The results are presented in FIG. 4A.

Initial Integration Studies:

K562 cells are incubated with ΔAd.AAVSNori at an MOI of $2 \times 10^5$ genomes per cell and the colonies that formed after 4 weeks of G418 selection are counted in 96 well plates. G418 resistant colonies contain on average $>5 \times 10^4$ cells which means that the original cell underwent at least 16 cell divisions.

Infection Studies with Ad.AAVBG ($1-10^8$ Genomes per Cell) on CD34+ Cells:

Cell infection on CD34+ are as described for K562 cells. CD34+ cells are cultured in IMDM supplemented with 20% FCS, kit ligand (stem cell factor-SCF) (100 ng/ml), and IL-3 (100 ng/ml). Since a number of reports suggest that specific cytokines like GM-CSF or M-CSF which induce stem cell differentiation can stimulate integrin expression and may therefore affect internalization of Ad5 vectors, infection rates are compared with Ad5 based hybrid vectors on CD34+ cells cultured with and without pre-stimulation with GM-CSF (50 ng/ml) or M-CSF (50 U/ml). The number of infected cells is counted based on X-Gal staining at day 3 after infection. To test for dose-dependent toxicity, viable cells are counted (based on trypan blue exclusion) at day 3 post-infection. Furthermore, whether high viral doses affect the ability of CD34+ cells to differentiate in methyl cellulose colony assays in presence of IL-3 and SCF is analyzed. The results are expressed as viable cells/X-Gal positive cells vs MOI (see FIG. 4B).

Discussion

The above data demonstrate that ΔAd.AAV transduces stably an immortalized human cell line with a low frequency comparable to rAAV, however, transduction rates could be scaled up to 100% by using greater MOIs of ΔAd.AAV1, which is produced at higher titers than rAAV1. In contrast to infection with the first-generation vector, Ad.AAV1, infection with ΔAd.AAV1 is not associated with dose-dependent cytotoxicity because no viral proteins are expressed from these vectors in transduced cells. Furthermore, viral proteins present in the incoming ΔAd.AAV1 particles are not problematic in the dose range use. The comparison of transduction rates of ΔAd.AAV/Ad.AAV1 with the vector lacking AAV ITRs, Ad.AAV-Δ2ITRs, supports the hypothesis that the presence of two intact AAV ITRs is crucial for hybrid vector integration.

The data demonstrate that the leukemia cell line can be infected at ~90% efficiency with Ad5 based hybrid vectors at MOIs $2\times10^5$ genomes per cell without significant toxic side effects. However, this dose is still ~100 times greater than the dose necessary to infect 100% of HeLa cell, hepastoma cells, primary hepatocytes and other cell lines generally considered as permissive for Ad5 vector infection.

Since viral DNA in cells infected with $2\times10^4$ genomes (or 100 transducing particles per cell) should be lost after 7 cell divisions, the presence of G418 resistant cells in the observed colonies suggests that ΔAd.AAVSNori genomes are integrated into or stably associated with the host genome. Based on the number of G418 resistant colonies one out of 25,000 ΔAd.AAVSNori genomes integrates stably into K562 cells. This is in agreement with the results obtained earlier with ΔAd.AAV1 in SK Hep1 cells.

The maximal dose used for infection of CD34+ cells ($1\times10^8$) results in X-Gal staining of only ~10% of cells independently of GM-CSF/M-CSF. This demonstrates the obvious inability of Ad5 to infect CD34+ cells and is probably caused by the absence of specific receptors and/or integrins on the cell surface. CD34+ cells tolerate a large range of viral doses ($1-10^7$) without obvious effects on cell viability and total cell number. This is not surprising because in order to develop toxic side effects adenovirus has to enter the cell and express viral genes. Hybrid vectors can be produced at titers of $5\times10^{12}$ genomes per ml. Thus, the maximal MOI that can be used for infection (of $10^4$ cells) is $\sim 5\times10^8$ (in 100 µl storage buffer). Based on the infection studies with ΔAd.AAVBG this dose may not be sufficient to efficiently transduce CD34+ cells and to obtain an appreciable number of G418 resistant colonies.

C. In Vivo Properties of ΔAd.AAV1:

Viral DNA is labeled with BrdU during virus amplification to investigate cellular/nuclear vector uptake in situ. For transduction studies, confluent SKHep1 cells (a human endothelial cell line) are infected with 2000 genomes ΔAd.AAV1 or Ad.AAV1 per cell. BrdU tagged viral DNA is detected in 100% of nuclei at 3 hours post-infection for both viruses indicating efficient cellular and nuclear uptake of hybrid virus DNA.

Results

The ΔAd.AAV1 vector transduces a cell in vitro forming G418 resistant colonies with an efficiency of 17 or 58%, after infection with an MOI of $1\times10^3$ or $1\times10^4$ genomes per cell, respectively. Approximately $2\times10^4$ ΔAd.AAV1 genomes are required to yield one stable transfectant. Since all stable colonies contain integrated ΔAd.AAV1 vector DNA, this number reflects the minimal integration frequency of ΔAd.AAV1 in SKHep1 cells which is comparable with that from rAAV (Rutledge, E. A. et al., 1997, *Journal of Virology*, 71:8429–36). The number of G418 resistant colonies does not necessarily represent the total frequency of integration events because not all integrated copies express neomycin phosphotransferase, due to chromosomal position effects or incomplete integration.

The absence of adenoviral gene products in ΔAd.AAV1 transduced cells at day 3 post-infection is demonstrated by immunofluorescence with antibodies to the major late proteins (hexon, fiber) and early proteins (DBP.E4-orf6). Expressed adenoviral proteins are detected only in cells infected with Ad.AAV1. The fact that cells infected with ≠Ad.AAV1 do not express potentially cytotoxic adenoviral proteins is important.

While an MOI of $1\times10^4$ genomes per cell of the first generation vector Ad.AAV1 induce cytopathic effects in SKHep1 cells at day 3 p.i., no toxic side effects are observed when SKHep1 cells are infected with ΔAd.AAV1 at a dose of up to $1\times10^8$ genomes per cell. Since the transduction efficiency is clearly dose dependent, ΔAd.AAV1 (which can be produced at titers of $>5\times10^{12}$ genomes/ml) is able to stably transduce Ad5 permissive cell lines or tissues with a 100% efficiency without associated toxicity.

Southern analysis indicates that ΔAd.AAV1 integrates randomly as head-to-tail tandem repeats into the host cell genome via the right AAV ITR, whereas the other junction with the chromosomal DNA is variable and occurs somewhere within the transgene cassette. In order to confirm the integrated status of ΔAd.AAV1 DNA, high-molecular-weight chromosomal DNA is separated by pulse field gel electrophoresis (PFGE), followed by Southern analysis with a SEAP specific probe (FIG. 3). Undigested DNA from control SKHep1 cells give an endogenous SEAP signal that co-migrates with chromosomal DNA just below the well (lanes 1 and 5). No high-molecular weight episomal forms of ΔAd.AAV1 DNA are detected, whereas a distinct 35 kb band is visible in DNA from SKHep1 cells isolated 3 days after infection with first generation adenovirus, Ad.AAV1 (lanes 4 and 13). Digestion with EcoRI reveals the 4.4 kb fragment, which is specific for integrated tandem copies of the AAV cassette (lanes 8 and 12). To eliminate the possibility that chromosomal DNA is trapped in the well, DNA samples are digested with intron-encoded endonucleases PI-Sce1 or I-CeuI (Gibco-BRL, Grand Island, N.Y.) with a sequence specificity or more than 11 bp or 9 bp respectively. Digestion with PI-SceI yields a >2 mb endogenous SEAP signal in SKHep1 cells (lane 2) and an additional signal in the range of ~1 mb in G418 resistant colonies transduced with ΔAd.AAV1 (lane 7). I-CeuI digestion results in a smear between 250–1000 kb in ΔAd.AAV1 transduced SKHep1-cells (lanes 10, 11) indicating random integration, whereas a high-molecular weight band specific for the endogenous SEAP gene is observed in control SKHep1 cells (lane 9).

One day after intraportal infusion of $1\times10^{12}$ ΔAd.AAV1 genomes in C57B1/6 mice, BrdU labeled vector genomes can be detected in 85% hepatocytes (Lieber, A., et al. 1999. *J Virol* 73:9314–24). Hepatocellular DNA analysis performed at 2 months post-infusion reveals ΔAd.AAV1 DNA integrated with an average of 0.5 copies per cell into the mouse genome (Lieber, A., et al. 1999. *J Virol* 73:9314–24). To assess potential side effects of intraportal ΔAd.AAV1 infusion, serum glutamic pyruvic transaminase (SGPT), a sensitive marker for hepatocellular injury, is measured for 7 consecutive days post-infusion in combination with histological analysis of liver sections. No significant elevation in SGPT levels, or histological abnormalities are detected after intraportal infusion of $1\times10^{12}$ or $1\times10^{13}$ ΔAd.AAV1 genomes, whereas infusion of the same dose of full-length Ad.AAV1 vector is associated with severe hepatoxicity or fatal outcome. This suggests that the dose of ΔAd.AAV1 administered to mice can be increased to obtain higher transduction efficiencies in vivo without adverse side effects, which is not possible for first generation adenoviruses. Importantly, ΔAd.AAV1 transduced quiescent hepatocytes in vivo, which suggests that integration of hybrid vector DNA may not require cell proliferation. Recently, more detailed in vivo transduction studies with Ad.AAV1 and ΔAd.AAV1 have been performed in Balb/c mice to study whether the absence of adenoviral gene expression in cells infected with ΔAd.AAV1 can avoid an anti-viral immune response and can prolong vector persistence. In this mouse strain, vector DNA is cleared from the liver at 4–6 weeks after infusion with first generation adenoviruses, mostly due to a CTL response against viral proteins produced in transduced cells. Vector DNA is analyzed by genomic Southern Blot of hepatic DNA at 12 weeks after infusion of 1×10$^{12}$ genomes Ad.AAV1 or ΔAd.AAV1. At this time point, no vector specific signal is detectable in hepatic DNA from mice infused with the first generation vector Ad.AAV1, while ~0.3 copies of ΔAd.AAV1 genomes per cell are present in livers of mice that received the hybrid vector, again indicating the superior in vivo properties of the hybrid vector.

D. Effects of Rep Coexpression on ΔAd.AAV1 Integration

Rep Expression after Plasmid Transfection:

In order to test whether Rep expression enhances site-specific integration of ΔAd.AAV1 in human cells, a series of Rep expression plasmids are constructed.

Methods

The Rep ORF 68/78 (nt 285–2313) including the internal p19 and p40 promoters is obtained from pAAV/Ad (Samulski, R. J. et al., 1991, In B. N. Fields, et al. (eds.), *Fields Virology*, vol. 2 Lippincott-Raven Publisher, Philadelphia) by digestion with BsaI/BsrI. This fragment deleted for the AAV p5 promoter is cloned via adapter linkers under RSV or PGK promoter in front of the bovine growth hormone polyadenylation signal (bPA) into pAd.RSV or pAd.PGK (Lieber, A., and Kay, M. A., 1996, *J. of Virology*, 70, 3153–3158; Lieber, A., et al., 1995, *Human Gene Therapy*, 6, 5–11) correspondingly.

Results

The resulting plasmids (pRSVrep, pPGKrep) are transfected into 293 cells or SKHep1 cells, most of the Rep proteins expressed from the heterologous promoters (RSV or PGK) are Rep 68 and Rep 78, while transfection of the rep gene under aP5 promoter (pAAV/Ad) results in predominant Rep 52/40 expression. Thus, transfection of pRSVrep and pPGKrep is more pronounced suggesting a strong transactivation of AAV promoters by E1a which is produced in 293 cells. This result indicates that minimum expression of rep proteins is necessary to avoid interference with adenovirus replication.

Rep-Mediated Site-Specific Integration of ΔAd.AAV1.

The potential for site-specific integration is an important characteristic of the novel Ad.AAV vectors of the invention. In an embodiment of the invention, integration of the ΔAd.AAV is directed by co-infection with Ad AAV expressing the rep 78 protein to achieve site-specific integration in the AAVS1 site on human chromosome 19. For this type of site-specific integration to occur in cells other than 293 cells, E4 ORF6 expression is required. The co-infection of ΔAd.AAV, ΔAd. rep 78, and ΔAd. E4-orf6 allows for site specific integration of the ΔAd.AAV transgene cassette. The ΔAd. rep78 and the ΔAd. E4-orf6 genomes are degraded soon after transduction, thus avoiding potential side effects. Site-specific integration is preferred over random integration, which is seen with rAAV and ΔAd.AAV, in order to reduce the risk of insertional mutagenesis.

Figure 5:
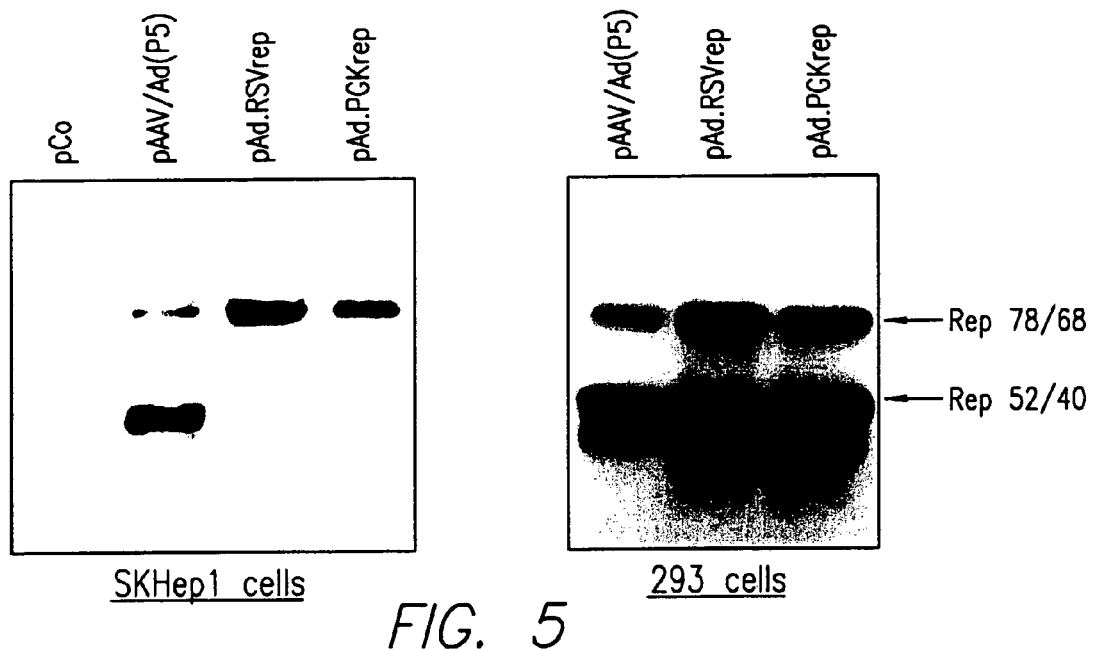
FIG. 5 shows Rep expression in SKHep1 and 293 cells after plasmid transfection. 5×10$^5$ cells are transfected with pAAV/Ad, pRSVrep, or pPGKrep by Ca-phosphate co-precipitation. Three days after transfection, cells are harvested. Lysates are separated on a 10% PA gel, followed by Western Blot with Rep specific antibodies (03-65169), American Research Products), and developed with ECL (Amersham)
Figure 6:
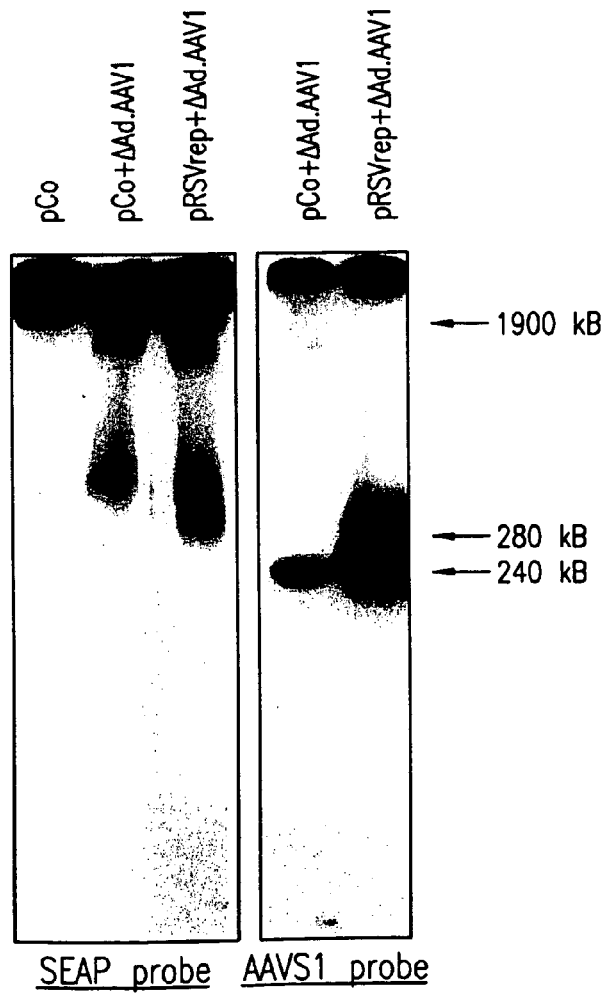
FIG. 6 shows detection of vector integration into AAVS1 by PFGE.

A preliminary test can be performed to confirm the functional activity of Rep 68/78 expressed from pRSVrep to mediate site-specific integration of ΔAd.AAV1 (FIGS. 5 and 6). Human SKHep1 cells are transfected with pRSVrep or control plasmid (pRSVbGal (Lieber, A., et al., 1995, *Human Gene Therapy*, 6, 5–11) (transfection efficiency was ~20%), followed by infection with ΔAd.AAV (2000 genomes per cell). Three days after infection, cells are trypsinized, embedded in agarose, lysed in situ, digested with I-CeuI (an intron-encoded endonuclease with a recognition sequence of more than 10 nt), subjected to pulse file gel electrophoresis in 1% agarose gel, and analyzed by Southern Blot. Hybridization with a probe covering the AAVS1 integration site (1.7 kb EcoRI/BamHI fragment from the chromosome 19 locus (Samulski, R. J. et al., 1991, In B. N. Fields, et al. (eds.), *Fields Virology*, vol. 2 Lippincott-Raven Publisher, Philadelphia)) reveals an AAVS1-specific band (~240 kb) in I-CeuI digested DNA from cells after control plasmid transfection (pCo)+ΔAd.AAV1 infection. An additional signal in the range of 280 kb appears in rep expressing cells infected with ΔAd.AAV1 (pRSVrep+VAd.AAV1) indicating a site-specific insertion into the AAVS1 site in a certain percentage of cells. The presence of vector DNA in this 280 kb band is confirmed by rehybridization of the same filter with a transgene (SEAP) specific probe. Randomly integrated ΔAd.AAV1 vector appears as a diffuse SEAP signal in the range 280–680 kb (pCo+ΔAd.AAV1, pRSVrep+ ΔAd.AAV1). The specific ~1.9 mb band on blots hybridized with the SEAP probe represents an I-CeuI fragment containing the endogenous human SEAP gene.

Figure 7:
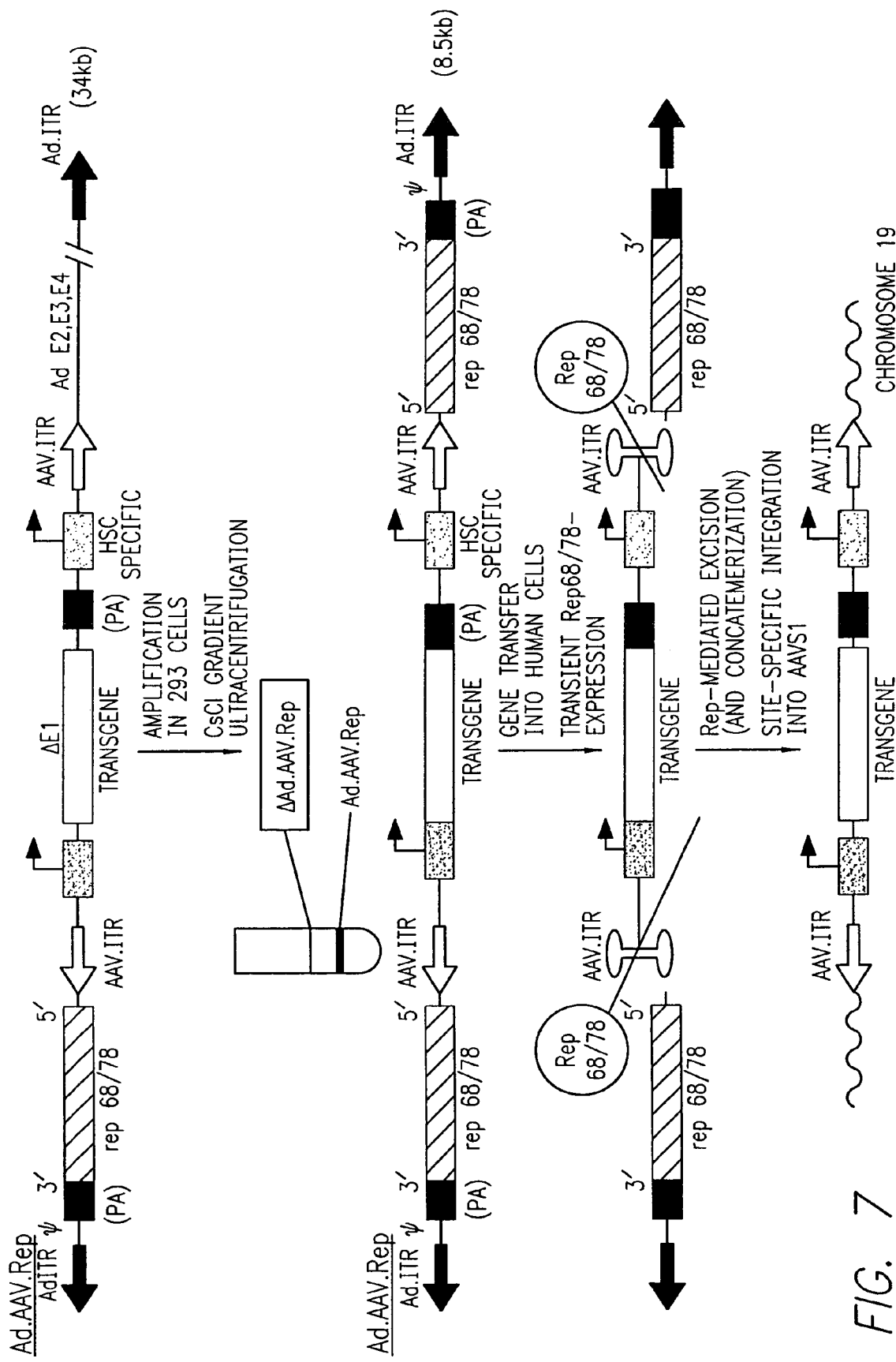
FIG. 7 shows strategy for creating an ΔAd.AAV hybrid vector capable of site-specific integration. Arrows indicate promoters, (PA)=polyadenylation signal. Ψ=adenoviral packaging signal.

Incorporation Rep 68/78 function into hybrid vectors to stimulate site-specific integration Rep overexpression inhibits adenovirus DNA replication, prohibiting the generation of rep expressing Ad vectors using conventional strategies. To solve this problem, significant Rep 68/78 expression from the hybrid vector in virus producer (293) cells must be prevented while maintaining transient Rep expression in target cells (HSC) to mediate site-specific integration. Our hypothesis is that the specific structure of the ΔAd.AAV hybrid virus can be used to bring the rep gene 68/78 into a transcriptionally active position under control of a HSC specific promoter only at late stages of virus replication in 293 cells. This will allow amplification of the hybrid vector in 293 cells, generating high titer virus which activates the incorporated Rep 68/78 functions only in HSC. The general outline of our strategy to produce Rep expressing hybrid vectors is illustrated in FIG. 7. The rep/transgene cassette is assembled based on the left-hand shuttle plasmid used for recombinant adenovirus production. The gene encoding Rep 68/78 is cloned in 3'□5' orientation in front of a transgene expression cassette flanked by AAV ITRs. Between the transgene cassette and the right AAV ITR an HSC-specific promoter is inserted with direction towards the adenoviral E2, E3, and E4 genes. The recombinant genome is produced by recombination in *E. coli* and transfection into 293 cells generates virus (Ad.AAV-rep). The specific structure of ΔAd.AAV with duplicated sequences flanking the AV ITRs is used to bring the rep gene into a transcriptionally active position under control of a HSC specific promoter only during late stages of viral DNA replication in 293 cells. During amplification of Ad.AAV-rep, the smaller genome ΔAd.AAV-rep is formed and packaged into particles, which can be separated by ultracentrifugation in CsCl gradients. The specific structure of ΔAd.AAV-rep brings the rep gene into 5'↔3' orientation in relation to the HSC specific promoter, allowing rep transcription in target cells. After transduction of HSC with purified ΔAd.AAV-rep particles, rep expression is activated and mediates rescue of the AAV-ITR/transgene cassette from the adenoviral vector backbone and site-specific integration. The hypothesis is that Rep-mediated integration into AAVS1 occurs via the right or both AAV/ITRs causing the rep gene to become separated from the hepatocyte-specific promoter once the vector is integrated (FIG. 7). Therefore, rep expression should be only transient without critical cytotoxic side effects on the host cell.

Promoters that can Regulate Rep Expression:

Potential candidate promoters to drive rep expression with high specificity for HSC and minimal activity in 293 cells are the 454 nt CD34 promoter (Krause, D. S., et al., 1997, *Experimental Hemotology*, 25, 1051–1061; Yamaguchia, Y. et al., 1997, *Biochimica et Biophysica Acta.*, 1350:141–6), the 300 nt HS 40 enhancer (Chen, H. L., et al., 1997, *Nucleic Acids Res.* 25, 2917–2922) or a 3 kb CD34 enhancer (May, G. et al., 1995, *EMBO J.*, 14:564–74) in combination with an initiator, or the HIV LTR. An optimal promoter is selected based on studies of transient reporter gene expression after plasmid transfection in 293 cells and hepatocytes. All promoters to be tested are cloned in front of the human $\alpha_1$-antitrypsin (hAAT)-bovine growth hormone polyadenylation signal (bPA) into the adenoviral shuttle plasmid pCD2 (pAd.-hAAT). Promoter activity can be tested in transient plasmid transfection assays in CD34+ and 293 cells. The promoter with the highest hAAT levels in CD34+ or K562 cells and the lowest hAAT expression in 293 cells is selected for further studies. If high background expression in 293 cells from these promoters is seen, insulators to shield HSC-specific promoters from the E1a enhancer which is still present in Ad shuttle plasmids can be utilized.

Rep Genes:

The large Rep 68/78 proteins are sufficient to mediate rescue and site-specific integration. Unregulated Rep 52 and Rep 40 expression from the AAV p19 promoter located within the ORF of Rep 68 and 78 must be prevented because production of these smaller Rep proteins in 293 cells will affect cell viability and adenoviral DNA synthesis. To do this, constructs obtained from Surosky et al., containing a mutated Rep 52/40 start codon to express Rep 68 and 78 individually under CMV promoter can be used. The 293 cells transiently expressing Rep68 or Rep 78 from these constructs can be coinfected with $\Delta$Ad.AAV1 (infection 24 hours after pCMVRep transfection, MOI $2 \times 10^5$ genomes/cell). Three days after $\Delta$Ad.AAV1 infection, cellular DNA is analyzed for AAVS1-specific integration events by PCR and PFGE as described earlier. Efficient Rep mediated excision of the AAV cassette and site-specific integration without flanking adenoviral sequences are expected and the plasmids pCMVRep68 or pCMVRep78 can be used as a source for the corresponding rep genes and clone them into hybrid vectors.

Vectors:

The rep/transgene cassette can be assembled based on pXCJL (Microbix, Toronto). A set of control hybrid vectors can be generated with the AAV-ITR-transgene cassette only without the rep gene. The recombinant Ad.AAV-rep genome can be generated by recombination of the left hand shuttle plasmids with pCD1, a pBHG10 (Microbix, Toronto) derivative, which contains the Ad5 genome deleted for the E1/E3 regions in recA+ *E. coli* (Chartier, C., et al., 1996, *J. of Virology*, 70, 4805–4810). Compared to the standard technique based on plasmid recombination in 293 cells, this approach has the advantage that plaques with recombinant virus appear 3 times faster and the production of illegitimate recombinants is minimized. This allows efficient viral DNA amplification and packaging to occur before Rep expression reaches levels that are potentially inhibitory for adenoviral replication. The critical variables in maximizing the output of the vector deleted for all adenoviral viral genes are the initial multiplicity of infection and the time of harvesting. These parameters can be optimized for production of $\Delta$Ad.AAV-rep hybrid vectors. A number of $\Delta$Ad.AAV vectors can be constructed incorporating rep gene. Cryptic promoter and enhancer elements present in the 5'-342 nt of the adenoviral genome can interfere with transgene expression from the heterologous promoters. This is crucial for the strategy to avoid rep expression from $\Delta$Ad.AAV-rep genomes in 293 cells. To ensure efficient transgene expression, insulator fragments such as the chicken beta-globin insulator can be used with a selected promoter, constitutive or inducible.

Rep Protein Co-Packaging:

As an alternative to producing hybrid vectors containing the rep 68/78 gene, studies are designed to see whether Rep protein can be co-packaged into $\Delta$Ad.AAV capsids and whether these co-packaged Rep molecules are sufficient to mediate rescue and site-specific integration of the AAV-ITR-transgene cassette. Our hypothesis is that the Rep 68/78 binds to the Rep binding site (RBS) present in double-stranded $\Delta$Ad.AAV genome and that this complex is co-packaged into adenoviral capsids which are spacious enough to accommodate extra proteins. Based on protein/DNA ratio analysis performed previously in purified particles that only one 5.5 kb $\Delta$Ad.AAV1 genome is packaged per capsid. This is confirmed by electron-microscopy of $\Delta$Ad.AAV1 particles, which reveals only spotted electron-dense staining associated with viral cores and extended free luminal space (see FIG. 2).

293 cells are transfected with plasmids expressing Rep 68/78 under the CMV promoter and the kinetics of rep expression is determined by Western Blot with cell lysates collected at different time points after transfection. Next, these 293 cells are infected with Ad.AAV (MOI 1, 10, 100 pfu/cell) at specific time points after transfection of Rep plasmids depending on the Rep expression kinetics: (e.g. 3, 6, 12, 24 . . . hours after transfection). It is important to time Ad.AAV infection exactly because viral DNA replication must be taking place or finished before Rep production reaches peak levels. In general, adenovirus DNA replication in 293 cells (infected with MOI 10) is maximal at 18 hours post-infection, followed by production of structural proteins, packaging of viral genomes, and breakdown of cellular membrane structures (which is concluded ~36–48 h p.i.) (Shenk, T., 1996, In B. N. Fields, et al. (eds.), *Fields Virology*, vol. 2 Lippincott-Raven Publisher, Philadelphia; van der Vliet, B., 1995, In w. Doerfler, et al. (eds.) vol. 2 p. 1–31, Springer-Verlag, Berlin). Viruses are collected 48 h after infection and banded by CsCl ultracentrifugation. Viral material from purified bands corresponding to $\Delta$Ad.AAV is lysed, DNAse-treated (to liberate DNA associate Rep) and subjected to immunoprecipitation-Western Blot with Rep specific antibodies to detect co-packaged Rep. Based on theoretical calculations assuming that two Rep molecules bind per Ad genome, ~1–10 np Rep proteins is expected from Lysates of $10^{10}$ particles, which is within the range of detectability by Western Blot. Alternatively, co-packaged Rep may be detected based on its functional activity to mediate rescue and site-specific integration of the AAVITR transgene cassette. To test whether functional Rep protein is co-packaged into hybrid vector particles, CsCl purified $\Delta$Ad.AAV1 particles generated in 293 cells co-expressing Rep after Ad/AAV1 infection ($\Delta$Ad.AAV1+Rep) can be used for transduction studies. Three days after $\Delta$Ad.AAV1+Rep infection of the human cell line K562, cellular DNA is analyzed for AAVS1-specific integration events by PCR and PFGE. If efficient Rep-mediated site-specific integration of excised AAV cassettes is successful, then other ΔAd.AAV+ Rep hybrid vectors with β-Gal and SNori as transgenes can be produced.

Integration Studies with Rep Vectors in Erythroid Cells:

The hypotheses behind the rational of a rep-expressing hybrid vector (ΔAd.AAV-rep) are: (1) transient Rep co-expression from ΔAd.AAV-rep vectors can enhance site-specific vector integration in human cells and (2) integration occurs via the AAV ITR(s) without the rep gene, which is placed outside the AAV cassette, thus eliminating rep expression upon vector integration. To test hypothesis 1, transduction frequencies of ΔAd.AAV/rep versus ΔAd.AAV vectors can be compared based on the formation of G418 resistant colonies and quantify site-specific integration events at different time points after infection of human and mouse cells by PFGE and PCR. To test hypothesis 2, the structure of integrated vector in transduced cell populations and single clones can be delineated by Southern analysis and by sequencing of vector/chromosomal DNA junctions. These studies can be performed with ΔAd.AAV-rep, ΔAd.AAV, and ΔAd.AAV+Rep (copackaged protein) in human K562 or HEL (for AAVS1 integration) and mouse MEL cell lines.

Cells infected with ΔAd.AAV-SNori, ΔAd.AAV-SNori+Rep or ΔAd.AAV-Snori-rep can be subjected to G418 selection. The number of G418 resistant colonies determined after 4 weeks of selection in relation to the number of initially infected cells. The selection process for colonies that did not survive continued selection due to potential rep-mediated cytotoxcicity or episomal vector expression can be monitored. If rep expression from ΔAd.AAV-SNori rep does not affect cell viability and proliferation, then more G418 resistant colonies should appear in ΔAd.AAV-SNori-rep and ΔAd.AAV-Snori+Rep. The structure of integrated vector can be determined by Southern Blot and sequencing of integration junctions.

To uncover a potential selection bias against rep producing cells after transduction with ΔAd.AAV/rep, site-specific and random vector integration events can be quantitated in cellular DNA isolated from cell populations at different time points after infection (e.g. 0.5, 1, 3, 7, 14 days). To do this, the techniques based on PFGE-Southern can be utilized. It is expected that the signal(s) for AAVS1-specific integration in ΔAd.AAV/rep infected human cells increases during the first days after infection and then remains constant over time.

In a separate study, the integration status of vector DNA (analyzed by PFGE or PCR) and the number of integrated copies (analyzed by Southern Blot) with the expression level of β-galactosidase in single clones transduced with β-Gal hybrid vectors (ΔAd.AAV-BG, ΔAd.AAV-BG+Rep, or ΔAd.AAV-BG-rep) can be correlated. Together with data obtained in the studies described in the Specification, this allows assessment of whether transcriptional silencing is associated with site-specific vector integration into the AAVS1 site.

It is not clear a priori whether the specific Rep function for vector rescue, concatemerization, and integration can efficiently occur in non-S-phase or non-dividing cells. To test whether ΔAd.AAV$^{fx}$, ΔAd.AAV or ΔAd.AAV-rep/+Rep vectors can integrate into non-dividing cells, transduction studies in cell cycle arrested cell cultures can be performed as described earlier.

Discussion

The establishment of stable cell lines expressing Rep 68/78 at detectable levels is not possible, which is probably due to rep mediated cytotoxicity. Therefore, it is not possible to perform long-term transduction studies (e.g. G418 selection or studies in single clones) in combination with ectopic rep expression. Moreover, due to the inhibitory effect of rep on adenovirus replication, it is currently not possible to generate adenoviral vectors expressing rep under the RSV or PGK promoter.

Taken together, this indicates that co-expressed Rep may stimulate site-specific transgene integration.

E. A Detailed Study of Transduction/Integration of Hybrid Vectors in Erythroid Cell Lines:

In order to improve transduction and integration frequencies of the hybrid vectors into erythroid cell lines, a detailed study comparing various hybrid vectors have to be carried out as described below. The transduction studies are performed in K562 cells which is considered to be an adequate model to study gene transfer vehicles into erythroid cells (Floch, V., et al., 1997, *Blood Cells, Mol. and Diseases*. 23, 69–87). The optimal vectors should be able to integrate into the cellular genome with a high frequency, determined by Pulse field gel electrophoresis (PFGE) and Southern blot as described in Example 4. In addition, the results from the following studies will serve to evaluate whether a given hybrid vector needs to be modified for site-specific integration in the host genome.

Sequencing of Integration Junctions:

The ultimate proof for vector integration is the sequencing of junctions between SNori vector DNA and chromosomal DNA. Furthermore, this clarifies the question whether the AAV ITRs represent the substrate for integration. Specifically, DNA from clones with known ΔAd.AAVSNori integration structure (analyzed by Southern Blot) digested with EcoRI, which does not cut within the SNori cassette. The resulting fragments are circularized and transformed into a specific *E. coli* strain (according to the protocol described by Rutledge and Russell (Rutledge, E. A. et al., 1997, *Journal of Virology*, 71:8429–36)). Kanamycin resistant bacterial clones should contain the integrated SNori cassette. Flanking chromosomal DNA in rescued plasmids can be sequenced with primers specific to the transgene.

To confirm vector integration in a small number of transduced cells, genomic DNA is extracted and digested with EcoRI. EcoRI fragments are ligated to linkers containing a specific primer binding site and are then digested with NotI, religated and propagated in *E. coli*. Plasmid DNA from a representative number of bacterial clones is sequenced to determine the vector/chromosomal DNA junctions.

Dose Dependent Toxicity:

In order to test that the transduction frequence is dose-dependent and ΔAd.AAV vectors, which are devoid of all adenoviral genes, could be used to infect cells at higher doses with less cytotoxicity than first generation adenovirus, K562 cells are infected with different MOIs ($1-10^8$) of ΔAd.AAVBG and the first generation vector Ad.AAVBG (which contains the same β-Gal expression cassette). At day 4 post-infection, the total number of cells, the percentage of viable cells (based on trypan blue exclusion) and the percentage of X-Gal positive cells are counted. A fraction of infected cells are quantified for β-Gal expression using the Galacto-Light kit. The level of transgene expression is expected to be comparable between the two vectors. K562 cells are predicted to tolerate higher doses of ΔAd.AAVBG better than Ad.AAVBG which express viral genes.

Figure 8B:
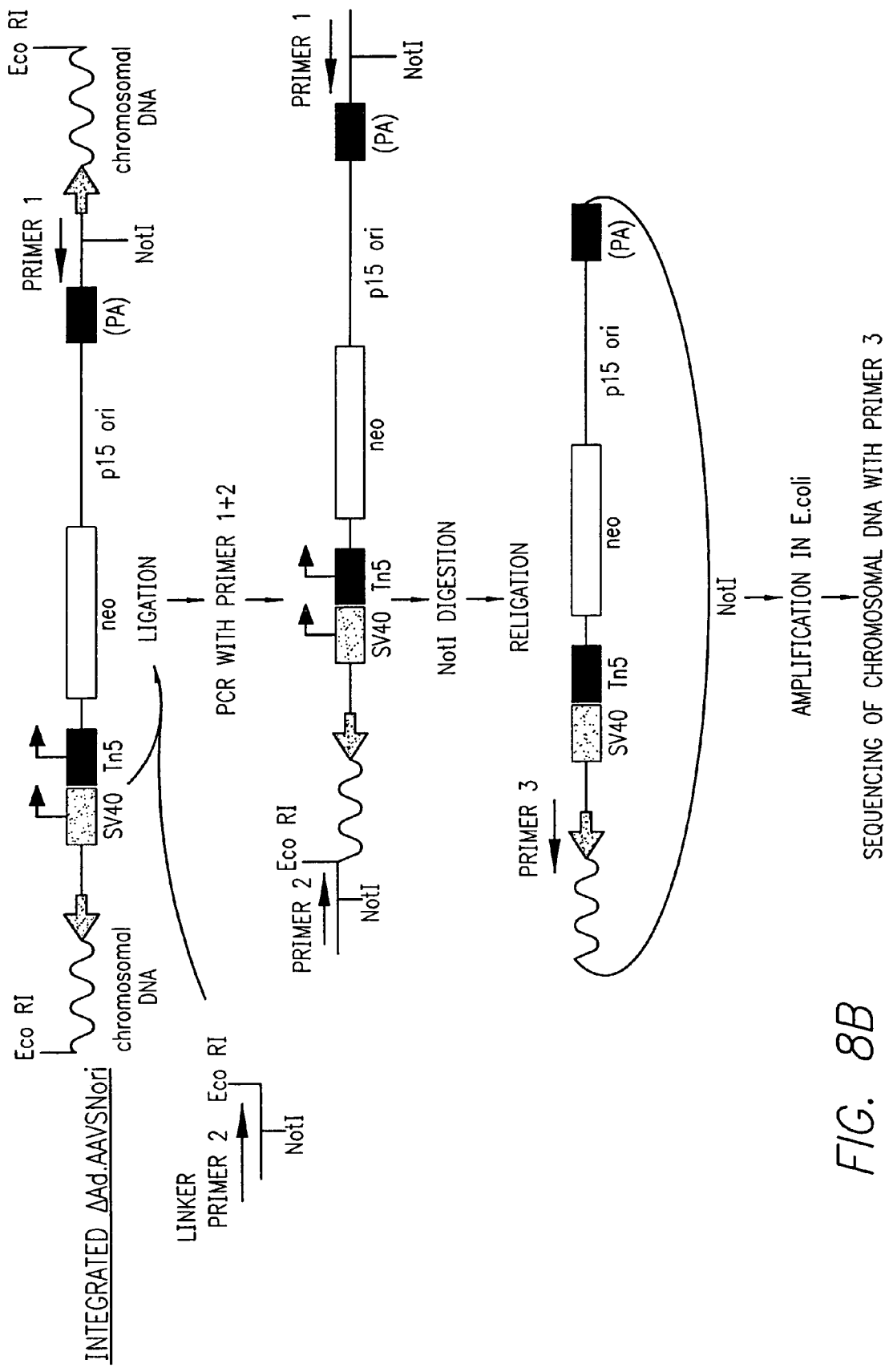

Integration Frequency with and Without G418 Selection:

In order to investigate the integration frequency of the different vectors and to confirm that AAV ITRs present in double-stranded adenoviral DNA genomes can mediate vector integration with a frequency comparable to rAAV vectors, integration studies are performed based on the formation of G418 resistant colonies with ΔAd.AAVSNori, AdSNori, Ad.SNoriITR, and rAAVSNori after infection with $2\times10^5$ and $2\times10^6$ genomes per cell (FIG. 8). After infection, cells are plated in 96 well plates under limiting dilution and selected with G418 to estimate the frequency of formation of G418 resistant colonies. Another set of cells is plated without G418. A representative number of clones (w/ and w/o G418 selection) are expanded to $>10^6$ cells (after 3–4 weeks of culture) and analyzed for the presence of viral DNA by Southern Blot as well as PFGE analysis to discriminate between episomal vector DNA and vector genomes stably associated with chromosomal DNA. This allows us to estimate the integration frequency of the different vectors, to assess the effect of G418 selection on integration, and to consider position effects on neo expression in calculating the total integration frequency. Integrated vector copies with a frequency of at least $1\times10^{-4}$ is predicted only for ΔAd.AAVSNori and rAAVSNori. The total number of colonies may be lower in both the first generation vectors, Ad.AAVSNoriITR and Ad.SNori, due to the toxic effects of expressed adenoviral proteins; however, a higher integration frequency is predicted for the vector containing the AAV ITRs (Ad.AAVSNoriITR).

Kinetics of Integration:

Compared to rAAV, the double-stranded nature of entering ΔAd.AAV genomes provides more protection against degradation. Furthermore, the synthesis of transcriptionally active double-stranded intermediates from single-stranded genomes, which is considered a limiting step in rAAV transduction, is not required in ΔAd.AAV transduction. Thus, the lag phase between infection and expression seen with rAAV vectors, which is causally linked to double-strand synthesis/integration may be shorter or absent in infections with ΔAd.AAV vectors. Furthermore, it was demonstrated earlier that a 9 kb mini-adenoviral genome packaged into adenoviral particles is only short lived and completely degraded by day 3 post-infusion. In contrast, transduction with the 5.5 kb ΔAd.AAV1 (FIG. 1) genome allows for long-term expression, suggesting that either AAV ITRs can stabilize the viral genome as an episome until it is integrated or integration occurs shortly after infection.

The status of vector DNA can be examined in K562 cells at different time points after infection with ΔAd.AAVSNori, AdSNori, Ad.AAVSNoriITR, or rAAVSNori (MOI $2\times10^5$). Infected cells are harvested at 1 hour, 5 hours, 1 day, 3, 7, and 14 days after infection and chromosomal DNA is analyzed by PFGE followed by hybridization with a transgene specific probe. This technique allows us to distinguish between episomal vector DNA, which appears as a distinct 5.0 kb band and integrated DNA. Furthermore, extra chromosomal high-molecular weight vector concatemers can be detected. In the case of random integration, after digestion of chromosomal DNA with I-CeuI or PI-SceI, vector-specific signals in the range of 1–2 mb should be seen. The intensity of episomal and integrated vector signal is quantified for each time point using phosphoimager analysis. This gives information about the kinetics of hybrid vector integration in a population of infected K562 cells and the intracellular stability of hybrid vector genomes.

Structure of Integrated Vector DNA and Integration Functions with Chromosomal DNA:

ΔAd.AAV1 integrates as concatemer/s randomly into host DNA as shown previously. How many vector copies are present in one concatemer and whether the extent and the kinetics of tandem-formation are dose dependent still remain unclear. Another unanswered question is how ΔAd.AAV integrates: whether one or both ITRs are involved, whether the integrated ITRs are still intact, and whether adenoviral sequences integrate as well. These issues are important for the strategy to include rep genes into the hybrid vector genome. Moreover, if intact AAV ITRs are present within integrated vector copies, helper virus (adenovirus or HSV) infection in vivomay mobilize the integrated AAV-ITR vector cassette and affect stability of transgene expression.

To answer these questions, K562 cells can be infected with ΔAd.AAVSNori, AdSNori, Ad.AAVSNoriITR, and rAAVSNori at MOIs $2\times10^5$, $2\times10^6$, or $2\times10^7$ genomes per cell. Infected cells are plated in 96 well plates in the presence or the absence of G418. The latter is included because G418 may cause amplification of integrated vector DNA (Rutledge, E. A. et al., 1997, *Journal of Virology*, 71:8429–36). Genomic DNA from isolated clones can be analyzed by regular Southern Blot as described in the Examples Section to confirm the presence of vector concatemers and calculate the number of integrated vector copies. More informative is the sequencing of integrated vector copies and their junctions with chromosomal DNA. The structure of integration junctions can be delineated using the role of AAV ITRs in vector integration and the extent of insertional mutagenesis after transduction. This data provides information about the potential risks of hybrid vector used in clinical trials.

Transduction of Cell Cycle Arrested Cells:

The ultimate target for the hybrid vectors described in the Specification are quiescent hematopoietic stem cells. We hypothesize that the double-stranded nature of ΔAd.AAV genomes and specific nuclear import mechanisms may allow for the transduction of non-dividing cells. This is in part supported by the transduction studies with ΔAd.AAV1 in quiescent hepatocytes in vivo. To confirm this data, primary fibroblasts can be forced to enter the $G_0$ phase by serum/growth factor starvation before infection with the hybrid vectors according to a protocol described by Russell (Russell, D. et al., 1995, *PNAS*, 92:5719–23). Cells are maintained for three days after infection under serum/growth factor deprivation. At this time point, genomic DNA is isolated and analyzed for integration events by PFGE in comparison with growing cells. Another series of integration studies can be carried out on K562 cells arrested in the G/S phase of the cell cycle with aphidicolin (added 1 day before and maintained several days after infection with hybrid vectors—depending on the integration kinetics studies described earlier). To investigate whether DNA damaging agents increase the transduction frequency of hybrid vectors, cell-cycle-arrested K562 cells or primary fibroblasts can be treated with cisplatinum or $^3$H-thymidine prior to virus infection according to a protocol described by Alexander and Russell (Alexander, I. E. et al., 1994, *J. Virol.*, 68:8282–87; Russell, D. et al., 1995, *PNAS*, 92:5719–23). Furthermore, the effect of chromosomal DNA decondensation on the transduction efficiency of hybrid vectors can be studied in arrested cells after treatment with puromycin, staurosporin, Hoechst 3328, distramycin, or vandate.

F. Improvements in ΔAd.AAV Production and Purification

To inhibit packaging of full-length genomes a modified form of I-Sce I, a yeast mitochondrial intron-endonuclease with a non-palindromic 18-bp recognition sequence is expressed in 293 cells. Constitutive expression of this enzyme in mammalian cells is not toxic, possibly due to either the lack of I-SceI sites in the genome or sufficient repair of them (Rouet P. et al, 1994, *PNAS*, 91:6064–8). The yeast I-Sce I is modified with an SV40 T-antigen nuclear localization signal and an optimal Kozak sequence to enhance its functionality in mammalian cells (Rouet P. et al, 1994, *PNAS*, 91:6064–8). For another yeast endonuclease it was shown that a recognition site within an transduced Ad genome was efficiently (30% of all transduced genomes) when expressed in human A549 cells. Importantly, the expression of E4 ORF6 and ORF3 expressed from the transduced Ad genome inhibited double-strand break repair mediated by the endonuclease (Nicolas, A. L. et al, 2000, *Virology*, 266:211–24). This is consistent with the observations by others where these E4 proteins prevent concatemerization of the viral genome (Boyer, J. et al, 1999, *Virology*, 263:307–12). Based on this, packaging of full-length virus containing a I-Sce1 recognition site is reduced in 293 cells constitutively expressing I-Sce I. The 18mer I-Sce site is inserted into the E3 region of the Ad.IR vectors. These vectors are generated and amplified in 293 cells followed by a large-scale infection of 293 cells expressing I-SceI. Alternatively, an expression cassette for the endonuclease XhoI is inserted into the E3 region of Ad.IR or Ad.AAV vectors. The XhoI, gene will be modified for optimal function in mammalian cells. Vectors expressing XhoI are generated and amplified in 293 cells expressing the Xho I isoschizomer PaeR 7 methyltransferase (PMT) (Nelson, J. E. et al, 1997, *J. Virol.*, 71:8902–7), which mediates the addition of a methyl group onto the N6 position of the adenine base of Xho I sites, CTCGAG. This protects the viral and cellular genome from XhoI cleavage. Methylated Ad vectors are produced at high titers. ΔAd.AAV vectors are then obtained by large-scale infection of 293 cells with the Ad.AAV-XhoI vectors. At this stage the viral genome is not methylated and is digested at the XhoI sites. XhoI sites present within the transgene cassette are deleted by site-directed mutagenesis without altering the amino acids sequence. (XhoI is accumulated only at late stages in virus replication and should act only upon a large part of Ad DNA when replication is completed. In addition, ultracentrifugation optimizes the separation between ΔAd.IR and ΔAd.IR particles (Blague, C. et al., 2000, *Blood*, 95:820–8).

EXAMPLE II

Modified Fiber Protein

A. Test the Infectivity of Different Human or Animal Serotype on Human Bone Marrow Cells.

Figure 9:
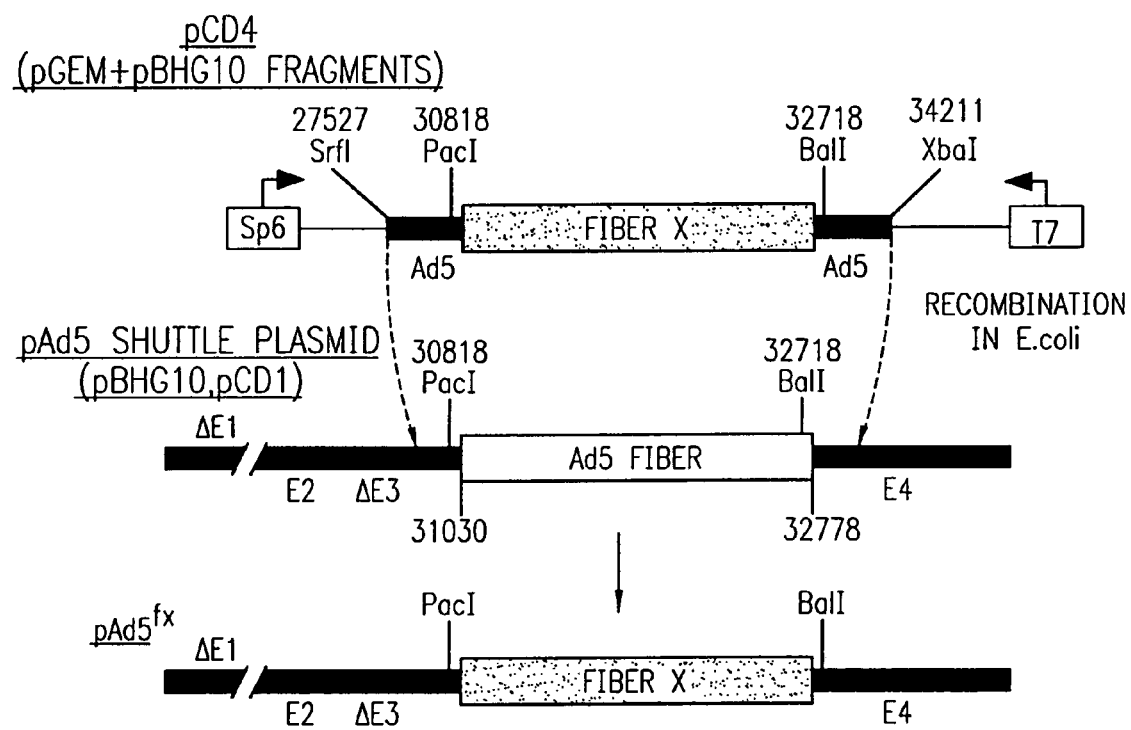
FIG. 9 shows strategy for substituting the Ad5 fiber sequence by the heterologous fiber X genes using recombination in E. coli.

Since the amino acid sequence of the fiber knob region varies considerably among the ~50 known serotypes, it is thought that different adenovirus serotypes bind to different cellular receptor proteins or use different entry mechanisms (Shenk, T., 1996, In B. N. Fields, et al. (eds.), *Fields Virology*, vol. 2 Lippincott-Raven Publisher, Philadelphia; Mathias, P. et al., 1994, *Journal of Virology*, 68:6811–14; Defer, M., et al., 1993, *J. of Virology*, 64, 3661–3673). Although most adenoviruses contain RGD motifs in the penton base proteins, there are a number of serotypes (e.g. Ad 40, 41) without this conserved sequence. These types may use integrin □v-independent pathways for virus internalization (Davison, A. J., et al., 1993, *J. Mol. Biol.*, 234, 1308–1316; Mathias, P. et al., 1994, *Journal of Virology*, 68:6811–14). To test whether other Ad serotypes can infect stem cell subpopulation present in human bone marrow, studies with a series of different human Ad serotypes and animal viruses can be performed (see Table II). As a means to verify efficient transduction with Ad serotypes, viral DNA is tagged before infection and the presence of viral genomes in the nuclei of transduced cells is investigated. Furthermore, whether viral DNA is replicated in transduced cells can be analyzed as indirect proof for early viral gene expression. A direct detection of expressed viral proteins is impossible due to the unavailability of antibodies against all the serotypes included in this study. Simultaneously with the infection assay, transduced human bone marrow cells can be analyzed for morphological and immunohistochemical features characteristic of HSC or progenitor subpopulations. For retargeting, serotypes which are able to infect CD34+ subsets of bone marrow cells at the lowest MOI are selected. As the next step, the fiber gene is PCR-cloned from serotypes with potential HSC/CD34+tropism and inserted into standard shuttle plasmids for Ad5 vector generation replacing the Ad5 fiber gene using an *E. coli* recombination system (FIG. 9).

Methods

Cells and Viruses:

HeLa (human cervix carcinoma, ATCC CCL-2.2), CHO (chinese hamster ovary, ATCC CCL-61), K562 (human hematopoietic, ATCC 45506), HEp-2 (human larynx carcinoma, ATCC CCL-23), 293 (human embryonic kidney, Microbix, Toronto Canada) cells were maintained in DMEM, 10% FCS, 2 mM glutamine, and Pen/Strep. Culture media for CHO cells was supplemented with 200 μM asparagine and 200 μM proline. Human CD34+-enriched bone marrow cells were purified from peripheral blood after mobilization using MiniMACS VS$^+$ separation columns (Miltenyi Biotec, Auburn, Calif.), according to the manufacturer's instructions. Aliquots were stored in liquid nitrogen. Sixteen hours before the experiment, cells were recovered from the frozen stock and incubated overnight in IMDM media, supplemented with 20% FCS, $10^{-4}$ M β-mercaptoethanol, 100 μg/ml DNaseI, 2 mM glutamine, 10 U/ml IL-3, and 50 ng/ml stem cell factor (SCF) or 2 ng/ml thrombopoietin (Tpo). The purity of CD34+preparations was verified by flow cytometry and was consistently greater than 90%.

Flow Cytometry:

Adherent cells (CHO, HeLa) grown in non-tissue culture treated 10 cm dishes (Falcon, Franklin Lakes, N.J.) were detached by treatment with 1 mM EDTA and washed three times with wash buffer (WB), consisting of PBS supplemented with 1% FCS. Cells grown in suspension (K562, CD34+) were washed three times with WB. After washing, cells were resuspended in WB at $2\times10^6$ cells/ml. $2\times10^5$ cells were incubated in WB for 1 h at 37° C. with monoclonal antibodies specific for $\alpha_v$-integrins [L230, ATCC: HB-8448, (Rodriguez, E., Everitt, E. 1999. Arch. Virol. 144:787–795) (1/30 final dilution), CAR [RmcB (Bergelson, J. M., et al. 1997. Science. 275:1320–1323; Hsu, K.-H., L., et al. 1988. *J Virology.* 62:1647–1652) (1/400 final dilution)], or BrdU [(Amersham, Arlington Heights, Ill.) (1/100 final dilution)]. Subsequently, cells were washed with WB, and incubated with fluorescein isothiocyanate (FITC)-labeled horse anti-mouse IgG antibodies [(Vector Labs., Burlingame, Calif.) (1/100 final dilution)] or phycoerythrin (PE)-labeled goat anti-mouse IgG antibodies [(Calbiochem, La Jolla, Calif.) 1:100 dilution] for 30 min at 4° C. After incubation with secondary antibodies, cells were washed two times with WB and $10^4$ cells per sample were analyzed in duplicate by flow cytometry.

For the analysis of CD34 and c-kit expression on transduced CD34+-cells and for fluorescent activated cell sorting (FACS), purified human CD34+ cells were incubated with phycoerythrin(PE)-conjugated anti-CD34 monoclonal antibodies (Becton-Dickinson Immunocytochemistry Systems, San Jose, Calif.) or with PE-labeled anti-CD117 (c-kit) monoclonal antibodies (MAb 95C3, Immunotech, Beckman Coulter, Marseille, France) according to the manufacturer's protocol followed by flow cytometry analysis. All analyses and sortings were performed on a FACStar Plus flow cytometer (Becton Dickinson, Franklin Lakes, N.J.) equipped with 488 nm argon and 633 nm HeNe lasers. For analysis of c-kit expression and FACS purification of CD34+/c-kit+ cells, SCF was not added to the media during culturing of CD34+ cells.

Results

CAR/$\alpha_v$-Integrin Expression on Test Cells:

It is generally accepted that CD34+ cells possess bone marrow repopulating activity. Therefore, we used human CD34+ cells as the target for our studies towards identifying Ad serotypes with HSC tropism and constructing new viral vectors. Studies were performed on mobilized, CD34-positive, peripheral blood cells from one donor under conditions which are known to retain CD34+ cells in a quiescent stage (Leitner, A., et al. 1996. *Br. J. Haematol.* 92:255–262; Roberts, A. W., Metcalf, D. 1995. *Blood.* 86:1600–1605). More than 90% of purified cells were CD34 positive by flow cytometry. Furthermore, we included into our Ad tropism studies the cell line K562, which is considered to be an adequate model for studying gene transfer into human hematopoietic cells (McGuckin, et al. 1996. *British Journal of Haematology.* 95:457–460). HeLa cells, which are readily infectible by Ad5, and CHO cells, which are refractory to Ad5 infection (Antoniou, M. et al., 1998, *Nucleic Acid Res.*, 26:721–9), were used as positive and negative control cell lines, respectively.

For Ad5, both, binding to the primary receptor and to $\alpha_v\beta_5$ and $\alpha_\omega\beta_5$ integrins are important for high efficiency infection of target cells. The expression of CAR and $\alpha_v$ integrins on test cells was analyzed by flow cytometry using monoclonal antibodies against CAR (RmcB (Bergelson, J. M., et al. 1997. *Science.* 275:1320–1323; Hsu, K.-H., L., et al. 1988. *J Virology.* 62:1647–1652)) and $\alpha_v$ integrins (L230 (Roelvink, P. W., et al. 1996. *J Virology.* 70:7614–7621)) (FIG. 10). As expected, nearly all HeLa cells expressed high levels of CAR and $\alpha_v$-integrins, whereas CHO cells lacked significant CAR and $\alpha_v$-integrin expression. Fifteen and 77% of K562 cells expressed CAR and $\alpha_v$-integrins, respectively. Only ~6% of the CD34+ cells used in our studies expressed CAR and 17% were positive for $\alpha_v$-integrins. Notably, the preparation of CD34+ cells represents a mixture of different cell types. The absent or low expression of primary and secondary Ad5 receptors on non-cycling human CD34+ cells is in agreement with previous reports (Huang, S., et al. 1996. *J Virology.* 70:4502–4508; Neering, S. J., et al. 1996. *Blood.* 88:1147–1155; Tomko, R. P., et al. 1997. *Proc. Natl. Acad. Sci. USA.* 94:3352–3356).

Infection Assay Using Wild-Type Ad5 and K562 Cells:

The presence of viral DNA in the nucleus of infected cells is an indirect means to demonstrate efficient virus binding, internalization, and nuclear import. Nuclear localization of the viral genome is a prerequisite for transgene transcription and integration. Two techniques are utilized to tag viral DNA for in situ analysis. To optimize the infection assay, wild-type Ad5 virus and K562 cells which are permissive for Ad5 infection can be used. The first protocol (Challberg, S. S. and Ketner, S. 1981, *Virology* 114, 196–209), is based on $^{32}$P-labeling of viral DNA. During amplification of wild-type Ad5 and A549 cells, $^{32}$P-phosphate (40 μCi/ml) is added to phosphate-free medium. After development of CPE, $^{32}$P-tagged virus is harvested, banded in CsCl gradients, and titered on HeLa cells according to standard protocols. To simulate the conditions for infection of human bone marrow cells, K562 cells are incubated in suspension with a MOI of 1, 10, or 100 of $^{32}$P-Ad5 for 2, 4, 6, or 8 hours under agitation at 37° C. This covers the time period necessary for adsorption, internalization, and nuclear import. After washing, cells are fixed either transferred to microscopy slides using cytospin or embedded in paraffin and sectioned (according to protocols from VECTOR labs, Burlingham, Calif.). The latter has the potential advantage that multiple consecutive sections (5 μm) of the same cell can be analyzed by different methods (e.g. for $^{32}$P tagged viral DNA, for specific histological staining, for immunfluorescence), which allows for correlating infection with a particular cell type present in the bone marrow. Cells are incubated in a Kodak NTB-2 photo emulsion for autoradiography. The exposure time can be optimized to minimize background or non-nuclear localized signals. A dose and time dependent appearance of nuclear silver grains is expected under the optimized conditions. Since $^{32}$P-phosphate can label viral proteins as well, a cytoplasmic background signal might appear. To facilitate detection, immunofluorescence with HSC specific antibodies on sections can be performed. As an alternative method, a BrdU-labeling technique for viral DNA can be used (Lieber, A., et al. 1999. *J Virol* 73:9314–24; Lieber, A. et al., 1996, *Journal of Virology,* 70:8944–60). In this case, different amounts of BrdU are added to the A549 culture medium during wtAd5 virus propagation. BrdU labeled viral DNA can be detected with monoclonal antibodies specific to BrdU. The signal can be enhanced using layers of species-specific polyclonal antibodies in combination with biotin/avidin and a fluorescent marker. BrdU tagged viral DNA can be detected on cytospins of bone marrow cells together with cell surface markers by double or triple immunoflourescence.

Discussion

The interaction of selected Ad serotypes with CD34+ cells was tested. As a result of this screening we constructed a first-generation, Ad5-based vector whose fiber was substituted with the fiber derived from Ad35. We demonstrated that this capsid modification allowed for efficient viral transduction of potential HSCs by the corresponding chimeric Ad vectors.

All tropism and transduction studies were performed with non-cycling CD34+ cells, which are thought to include HSCs. The quiescent stage of CD34+ cells purified from mobilized blood is important because induction of cell proliferation is associated with a loss of the ability to reconstitute hematopoiesis and with changes in the spectrum of cellular receptors (Becker, P. S., et al. 1999. *Exp. Hematol.* 27:533–541). It is known that treatment of hematopoietic cells with cytokines or growth factors changes the expression of specific integrins including $\alpha_v$-integrins, which would ultimately alter the susceptibility of cells to Ad infection or may effect viability of infected cells (Gonzalez, R., et al. 1999. *Gene Therapy.* 6:314–320; Huang, S., et al. 1995. *J. Virology.* 69:2257–2263). Another fact that complicates the interpretation of transduction studies is the extraordinary heterogeneity of CD34+ cells in regards to morphology and function.

B. Screening Different Adenoviruses to Establish Tropism to HSC.

The ATCC provides more than 70 different human or animal adenoviruses (see Appendix I). A collection of 15 human serotypes and 6 animal adenoviruses (see Table II) are selected based on the following criteria: (i) availability of the complete genome sequence or fiber sequence from the NIH gene bank (ii) CAR receptor usage absent or unknown, (iii) different subgroups, and (iv) moderate or low tumorigenicity (Shenk, T., 1996, In B. N. Fields, et al. (eds.), *Fields Virology*, vol. 2 Lippincott-Raven Publisher, Philadelphia). However, any serotype shown in the Appendix hereto can be used for the invention described. Animal viruses are included in the infectivity assay because this may provide a means to circumvent the pre-existing humoral immunity against human Ad5 fiber, which represents a critical obstacle for clinical trials with Ad vectors.

Methods

Viruses:

The following human adenovirus serotypes were purchased from the ATCC: 3 (VR-3), 4 (VR1081), 5 (VR-5), 9 (VR1086), 35 (VR-716) and 41 (VR-930). Adenovirus No. VR-716 was purchased from ATCC labeled as serotype 34, however it was found to be serotype 35 upon sequencing of the fiber region. For amplification, the corresponding Ads were infected onto HeLa, 293, or HEp-2 cells under conditions that prevented cross-contamination. Virus was banded in CsCl gradients, dialyzed and stored in aliquots as described elsewhere (Lieber, A., C.-Y. et al. 1996. *Journal of Virology.* 70:8944–8960). Plaque titering was performed as follows: Confluent 293 cells plated in 6-well plates were incubated for 24 hours with virus in a total volume of 1 ml. Two weeks after infection, plaques were counted on cultures overlayed with 1% agarose/MEM/10% FCS.0

EM Studies:

CsCl-banded Ad stocks were thawed and diluted with 0.5% glutaraldehyde. Grids were prepared as described earlier (Mittereder, N., et al. 1996. *J. Virology.* 70:7498–7509). After staining with 2% methylamine tungstate (Nanoprobes, Stony Brook, N.Y.), the carbon-coated grids were evaluated and photomicrographed with a Phillips 410 electron microscope, operated at 80 kV (final magnification 85,000×). For each particular Ad serotype, the number of morphologically deficient viral particles per 100 was counted in five random fields.

Results

Electron Microscopy:

Little is known about the stability of particles from serotypes other than Ad5. Since the intactness of viral particles was crucial for comparative interaction studies, virions from the serotypes specified above were analyzed by electron microscopy (EM). EM studies of negative contrast stained Ad suspensions demonstrated that the percentage of defective particles (loss of icosahedral shape or luminal staining) did not exceed 5% indicating that serotype preparations had comparable qualities. Representative EM photographs are shown: for Ads 5, 9, and 35 (FIG. 11).

Serotype Screening:

It is thought that different Ad serotypes bind to different cellular receptor proteins and use different entry mechanisms (Defer, C., et al., P. 1990. *J. Virology.* 64:3661–3673; Mathias, P., et al. 1994. *Journal of Virology.* 68:6811–6814). A set of human adenoviruses was obtained from the ATCC to be tested for tropism to CD34+ cells. These included serotypes 3, 4, 5, 9, 35, and 41 representing different subtypes (Table 1). We believed that these serotypes would use different cellular attachment and internalization strategies due to differing lengths of fiber shafts (Chroboczek, J., et al. 1995. *Adenovirus fiber*, p. 163–200. In a. P. B. W. Doerfler (ed.), *The molecular repertoire of adenoviruses*, vol. 1. Springer Verlag, Berlin; Roelvink, P. W., et al. 1998. *J. Virology.* 72:7909–7915), the presence or absence of RGD motifs within the penton base, and differing tissue tropism. The relatively little characterized Ad35 was selected because it was found in immunocompromised hosts, particularly in bone marrow recipients (Flomenberg, P., et al. 1994. *Journal of Infectious Diseases.* 169:775–781; Flomenberg, P. R., et al. 1987. *Journal of Infectious Diseases.* 155:1127–1134; Shields, A. F., et al. 1985 New England *Journal of Medicine.* 312:529–533). The latter observations prompted us to believe that bone marrow cells are among the natural reservoirs for Ad35.

TABLE II

| | Human and animal adenoviruses with potential interest for the invention | | | | | | | | |
|---|---|---|---|---|---|---|---|---|---|
| Adenovirus | Human/ Group B | Human/ Group D | Human/ Group F | Avian | Bovine | Canine | Ovine | Swine | Mouse |
| Serotype | 3, 7, 11, 16, 21, 34, 35 | 8, 15, 17, 19, 28, 37 | 40, 41 | CELO, EDS | 3 | 1, 2 | 5 | 4 | 1 |

The underlined serotypes use CAR independent pathways for cell entry.

For amplification, the corresponding adenovirus stocks can be infected onto HeLa or A549 cells such that at a given time only one virus type is handled in a separate laminar flow hood and cultured in Hepa-filtered bottles, preferentially in separate $CO_2$ incubators to avoid cross-contamination. During propagation, viral DNA is tagged using one of the techniques described earlier. Viral DNA can be isolated from purified particles. The XhoI restriction pattern is analyzed for methylated and unmethylated viral DNA by Southern blot using the full genome of the corresponding virus type as a radioactive probe.

Discussion

Although it was reported earlier by slot-blot assay that fiber knobs derived from 2, 9, 4, and 41 L can bind to CAR (Roelvink, P. W., et al. 1998. *J. Virology*. 72:7909–7915), it is not clear whether this binding occurs with an affinity that is physiologically relevant and whether this would confer cell entry. Furthermore, as shown for the Ad5 interaction between the penton and intergrins, a secondary receptor is required to induce virus internalization. We demonstrated that different serotypes interacted differently with the K562 or CD34+target cells. Ad5, Ad4, and Ad41 were not able to efficiently attach to and be internalized by K562 and CD34+ cells. Although Ad4 belongs to a separate subgroup (E), it is thought that Ad4 represents a natural hybrid between subgroup B and C viruses with a fiber related to Ad5 (Gruber, W. C., et al. 1993. *Virology*. 196:603–611). Therefore, it was not surprising that Ad4 has binding properties similar to Ad5. The subgroup F serotype Ad41 has been shown to contain distinct fibers, a long shafted and a short-shafted fiber allowing for different cell entry pathways (Tiemessen, C. T., Kidd, A.H. 1995. *J. Gen. Virol*. 76:481–497). The Ad41 penton base does not contain RGD motifs suggesting that this virus may use $\alpha_v$-intregrin independent pathways for cell entry. However, these features did not improve interaction with CD34+ cells. Ad9, Ad3, and Ad35 did interact with CD34+ cells more efficiently than Ad5. Out of all the serotypes tested, Ad35 demonstrated the most efficient attachment and internalization with K562 and CD34+ cells. Although the short-shafted Ad9 can bind to CAR, it preferentially uses $\alpha_v$-integrins for cell entry (Roelvink, P. W., et al. 1996. *J. Virology*. 70:7614–7621). Therefore, the low level of $\alpha_v$-integrin expression on certain subsets of CD34+ cells may account for the observed susceptibility to Ad9.

C. Attachment and Internalization of the Ad Serotypes to K562 and CD34+ Cells.

Methods

Labeling of Ads with [$^3$H]-methyl thymidine:

Serotypes were labeled with [$^3$H]-methyl thymidine as described in detail elsewhere (Roelvink, P. W., et al. 1996. *J. Virology*. 70:7614–7621). Briefly, $5\times10^7$ HeLa or 293 cells were grown in 175 sq. cm flasks with 15 ml DMEM/10% FCS and infected with wild type adenovirus at a MOI of 50 or higher. Twelve hours post-infection, 1 mCi of [$^3$H]-methyl thymidine (Amersham, Arlington Heights, Ill.) was added to the media and cells were further incubated at 37° C. until complete CPE was observed. Then, cells were harvested, pelleted, washed once with cold PBS, and resuspended in 5 ml PBS. Virus was released from the cells by four freeze-thaw cycles. Cell debris was removed by centrifugation and viral material was subjected to ultracentrifugation in CsCl gradients and subsequent dialysis as previously described (Lieber, A., C.-Y. et al. 1996. *Journal of Virology*. 70:8944–8960). Virus purification and dialysis removed unincorporated radioactivity. Wild type Ad particle concentrations were determined spectrophotometrically by measuring the $OD_{260}$, utilizing the extinction coefficient for wild-type Ad5 $\epsilon_{260}=9.09\times10^{-13}$ OD ml cm virion$^{-1}$ (Maizel, J. V., et al. 1968. *Virology*. 36:115–125). The virion specific radioactivity was measured by a liquid scintillation counter and was always in the range of $1\times10^{-5}$ to $1\times10^{-4}$ cpm per virion. For selected variants, the fiber gene was PCR amplified and sequenced to ensure identity and the absence of cross-contamination.

Viral DNA Tagged with Methylase and Test for Replication by Genomic Southern Blots:

To ultimately confirm transduction, a protocol to detect adenoviral replication in infected cells can be established. Viral DNA synthesis can only occur after de novo expression of adenoviral early genes. A site-specific methylation strategy is utilized to monitor viral DNA replication within infected cells (Nelson, J. et al., 1997, *Journal of Virology*, 71:8902–07). Methylation marked adenovirus can be produced by the addition of a methyl group onto the N6 position of the adenine base of XhoI sites, CTCGAG, by propagation of the virus in HeLa or A549 cells expressing the XhoI isoschizomer PaeR7 methyltransferase (PMT) (Kwoh, T. J., et al., 1986, *Proc. Natl. Acad. Sci. USA* 83, 7713–7717). It is known that methylation does not affect vector production but does prevent cleavage by XhoI. Loss of methylation through viral replication restores XhoI cleavage and can be detected by Southern blots of genomic DNA from infected cells in comparison to native, non-methylated, viral genomes.

Attachment and Internalization Assays:

These studies were performed based on a protocol published elsewhere (Wickham, T. J., et al. 1993. *Cell*. 73:309–319). In preliminary experiments, we found that labeled Ad5 virions reached equilibrium in attachment to HeLa cells after 45 min at 4° C. with an MOI of 400 pfu per cell. For attachment studies, $3.5\times10^5$ cells were incubated for one hour on ice with equal amounts of [$^3$H]-labeled adenovirus OD particles equivalent to an MOI of 400 pfu/cell for Ad5 in 100 μl of ice-cold adhesion buffer (Dulbeco's modified Eagle's medium supplemented with 2 mM $MgCl_2$, 1% BSA, and 20 mM HEPES). Next, the cells were pelleted by centrifugation for 4 min at 1000×g and washed two times with 0.5 ml ice-cold PBS. After the last wash, the cells were pelleted at 1500×g, the supernatant was removed, and the cell-associated radioactivity was determined by a scintillation counter. The number of viral particles bound per cell was calculated using the virion specific radioactivity and the number of cells. To determine the fraction of internalized [$^3$H]-labeled adenoviral particles, cells were incubated on ice for one hour with the corresponding virus, washed with PBS as described above, resuspended in 100 μl adhesion buffer, and then incubated at 37° C. for 30 min. Following this incubation, cells were diluted 3-fold with cold 0.05% trypsin-0.5 mM EDTA solution and incubated at 37° C. for an additional 5–10 min. This treatment removed 99% of attached radioactivity. Finally, the cells were pelleted at 1500×g for 5 min, the supernatant was removed, and the protease-resistant counts per minute were measured. This protocol minimizes the possibility that the internalization data were affected by receptor recycling (Rodriguez, E., Everitt, E. 1999. *Arch. Virol*. 144:787–795). Nonspecific binding of Ad particles to cells on ice was determined in the presence of 100-fold excess of unlabeled virus. This value routinely represented less than 0.1% of viral load.

Results

Figure 12:
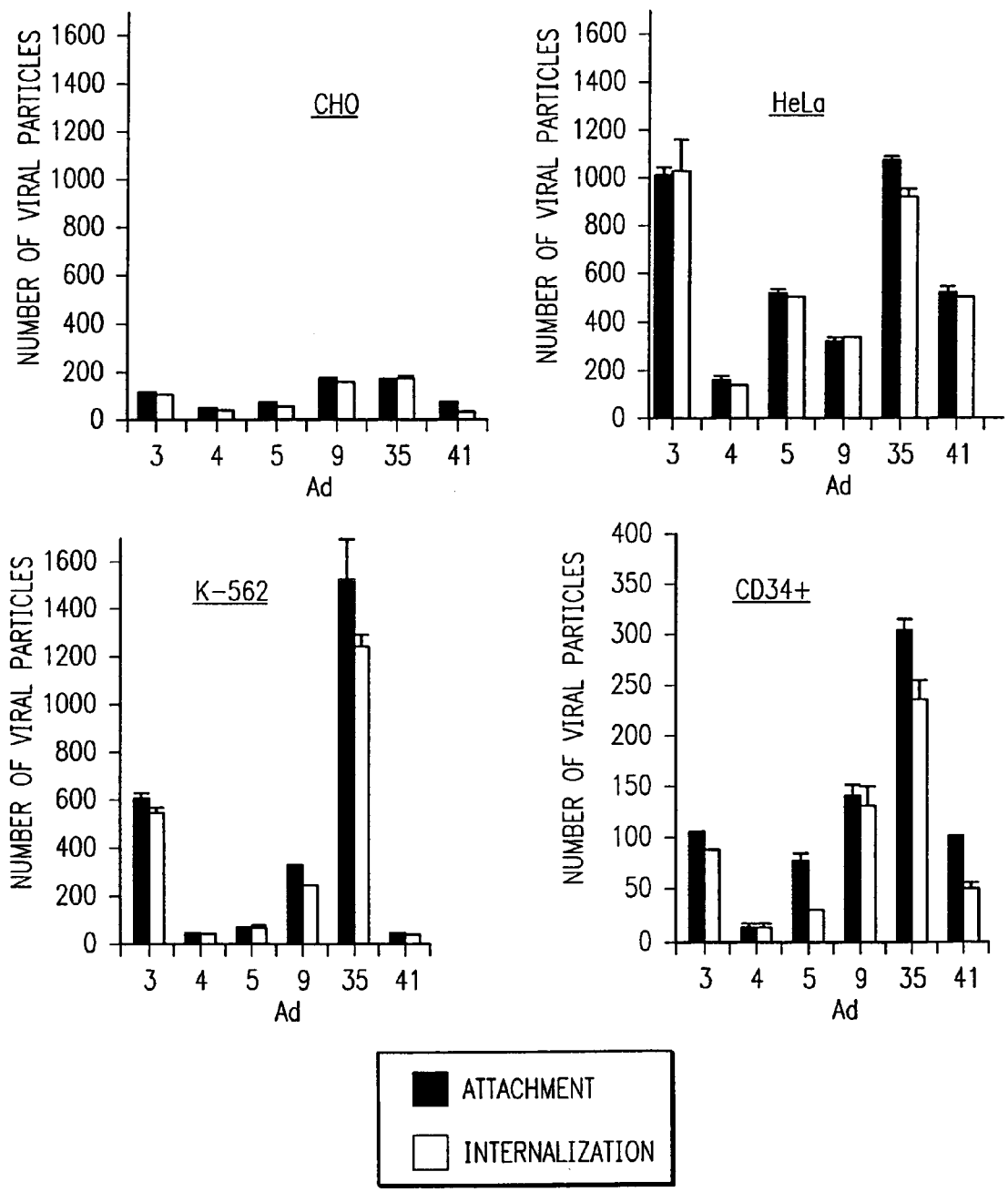
FIG. 12 shows the analysis of attachment and internalization of different serotypes to CHO, HeLa, K562, and CD34+ cells. Equal amounts of [$^3$H]-thymidine-labeled virions of Ads 3, 4, 5, 9, 35, and 41 (measured by $OD_{260}$, and equivalent to an MOI of 400 pfu per cell for Ad5) were incubated for one hour on ice as described in Materials and Methods. Cells were then washed, and the number of labeled virions bound per cell was determined. For internalization studies, viruses were first allowed to attach to cells for 1 h on ice. Then, unbound viral particles were washed out. Cells were then incubated at 37° C. for 30 min followed by treatment with trypsin-EDTA and washing to remove uninternalized viral particles. The data were obtained from two to four independent experiments performed in triplicate. Note the different scale on the Y-axes for CD34+ cells.

Attachment of Ad Particles to Target Cells and Internalization:

The selected serotypes were metabolically labeled with [$^3$H]-thymidine, which is incorporated into viral DNA during replication. Adsorption and internalization can be experimentally dissociated by taking advantage of the observation that at low temperature (0–4° C.) only virus cell attachment occurs, whereas internalization requires incubation at higher temperatures. The number of particles adsorbed or internalized per cell was calculated using the virion-specific radioactivity and used to quantify interaction of Ads 3, 4, 5, 9, 35, and 41 with CD34+, K562, HeLa and CHO cells (FIG. 12). The serotypes varied significantly in their ability to attach to and to be internalized by the different cell lines. For Ad5, the degree of attachment to the cell lines tested correlated with the level of CAR expression. In CHO cells, which were previously shown to be refractory to Ad5 infection, the level of attachment and internalization was about 50–70 viral particles per cell. This number was hereafter assumed negative in terms of susceptibility of a given cell type for Ad5. Interaction of the other serotypes with CHO cells was not significantly higher indicating that corresponding receptor/s were absent on CHO cells. All serotypes tested interacted with HeLa cells; with Ad3 and Ad35 being the most efficient variants. The presence of distinct Ad3 and Ad5 receptors on HeLa cells was demonstrated previously (Stevenson, S. C., et al. 1995. *J. Virology.* 69:2850–2857). Ads 4, 5, and 41 did not bind to K562 cells. In contrast, Ad9 as well as the members of subgroup B, Ad3 and Ad35, efficiently interacted with K562 cells with Ad35 having the highest number of adsorbed and internalized particles. Compared to Ad5, about 25 times more Ad35 particles were attached and three-forth of these were internalized by K562 cells. Viral interactions with CD34+ cells were generally weaker. Among the serotypes tested, only Ad9 and Ad35 were significantly internalized by non-cycling CD34+ cells. Internalization of Ad9 and Ad35 was, respectively, four and eight times more efficient than for Ad5 particles. The number of Ad35 virions internalized by CD34+ cells was almost half of that seen for Ad5 in HeLa cells, which can be readily infected with Ad5 based vectors.

Figure 13A:
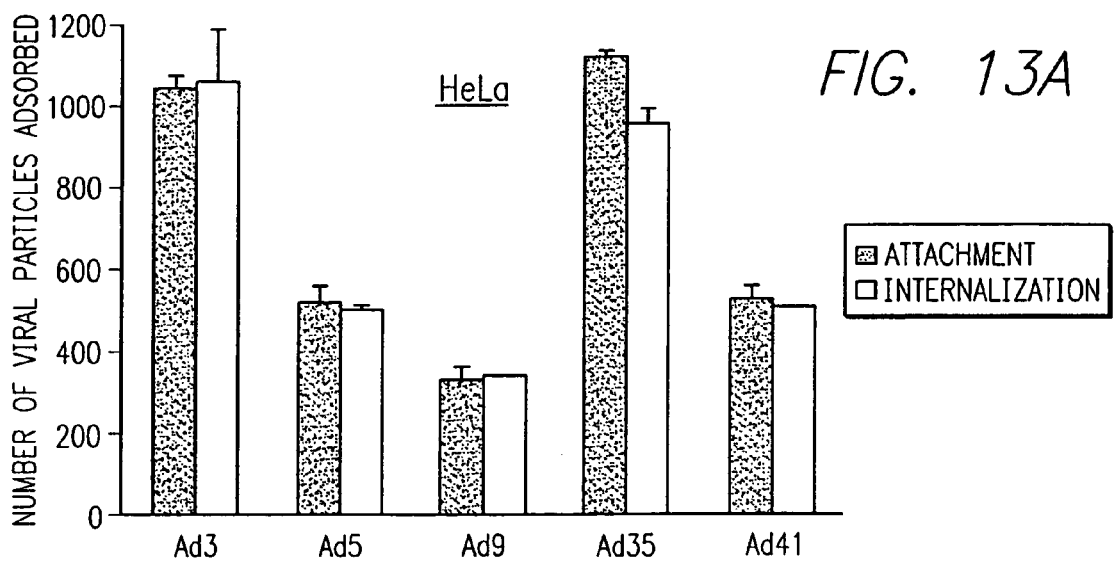
FIGS. 13A–13C show attachment and internalization of different adenovirus serotypes to Hela, CHO and 293 cells respectively.
Figure 13B:
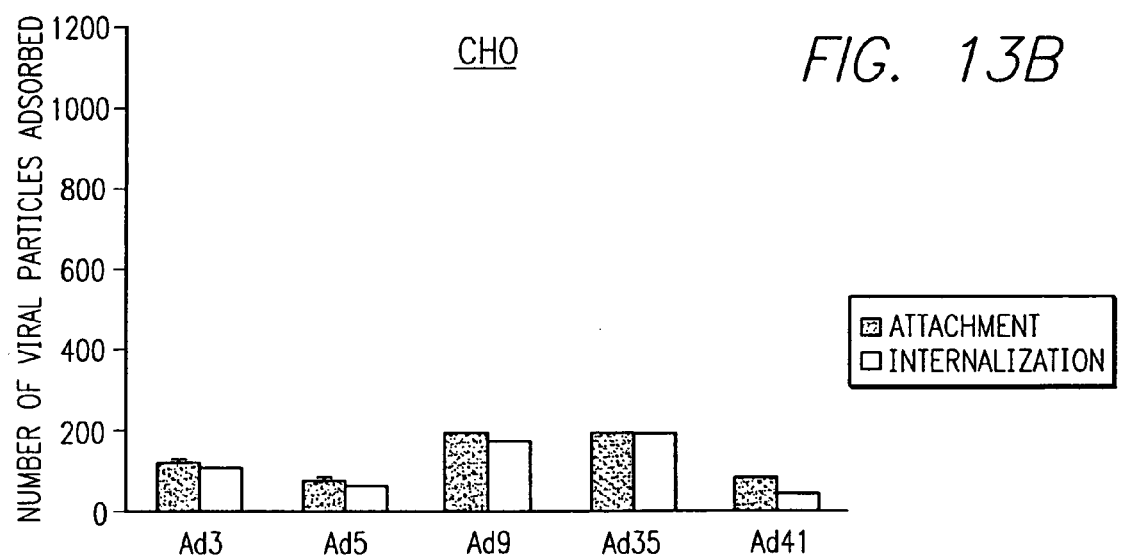
Figure 13C:
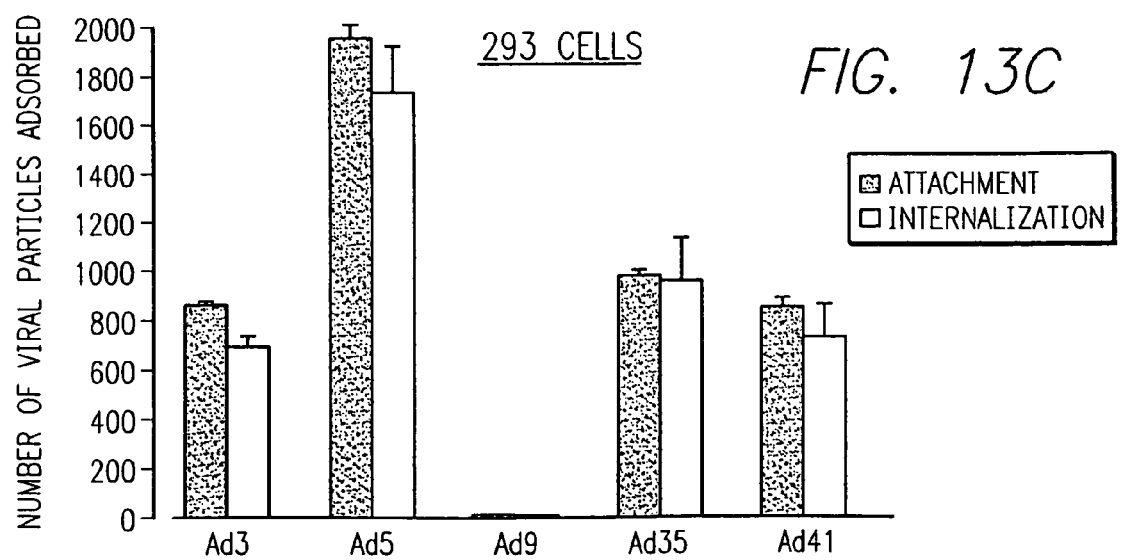

Attachment and Internalization of Adenovirus Serotypes 3, 5, 9, 35 and 41 into Hela, 293, and CHO Cells:

Hela and 293 cells expressing high level of primary and secondary receptors for human adenoviruses are used as a positive control for virus attachment and internalization. As a negative control CHO cells are used. CHO cells do not express the primary adenoviral receptor at a detectable level, and are therefore refractory for adenoviral infection. For attachment studies, these adherent cell lines are detached from 10 cm dishes with PBS-EDTA solution (without Ca2+ and Mg2+), washed three times with ice-cold PBS, resuspended in adhesion buffer, and incubated with viruses as described above in the Examples section. As expected, all adenoviral serotypes tested are efficiently attached to and internalized into Hela cells (Table III) (FIG. 13). Adenoviruses serotypes 3, 5, 35, 41, but not 9, are efficiently attached to and internalized by 293 cells. In contrast, poor attachment and internalization of most adenovirus serotypes are observed with CHO cells. The level of attachment on CHO is about 50–70 virus particles per cell for adenoviruses serotypes 5 and 41, 115 virus particles per cell for adenovirus type 3 and about 180 particles per cell for adenovirus serotypes 9 and 35. For further analysis, numbers >300 viral particles per cell are assumed as positive and <70 viral particles per cell as negative in terms of susceptibility of a particular cell line for efficient adenoviral transduction.

TABLE III

Comparative analysis of attachment and internalization of Ad5 and Ad9 to cell lines, expressing different amounts of CAR and αvβintegrins.

| Cell line | CAR expression | αvβ-integrin expression | Ad9 (attached/internalized) | Ad5 (attached/internalized) |
|---|---|---|---|---|
| HeLa | ++ | ++ | 426/370 | 550/500 |
| CHO | – | ++ | 300/300 | 70/50 |
| 293 | ++ | ++ | 20/20 | 1950/1750 |
| Y79 | +++ | – | 190/140 | 1200/1100 |
| K562 | – | + | 320/230 | 60/50 |
| Erythrocytes | ? | ? | 420/— | 68/— |

Figure 14A:
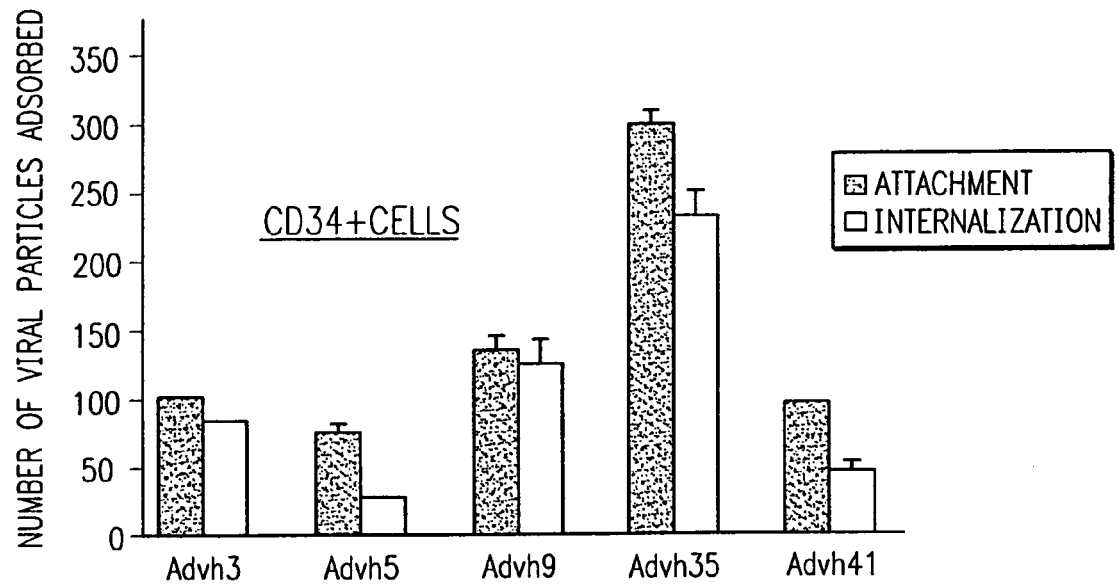
FIGS. 14A and 14B show attachment and internalization of different adenovirus serotypes to CD34+ and K-562 cells respectively.
Figure 14B:
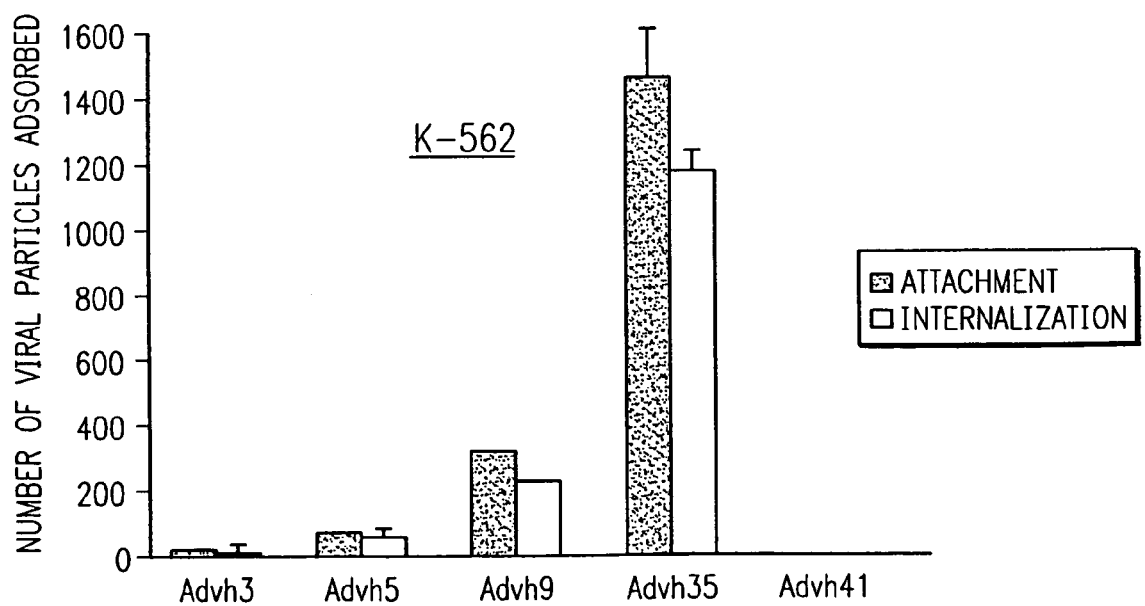

Attachment and Internalization of Adenovirus Serotypes 3, 5, 9, 35 and 41 into Human CD34+ Bone Marrow Cells and K562 Erythroleukemia Cell Line:

Previous studies showed that the human erythroleukemia cell line K562 can be transduced with Ad5-based adenoviral vectors at very high MOIs. As shown in FIG. 14, only about 60 viral particles per cell of adenovirus serotype 5 are attached to and even fewer particles are internalized into these cells at a MOI of 400. In contrast to Ad5, about 320 viral particles per cell of Ad9 and about 1500 viral particles per cell of Ad35 are attached to and about two-thirds of them are internalized into K562 cells (FIG. 14B). Human unstimulated CD34+-enriched bone marrow cells obtained from frozen stocks are incubated overnight in growth medium without cytokine stimulation. The next day, the number of viable cells is calculated. For attachment studies, cells are washed three times with ice-cold PBS, resuspended in adhesion buffer and incubated with adenoviruses. Among the adenoviral serotypes tested, only adenovirus particle of Ad9 (about 150 viral particles per cell) and Ad35 (about 320 viral particles per cell) are able to attach to unstimulated CD34+ cells on the level, compared to Ad 5 (only 60 viral particles per cell). Four-fifths of these virus particles are able to be internalized by the cells. Interestingly, upon stimulation of CD34+ cells with GM-CSF and EPO/TPO for two weeks, attachment and internalization of Ad9 viral particles are significantly increased (up to 300 particles per cell). At the same time, the transient stimulation of cells with GM-CSF for two days could not increase the level of viral attachment to the cells.

Based on the above finding that Ad35 serotype is able to attach and internalize into CD34+ cells most efficiently among several serotypes tested, serotype Ad35 was selected for further studies. As described in Appendix II, a chimeric vector (Ad5 GFP/F35) containing the short-shafted Ad35 fiber sequence in an Ad5 capsid was able to target a broad spectrum of CD34+ cells in a CAR/integrin independent manner.

Discussion

In summary, from all the serotypes tested, Ad9, Ad3, and Ad35 demonstrated the most efficient attachment to and internalization with K562 and CD34+ cells. Based on adsorption/internalization data, Ad9 and Ad35 as representatives for subgroups D and B were selected for further tropism studies.

D. Characterization of Ad Vector Replication in K562 and CD34+ Cells.

Comparative analysis of Ad5, and Ad9 and Ad34 to infect and to replicate in 293, K562 and CD34+ cells. The ability of the Ad9 fiber knob domain to recognize the same primary receptor on the cell surface as Ad5 with comparable affinity was described earlier. Thus, the finding that Ad9 viral particles can only poorly attach to 293 cells is rather unexpected. In order to find out how the attachment and internalization data reflect the biological activity of adenoviruses of different serotypes, the stocks of Ad5, Ad9 and Ad35 are characterized in more detail by electron microscopy, plaque assay on 293 cells, and quantitative replication assay in K562 and CD34+ cells.

Methods

Quantitative Replication Assay:

$1 \times 10^5$ CD34+ or K562 cells were infected in 100 µl of growth media with different MOIs of Ad5, 9, or 35 which had been amplified in 293 cells, expressing the XhoI DNA methyltransferase isoshizomer PaeR7 (Nelson, J., Kay, M. A. 1997. *Journal of Virology.* 71:8902–8907). After 2 hours of incubation at 37° C., the cells were centrifuged at 1000×g for 5 min, the virus-containing medium was removed, the cells were resuspended in 100 µl of fresh media, and then they were incubated at 37° C. until harvesting. At 16 hours post-infection for K562 cells, or 36 h post-infection for CD34+ cells, 5 µg of pBS (Stratagene, La Jolla, Calif.) plasmid DNA was added as a carrier which could also be used as a loading control. Genomic DNA was extracted as described previously (Lieber, A., C.-Y. et al. 1996. *Journal of Virology.* 70:8944–8960). One-fourth of purified cellular DNA (equivalent to $2.5 \times 10^4$ cells) was digested with HindIII, XhoI, or with HindIII and XhoI together at 37° C. overnight and subsequently separated in a 1% agarose gel followed by Southern blot with chimeric Ad5/9 or Ad5/35 DNA probes. The chimeric probes, containing sequences of Ad5 and Ad9 (Ad 5/9) or Ad5 and Ad35 (Ad 5/35), were generated by a two-step PCR amplification using Pfu-Turbo DNA polymerase (Stratagene, La Jolla, Calif.) and viral DNA from purified particles as a template. The following primers were used for PCR (Ad5 sequences and nucleotide numbers are underlined): Ad5F1-(nt: 32775–32805) 5'-GCC CAA GAA TAA AGA ATC GTT TGT GTT ATG-3' (SEQ ID NO.: 3): Ad5R1-(nt: 33651–33621) 5'-AGC TGG TCT AGA ATG GTG GTG GAT GGC GCC A-3' (SEQ ID NO.:4): chimeric Ad5/9F-(nt: 31150–31177, nt: 181–208) 5'-AAT GGG TTT CAA GAG AGT CCC CCT GGA GTC CTG TCA CTC AAA CTA GCT GAC CCA-3' (SEQ ID NO.: 5): chimeric Ad5/9R-(nt: 32805–32775, nt:1149–1113) 5'-CAT AAC ACA AAC GAT TCT TTA TTC TTG GGC TTC ATT CTT GGG CGA TAT AGG AAA AGG-3' (SEQ ID NO.:6); chimeric Ad5/35F-(nt: 31150–31177, nt: 132–159) 5'-AAT GGG TTT CAA GAG AGT CCC CCT GGA GTT CTT ACT TTA AAA TGT TTA ACC CCA-3' (SEQ ID NO.:7), chimeric Ad5/35R (nt: 32805–32775, nt: 991–958) 5'-CAT AAC ACA AAC GAT TCT TTA TTC TTG GGC ATT TTA GTT GTC GTC TTC TGT AAT GTA AG-3' (SEQ ID NO.:8). Nucleotide numbers are given according to the sequences obtained from the NCBI GenBank (accession No. M73260/M29978 for Ad5, X74659 for Ad9, and U10272 for Ad35). After the first amplification, the 968 bp-long Ad9, a 859 bp-long Ad35 DNA fragments corresponding to the fiber genes, and a 876 bp-long Ad5 fragment corresponding to the Ad5 E4 region (located immediately downstream of Ad5 fiber gene) were purified by agarose gel electrophoresis. To generate chimeric DNA probes, amplified Ad5 DNA was mixed with Ad9 or Ad35 fragments obtained during the first step of PCR, and subjected to a second PCR amplification using Ad5/9F or Ad5/35F primers and the Ad5R1 primer. The resulting Ad5/9 or Ad5/35 chimeric DNA fragments (see FIG. 15) were purified and their concentrations were measured spectrophotometrically. Corresponding chimeric DNA fragments were loaded as concentration standards on agarose gels or labeled with $[^{32}P]$-dCTP and used as probes for Southern analysis. The number of viral genomes per DNA sample was calculated after quantitative Phosphoimager analysis. In preliminary experiments, no preferential hybridization of chimeric DNA probes to DNA of any particular viral serotype was detected.

Results

Replication of Selected Serotypes in K562 and CD34+ Cells:

Adsorption/internalization studies do not ultimately prove viral transduction, a process often defined as gene transfer that allows for viral or heterologous gene expression in host cells. Intracellular trafficking, including endosomal lysis, transport to the nucleus, and nuclear import of the viral genome, depends on structural capsid proteins and thus, varies between different serotypes (Defer, C., et al., P. 1990. *J. Virology.* 64:3661–3673; Miyazawa, et al. 1999. *J. Virology.* 73:6056–6065). We believed that analysis of viral gene expression would be a means to verify successful nuclear import of viral genomes and that this would be a good criterion for selection of serotypes able to efficiently infect our target cells. To do this, we used a protocol, which allows for the detection of Ad replication in infected cells. Viral DNA synthesis can only occur after de novo expression of adenoviral early genes. We utilized a site-specific methylation strategy to monitor viral DNA replication within infected cells, (Nelson, J., Kay, M. A. 1997. *Journal of Virology.* 71:8902–8907). Methylated Ad serotypes were produced by the addition of a methyl group onto the N6 position of the adenine base of Xho I sites, CTCGAG, during propagation of the viruses in 293 cells expressing the Xho I isoschizomer PaeR 7 methyltransferase (PMT) (Kwoh, T. J., et al. 1986. *Proc. Natl. Acad. Sci. USA.* 83:7713–7717) (293 PMTcells). Loss of methylation through viral replication restores Xho I cleavage and can be detected by Southern blots of Xho I-digested genomic DNA from infected cells.

Figure 15A:
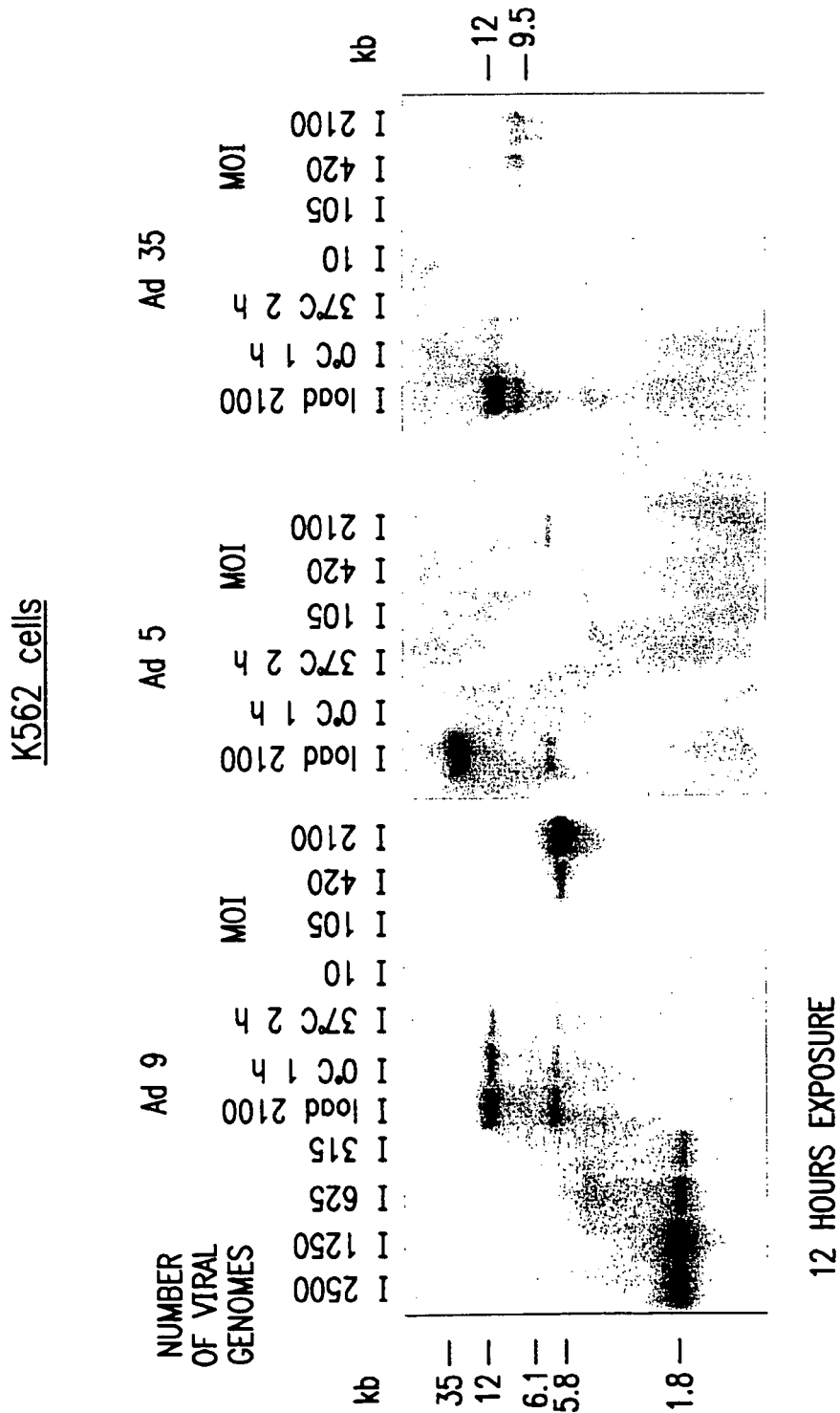
FIGS. 15A–15C shows the analysis of viral replication in K562 and CD34+ cells by Southern blot analysis of methylated viral DNA. Replication studies were performed with $1 \times 10^5$ K562 cells (A) or CD34+ cells (B), infected with methylated Ad5, Ad9 or Ad35. The lane labeled as "load" represents DNA that was extracted form the media/cell mixture immediately after adding the indicated viral dose to cells. The intensities of bands corresponding to methylated and un-methylated viral DNA indicate that ~85% of the input virus was methylated. To quantify adsorption and internalization, DNA analysis was performed after prior incubation of virus with cells at 0° C. (adsorption) or 37° C. (internalization). For dose dependent replication studies, the indicated viral dose (expressed as the number of genomes) was added to the cells, and cellular genomic DNA together with viral DNA was extracted 16 hours or 36 hours post-infection for K562 and CD34+ cells, respectively. Identical amounts of sample DNA were analyzed by Southern blot. For quantification purposes, Ad9 replication was analyzed together with Ad5 using an Ad5/9 chimeric probe that hybridizes with DNA of both serotypes (C). The analysis of Ad5 versus Ad35 replication was performed with the corresponding Ad5/35 chimeric probe. Since separate hybridizations with both Ad5/35 and Ad5/9 probes gave identical signal intensities for Ad5 DNA only one panel is shown for Ad5 replication in test cells. To produce distinguishable fragments specific for the methylated or non-methylated status of viral genomes, Ad5 DNA was digested with Xho I, while Ad9 and Ad35 DNA was digested with Xho I and Hind III. The bands specific for methylated (not-replicated) viral DNA were ~12 kb for Ad9, 35 kb for Ad5, and ~12 kb for Ad35. The fragments specific for non-methylated DNA were 5.8 kb for Ad9, 6.1 kb for Ad5, and 9.5 kb for Ad35. Chimeric Ad5/9 and Ad5/35 DNA fragments (1.8 kb) were used as quantification standards and applied onto gel together with digested viral/cellular DNA (shown on the left part of the figures).
Figure 15B:
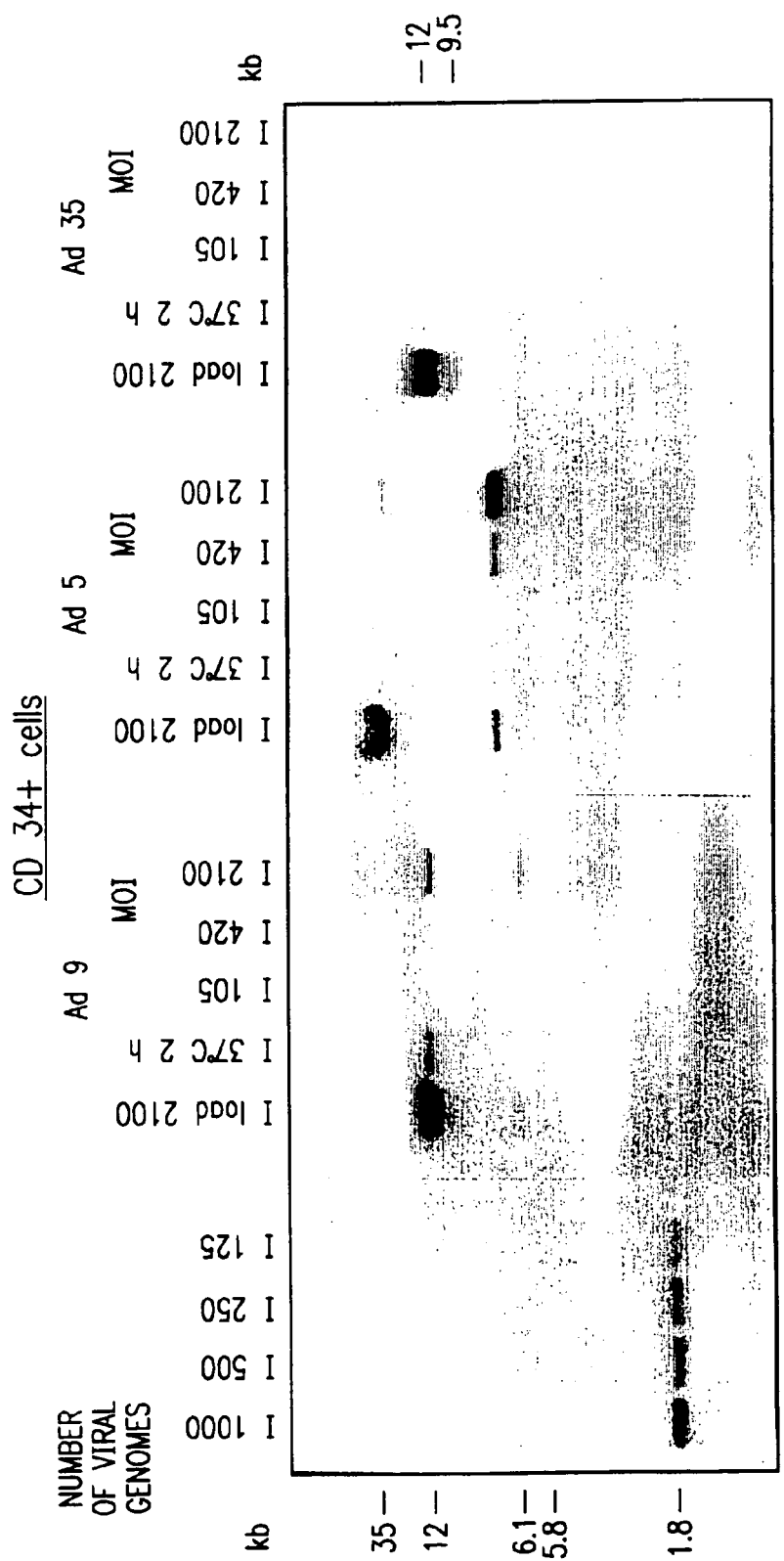
Figure 15C:

Ad replication studies were performed in K562 and CD34+ cells with Ad9 and Ad35, in comparison to Ad5. For replication studies, the infectious titer (in pfu/ml) and genome titer (in genomes per ml) were determined (by plaque assay on 293 cells or by quantitative Southern blot, respectively) for methylated and unmethylated Ad5, Ad9, and Ad35 (Table 2). The ratio of pfu to genome titer was comparable for methylated and unmethylated virus demonstrating that DNA methylation had not altered transduction properties. About 85% of (Ad5, 9, and 35) virus used for infection was methylated as calculated based on the intensity of fragments specific for methylated and non-methylated viral DNA present in the viral load (FIG. 15). The numbers of genomes detected after adsorption (1 hour, 0° C.) or internalization (2 hours 37° C.) correlated well with studies shown in FIG. 12. Ad9 and Ad35 interacted more efficiently than Ad5 with K562 and CD34+ cells. Dose-dependent replication studies in K562 and CD34+ cells were performed with the same genome numbers of Ad5, 9, and 35 (FIG. 15). The replication rate was measured based on the ratio of methylated to demethylated viral DNA after infection with different MOIs (2100, 420, and 105 genomes per cell). In K562 cells, efficient replication (100% conversion from methylated to unmethylated DNA) was detected for Ad5 at MOI>/=2100, for Ad9 at MOI>/=420, and for Ad35 at MOI>/=105. This demonstrated that Ad35 transduced K562 cells with the highest efficiency. In CD34+ cells, the replication rate was 100% for Ad5 and 31% for Ad9 after infection with MOI 420. Although methylated Ad35 viral DNA was present in CD34+ cells, viral replication was undetectable for Ad35. In summary, while viral replication studies in K562 cells confirmed data obtained for Ad5, 9, and 35 adsorption and internalization, there was a discrepancy between earlier results and the poor replication of Ad9 and, particularly, Ad35 in CD34+ cells. As outlined later, replication analysis in heterogeneous cell populations, like CD34+ cells, may not allow for definitive conclusions on tropism of a particular serotype.

Taking all the screening data together, Ad9 and Ad35 emerged as the variants with the strongest tropism for K562 and CD34+ cells. It is thought that Ad9 can bind to CAR, however, it preferentially uses $\alpha_v$-integrins for cell entry (Roelvink, P. W., et al. 1996. *J Virology.* 70:7614–7621). This entry strategy may be not optimal for efficient infection of CD34+ cells as only less that 17% of them express $\alpha_v$-integrins (FIG. 10). Therefore, we decided to concentrate on Ad35 as a source for heterologous fiber to be used for construction of a chimeric vector based on an Ad5 backbone.

TABLE IV

Results from the infectivity assay which determines the optical particle-to-PFU (OPU/PFU) ratio using 293 cells

| Virus | OPU (A260) | PFU | OPU/PFU ratio |
|---|---|---|---|
| Ad5 | $1.4 \times 10^{12}$ | $1.06 \times 10^{11}$ | 13 |
| Ad9 | $4.61 \times 10^{11}$ | $2.6 \times 10^{8}$ | 1773 |

Discussion

Viral replication studies in K562 cells confirmed the data obtained for Ad5, 9, and 35 adsorption and internalization. However, there was a discrepancy between the interaction data and the replication data in CD34+ cells where Ad9 replicated only poorly and no replication was seen for Ad35. Ad replication is only initiated upon the production of a critical threshold of early viral proteins, which in turn, is directly dependent on the number of viral genomes present in the nuclei of infected cells. Therefore, the outcome of replication studies may be affected by the rate of nuclear import of viral genomes, by the activity of viral promoters, and/or the intracellular stability of viral DNA/RNA. These parameters may vary, on one hand, between different subsets of CD34+, and/or, on the other hand, between different Ad serotypes. In conclusion, the viral replication analyses performed with different Ad serotypes in CD34+ cells may not predict the actual transduction properties of chimeric vectors based on Ad5 backbone. This implies that attempts to produce gene transfer vectors based on Ad genomes other than Ad5 should be exercised with caution.

Recently, an Ad serotype screening strategy was used to identify variants with tropism for primary fetal rat CNS cortex cells or human umbilical vein endothelial cells. The optimal serotype (Ad17) was selected based on immunohistochemistry for hexon production 48 hours after infection (Chillon, M., et al. 1999. *J. Virology.* 73:2537–2540). However, this approach is problematic because, at least in our hands, antibodies developed against Ad5 hexon did not cross-react with other serotypes. Also, hexon is expressed only after onset of replication. As outlined above, the kinetics of intracellular trafficking, viral gene expression, and replication significantly vary between serotypes (Defer, C., et al., P. 1990. *J. Virology.* 64:3661–3673; Miyazawa, et al. 1999. *J. Virology.* 73:6056–6065).

In addition to being the most efficient serotype in terms of interaction with CD34+ cells, Ad35 is also interesting because it interacts with receptor/s different from the Ad5 and Ad3. Ad35 and Ad5GFP/F35 attachment was not inhibited by Ad5 or anti-CAR antibodies suggesting that Ad35 binding was CAR independent. First, Ad5 did not compete with Ad35 and Ad5GFP/F35 during internalization and infection indicating that $\alpha_\omega\beta_{3/5}$ integrins are not involved in viral entry. Second, function-blocking antibodies against $\alpha_v$-integrins did not compete with Ad35 and Ad5GFP/F35 for internalization into K562 cells, whereas these antibodies did inhibit Ad5 internalization. And third, in contrast to Ad5 based vectors, GFP expression after infection with Ad5GFP/F35 was not restricted to $\alpha_v$-integrin-expressing CD34+ cells. From these facts, we conclude that infection with Ad35 and the chimeric Ad5GFP/F35 vector does not involve $\alpha_v$-integrins. In this context, the presence or absence of RGD motifs within Ad35 penton base remains to be determined by sequencing the corresponding genome region. Cross-competition assays demonstrated that Ad35 and Ad5GFP/F35 bind to a receptor that is different from the Ad3 receptor. Although Ad3 and 35 belong to the same subgroup, they have been divided into two DNA homology clusters, B1 and B2; the amino acids composing their fibers are only 60% homologous. Furthermore, the target tissues for both viruses are different; Ad3 can cause acute respiratory infections, whereas Ad35 is associated with kidney infection (Horwitz, M. S. 1996. *Adenoviruses, p.* 2149–2171. In B. N. Fields, Knipe, D. M., Howley, P. M. (ed.), *Virology, Vol.* 2. Lippincott-Raven Publishers Inc., Philadelphia). Therefore, it was not surprising to see that Ad3 and Ad35 recognize different receptors.

In conclusion, Ad35 and the chimeric vector enter the cells by a CAR- and $\alpha_v$-integrin independent pathway. We believe that Ad35 and the chimeric vector binds primarily to its fiber receptor and that this interaction is sufficient to trigger internalization. On the other hand, Ad35 internalization may involve cellular proteins other than $\alpha_v$-integrins. These membrane proteins can overlap with those for Ad3 internalization and represent $\beta 2$ integrins, which protrude more from the cell surface than $\alpha_v$-integrins (Huang, S., et al. 1996. *J. Virology.* 70:4502–4508).

According to EM studies of negative contrast-stained adenoviral suspensions, the percentage of deficient particles for all adenoviral serotypes tested does not exceed 5%. However, plaque assays reveal that the ability to form plaques in 293 cells is significantly different for tested serotypes. The optical particle-to-PFU (OPU/PFU) ratio obtained is 13 for Ad5, which is in good agreement with the previously estimated ratio for this adenoviral serotype. Importantly, this ratio is about three times higher for adenovirus serotype 35 and more than 150-fold higher for adenovirus serotype 9. Furthermore, quantitative Southern blot using chimeric Ad5/9 and Ad5/35 DNA probes is used to determine the ratio between the genome and transducing titer. This study confirms the data obtained by plaque assay. Quantitative replication assay of these adenoviruses in K562 and CD34+ cells also confirms the ability of Ad9 and Ad34 to more efficiently attach to these cell types. The replication of viral genomes is observed for Ad9 and Ad34 at lower MOIs of infection, compared to Ad5. In conclusion, the data obtained for different serotypes in attachment and internalization are in good agreement with the infectivity data in target cells.

E. Attachment and Internalization of Different Adenoviral Serotypes into Primary Dendritic Cells, JAWSII, MCF-7 and REVC Cells.

As a proof of principle, the serotype screening strategy can be employed for other important target cells which are refractory to Ad5 infection.

Results

RECV cells are endothelial cells which have to be targeted for approaches that are aimed to gene therapy of restenosis, atherosclerosis, inflammation etc. MCF-7 cells are breast cancer cells isolated from liver metastases which are important targets for tumor gene therapy. The human adenovirus serotypes 3, 5, 9, 35 and 41 are tested to see whether they can attach to and can be internalized by mouse primary dendritic cells, JAWSII cells, MCF-7-human breast cancer cells and REVC endothelial cells. None of the adenoviral serotype tested can efficiently attach to primary dendritic cells. Adenovirus serotype 3 is able to efficiently attach to REVC endothelial cells (about 400 virus particles per cell are attached and about 300 are internalized). In comparison, only 50 Ad5 particles are able to attach to and even fewer are internalized in these REVC. The human breast cancer cells (MCF-7) are previously shown to be refractory to Ad5 infection at low MOIs. However, Ad3 and more efficiently, Ad35 attach to and internalize into MCF-7 cells.

Discussion

The data presented herein indicate that different human adenovirus serotypes recognize different cellular receptors and can therefore infect cell types that are refractory to Ad5 infection. There are adenoviral serotypes that can more efficiently attach and internalize than Ad5 for human CD34+ cells, REVC, K562 and MCF-7 cells. This finding provides a basis for the construction of chimeric adenoviral vectors which are Ad5 vectors containing receptor ligands derived from other serotypes.

F. Infection Studies on Primary Human Bone Marrow Cells.

Since established erythroleukemic cell lines do not represent an adequate model for the ultimate hematopoietic stem cell that has to be targeted in patients in order to achieve long-term reconstitution with genetically modified cells, normal primary human bone marrow cells are used for the initial infection/retargeting studies.

Results

In a first set of tropism studies with different Ad serotypes, whole bone marrow cell suspensions can be used without preselection. This is advantageous because the tropsim of various adenovirus serotypes or genetically retargeted vectors can be analyzed on a broad spectrum of progenitor subpopulations representing myeloid, erythroid, megakaryocytic, lymphoid, dentritic, and monocytic lineages. For short term (<5 hours) infection studies, bone marrow suspensions can be cultured in IMDM supplemented with 10% FCS, β-mercaptoethanol, and 10 u/ml IL-3 for ensuring cell viability.

Mononucleated Cell Assays:

Mononucleated bone marrow cells can be incubated with MOI 1, 10, 100, or 1000 pfu/cell of the various adenovirus types for a short time. Paraffin sections or cytospins of infected bone marrow cells can be analyzed for nuclear-localized, labeled viral DNA. BrdU labeling can be visualized by immunoflouresence with anti-BrdU antibodies; $^{32}$P-tagged viral DNA can be detected by incubation with photo-emulsion. In addition, the same cell material can be analyzed for morphology after specific histo-staining (e.g. Wright, Hemo3 staining). If required, commercially available antibodies can be used to specific cell surface markers conjugated directly to different fluorochromes (FITC (green), TRIT., RPE, (red), RPE-Cy5, AMCA (blue)) to completely characterize infected bone marrow subpopulations. Colocalization of BrdU-labeled viral DNA (e.g. as FITC signal) with membrane markers signifying infection of specific cell types can be demonstrated; for example, potential stem cells/early progenitors ($CD34^+$, $CD38^-$), megakaryocytes (CD41a+), eryhthroid cells (glycophorin A+), dendritic cells (CD1a+), monocytes (CD14+), or myeloid cells (CD15+), etc. The morphological analysis of infected bone marrow subsets gives a first information whether specific adenovirus serotypes can target primitive cell types.

Discussion

Since the different wild-type adenoviruses do not express a uniform marker gene and do not integrate and since detection of tagged viral DNA cannot be done on live cells, it is not possible, at this point, to characterize infected cells for clonogenic or repopulation capacities. Therefore, adenovirus serotypes for retargeting studies are selected, based on their ability to infect in vitro purified CD34+ cells at low MOIs. This subset of bone marrow cells is known to contain long-term reconstituting cells. Infection studies with different adenovirus serotypes can be repeated on purified CD34+ cells, (cultured in IMDM+10% FCS, α-mercaptoethanol, and 10 units/ml IL-3) as described above. Purification of CD34+ cells can be performed by direct immunoadherence on anti-CD34 monoclonal antibody-coated plates or on MiniMacs columns as described by Papyannopoulou (Papayannopoulou, T. et al., 1996, *Experimental Hematology*, 24:660–69; Papayannopoulou, T. et al., 1993, *Blood*, 81:229). The purity of isolated CDC34+ cells ranges routinely from 80–95%. Analgous infection studies can be repeated with selected adenovirus types on CD34+/CD38− subsets.

To confirm productive infection purified CD34+ cells can be infected with selected (methylase-tagged) serotypes and analyze viral DNA replication. Cultures of purified human bone marrow CD34+ cells can be used for the transduction and integration studies as a model for HSCs.

It was recently demonstrated that HSC activity does exist in CD34-negative human bone marrow subsets (Bathia, M. et al., 1998, *Nature Medicine*, 4; 1038–45; Osawa, M., et al., 1996, *Science*, 273:242–5; Goodell, M. et al., 1997, *Nature Medicine*, 3:1337–45; Zanjani, E. D. et al., 1998, *Exp. Hematology*, 26:353–60). Lin$^-$CD34$^-$38$^-$ cells can be tested in the retargeting and transduction studies in combination with repopulation assays in SCID-NOD mice.

G. Cloning and Insertion of the Fiber Gene.

Methods

PCR-Cloning of the Corresponding Fiber Gene and Insertion into Ad5 Based Shuttle Plasmids Instead of the Endogenous AD5 Fiber:

One or several adenoviruses with tropism to CD34+ or other HSC containing population is selected for further studies described herein. The complete coding region for fiber varies between 1–2 kb, depending on the virus type. The fiber encoding sequences can be obtained by PCR with Pfu polymerase from viral DNA isolated from purified particles of the selected virus types. The corresponding primers can be designed based on the fiber sequences available from the EMBL gene bank. The PCR products are cloned as PacI-BalI fragment into pCD4 (FIG. 10), a shuttle vector for recombination of RecA+*E. coli*. In pCD4, the heterologous fiber gene is flanked on both sides with Ad5 sequences, which are homologous to regions directly adjacent to the fiber reading frame in Ad5. As an Ad5 (shuttle vector) derived template for recombination, pCD1, a pBHG 10 (Microbix, Toronto, Canada) derivative can be used. The recombination procedure is performed according to a protocol routinely used for recombinant adenovirus generation (Chartier, C., et al., 1996, *J. of Virology*, 70, 4805–4810). Routinely, 90% of the resulting plasmids are accurately recombined. The junctions between the heterologous fiber (X) and Ad5 sequences can be sequenced to confirm the accuracy of recombination. The resulting plasmid is named pAd5fiberX (pAd5$^{fx}$). The resulting product is used to generate pAd5$^{fx}$-based Ad.AAV containing the heterologous fiber gene.

Construction of Chimeric Ad Vectors:

For transduction studies, two Ad vectors were constructed: Ad5GFP and Ad5GFP/F35, containing a chimeric Ad5/35 fiber gene. Both adenoviral vectors contained a 2.3 kb, CMV promoter driven EGFP gene [derived from pEGFP-1, (Clontech, Palo Alto, Calif.)] inserted into the E3 region of Ads. The EGFP expression cassette was cloned between Ad5 sequences 25,191–28,191 and 30,818–32,507 into a shuttle plasmid, which contained the E3 deletion described for pBHG10 (Microbix, Toronto, Canada). The resulting plasmid was named pAdGFP. For the chimeric vector, the Ad5 fiber gene in pAdGFP was substituted by an Ad5/35 chimeric fiber gene generated by the two-step PCR protocol outlined above. In the first PCR step, three DNA fragments corresponding to i) the Ad5 fiber 5'-nontranslated region and the first 132 bp of the fiber tail domain (nt 30,818–31,174), ii) the Ad35 shaft and knob domains (nt 132–991), and iii) the Ad5 E4 region including the Ad5 fiber polyadenylation signal (nt 32,775–33,651 were amplified by Pfu-Turbo DNA polymerase. The following primers were used: for the Ad5 tail, Ad5F-2 (nt 30,798–30,825) 5'-CGC GAT ATC GAT TGG ATC CAT TAA CTA-3' (SEQ ID NO.: 9) and Ad5R-2 (nt 31,174–31,153) 5'-CAG GGG GAC TCT CTT GAA ACC CAT T-3' (SEQ ID NO.: 10); for the Ad35 shaft and knob, primers Ad5/35F and Ad5/35R (see above); for the Ad5E4 and polyA, primers Ad5F-1 and Ad5R-1 (see above). After 10 PCR cycles, the products were purified by agarose gel electrophoresis, combined, and then subjected to a second PCR with primers Ad5F-2 and Ad5R-1. The resulting 2115 bp-long chimeric fiber gene contained the Ad5 tail and the Ad35 shaft and knob domains. This product was used as a substitute for the SalI/XbaI Ad5 fiber gene containing fragment in pAdGFP. The resulting plasmid was named pAdGFP/F35. To generate full-length E1/E3 vector genomes, pAdGFP and pAdGFP/F35 were inserted in pAdHM4 (Mizuguchi, H., Kay, M. A. 1998. *Human Gene Therapy*. 9:2577–2583) by recombination in *E. coli* (Chartier, C., E. et al. 1996. *Journal of Virology*. 70:4805–4810). To do this, the RecA+*E. coli* strain BJ5183 was co-transformed with pAdHM4 linearized by SrfI mixed with the XbaI fragments containing the GFP genes, the Ad5 or Ad5/35 fiber genes, and the Ad5 homology regions. The resulting recombinants were analyzed by restriction analysis. Correct recombinants were amplified in *E. coli* HB101 and purified by double CsCl gradient banding. The plasmids were named pAd5GFP and pAd5GFP/F35. The correct structure of the Ad5/35 chimeric fiber gene was confirmed by endonuclease digestion and sequencing part of pAd5GFP/F35. To produce the corresponding viruses, pAd5GFP and pAd5GFP/F35 were digested with PacI to release the viral genomes and transfected onto 293 cells as described (Lieber, A., C.-Y. et al. 1996. *Journal of Virology*. 70:8944–8960). Plaques developed 7 to 10 days post-transfection in overlayed cultures. Recombinant viruses were propagated in 293 cells and purified by standard methods described elsewhere (Lieber, A., C.-Y. et al. 1996. *Journal of Virology*. 70:8944–8960).

Hemagglutination Assay:

Twenty-five microliters of serial dilutions of Ad5, Ad35, or chimeric Ad5GFP/F35 virions in McIlvaine-NaCl buffer (0.1 M citric acid, 0.2 M $Na_2HPO_4$ [pH 7.2], diluted 1:50 with 0.87% NaCl) were loaded onto 96 well plates. To each dilution, 25 µl of a 1% suspension of monkey erythrocytes (in McIlvaine-NaCl buffer) was added. The sedimentation pattern was determined after incubation for 1 hour at 37° C. All tests were performed in quadruplicates in at least two independent experiments.

Southern Blot:

Extraction of genomic DNA, labeling of DNA fragments and hybridization were performed as described earlier (Lieber, A., C.-Y. et al. 1996. *Journal of Virology*. 70:8944–8960).

Results

Figure 16A:
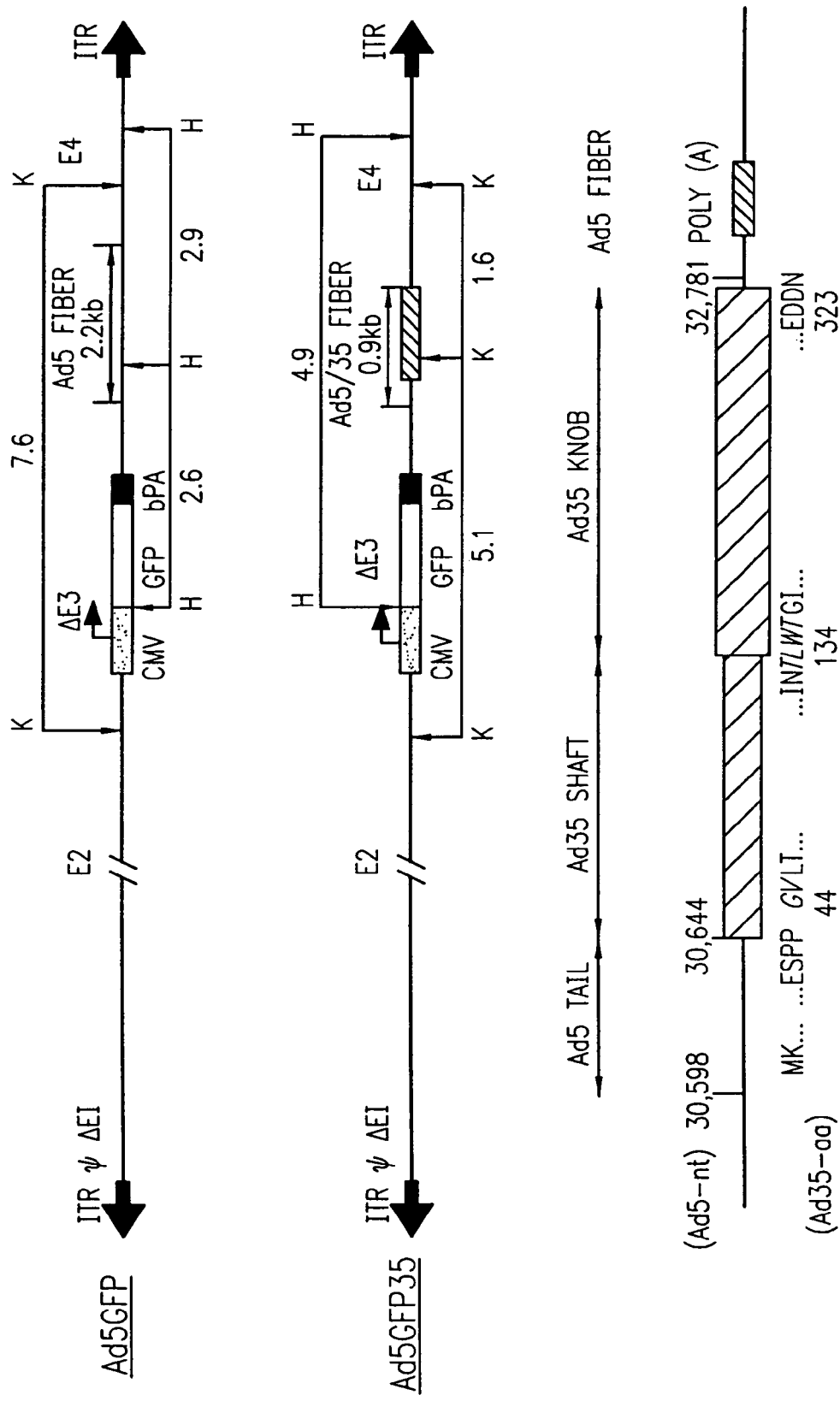
FIGS. 16A–16B shows the structure of Ad5GFP and chimeric Ad5GFP/F35 vectors. A) Schematic diagram of the original E1/E3 deleted Ad5-based vector with GFP-expression cassette inserted into the E3 region (Ad5GFP) and the chimeric vector Ad5GFP/F35 containing the Ad5/35 fiber gene. The 2.2 kb Ad5 fiber gene was replaced by a 0.9 kb chimeric fiber gene encoding for the short shaft and knob of Ad35 by a technique that involved PCR-cloning and recombination in E. coli. Kpn I (K) and Hind III (H) sites localized within or around the fiber genes are indicated. The lower panel shows the detailed structure of the chimeric fiber region. The Ad5 fiber tail [amino acids (aa): 1–44] were joined in frame to the Ad35 fiber shaft starting from its first two amino acids (GV), which are conserved among many serotypes. A conserved stretch of amino acids TLWT marks the boundary between the last α-sheet of Ad35 shaft and the globular knob. The Ad35 fiber chain termination codon is followed by the Ad5 fiber poly-adenylation signal. The region of Ad5GFP/F35 encoding for chimeric fiber was completely sequenced with Ad5 specific primers (see Material and Methods). B) Restriction analysis of viral genomes. Viral DNA was isolated from purified Ad5GFP and Ad5GFP/F35 particles as described elsewhere. One microgram of DNA was digested with Hind III or Kpn I and separated in ethidium bromide stained agarose gels (left panel) which were subsequently blotted and analyzed by Southern blot with an Ad5 E4 specific probe (nt 32,7775–33, 651) (right panel). Specific patterns, designating the correct structure for both viral vectors were detected. The Hind III fragments specific for Ad5GFP and Ad5GFP/F35 were 2.9 kb and 4.9 kb, respectively. The Kpn I fragment that confirmed the correct Ad5GFP/F35 structure was 1.6 kb compared to a 7.6 kb Ad5GFP fragment. M-1 kb ladder (Gibco-BRL, Grand Island, N.Y.).
Figure 16B:
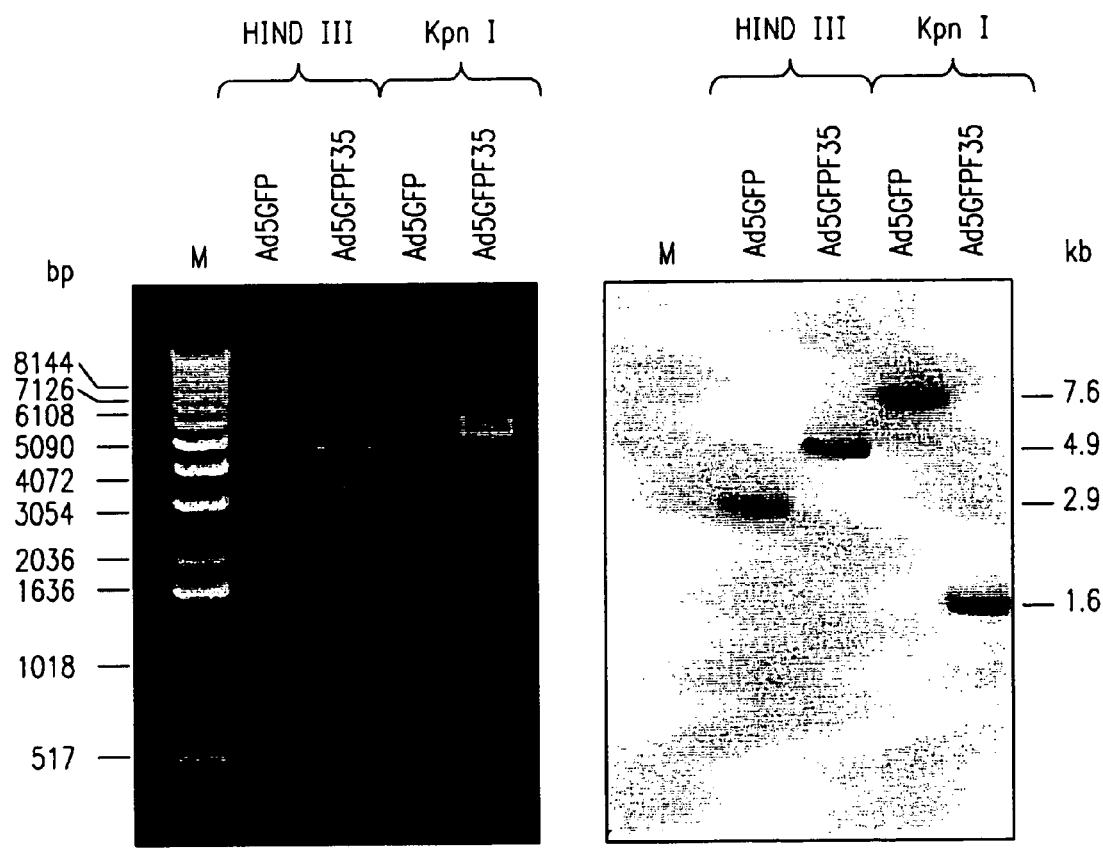

Construction/Characterization of Chimeric Fiber:

Previously, it has been shown that exchanging the fiber knob was sufficient to alter the tropism of chimeric Ad vectors (Chillon, M., et al. 1999. *J. Virology*. 73:2537–2540; Krasnykh, V., et al. 1998. *J. Virology*. 72:1844–1852; Stevenson, S. C., et al. 1997. *J. Virology*. 71:4782–4790). As outlined above, the length of the fiber shaft may critically determine the entry strategy of a particular serotype. Therefore, we decided to replace not only the Ad5 fiber knob but also the shaft. The chimeric Ad5/35 fiber contained the Ad5 tail (amino acid: 1–44) necessary for interaction with the Ad5 penton base linked to 279 amino acids from Ad35 including the shaft with 7β-sheets and the knob (FIG. 16A). The endogenous Ad5 fiber polyA signal was used to terminate transcription of the chimeric fiber RNA. The combination of the Ad5 capsid including the RGD motif containing penton base with a short-shafted fiber could be risky because the natural distance between the fiber knob and the RGD motifs was disturbed. The Ad5 fiber was substituted by the chimeric fiber sequences based on an E1/E3 deleted Ad vector. This vector carried a CMV promoter-GFP reporter gene cassette inserted into the E3 region. The corresponding chimeric virus (Ad5GFP/F35) was produced in 293 cells at a titer of >2×10$^{12}$ genomes per ml. For comparison, an E1/E3 deleted Ad vector containing the original Ad5 fiber gene and the GFP expression cassette was generated (Ad5GFP). The titer and the ratio of physical to infectious particles was similar between Ad5GFP and Ad5GFP/F35 indicating that the fiber modification did not significantly alter the stability and/or growth properties of the chimeric vector. The correctness of the fiber modification was confirmed by restriction analysis of the Ad5GFP/F35 viral genome followed by Southern blot hybridization (FIG. 16B), direct sequencing of the fiber-coding region, and a functional test for hemagglutination (HA) of monkey erythrocytes. The agglutination of erythrocytes is fiber knob-mediated; it is known that Ad5 does not agglutinate monkey erythrocytes whereas Ad35 efficiently does (Pring-Akerblom, P., et al. 1998. *J. Virology*. 72:2297–2304). In HA tests, Ad5GFP/F35 agglutinated monkey erythrocytes with the same efficiency as Ad35 at dilutions of up to 1:512. In contrast, no hemagglutination was observed with equivalent Ad5 dilutions. This clearly confirmed the functional activity of the chimeric Ad5/35 fiber incorporated into Ad5 capsid.

Generation of chimeric adenoviral vectors (AD.AAV$^{fx}$) with heterologous fiber molecules: Adenoviruses with chimeric Ad5-Ad3 fiber are viable and can be produced at high titers (Krasnykh, V., et al., 1996, *J. of Virology*, 70, 6839–6846; Stevenson, S. C. et al., 1997, *J. Virology*, 71:4782–90). In order to test whether the fiber substitution described herein affects production or stability of adenoviruses, two E1-deleted first-generation, adenoviral vectors are produced with the AAV-βgal cassette in 293 cells using standard protocols. The vector is generated by recombination of pAd.AAV-BG (prepared as in FIG. 17) with pCD1 (containing the endogenous Ad5 fiber) (FIG. 9); the other vector (with heterologous fiber) is the recombination product of pAd.AAV βgal and pAd5fiberX (pAd5$^{fx}$) (FIG. 9). Virus from single plaques is amplified on 293 cells. The production yield per 293 cell can be determined by plaque-titering of 293 cell lysates. It is anticipated that the fiber modification will not critically effect the stability of chimeric vectors. Finally, bone marrow cells can be infected with the retargeted vectors. Two days after infection, live-cell cytometry is performed for β-gal expression using as substrate Fluourescein di-β-D-Galactopyranoside (FDG) (Cantwell, M. J. et al., 1996 *Blood* 88, 4676–4683; Neering, S. et al., 1996, *Blood*, 88:1147–55; Fiering, S. N. et al., 1991, *Cytometry*, 12:291; Mohler, W. et al., 1996, *PNAS*, 93:57) and the infected cells are characterized for morphology and surface markers. Before and during infection, bone marrow cells can be cultured in IMDM/FCS supplemented with thrombopoietin (Tpo), which supports the survival of HSC (Matsunaga, T. et al., 1996, *Blood*, 92:452–61; Papayannopoulou, T. et al., 1996, *Experimental Hematology*, 24:660–69). Alternatively, retargeted vectors can be generated with the AAV-GFP (green fluorescence protein) cassette and perform FACS analysis on transduced cells based on GFP and surface marker expression.

H. Competition Studies of Chimeric Fiber Protein Ad5/35.

Figure 18:
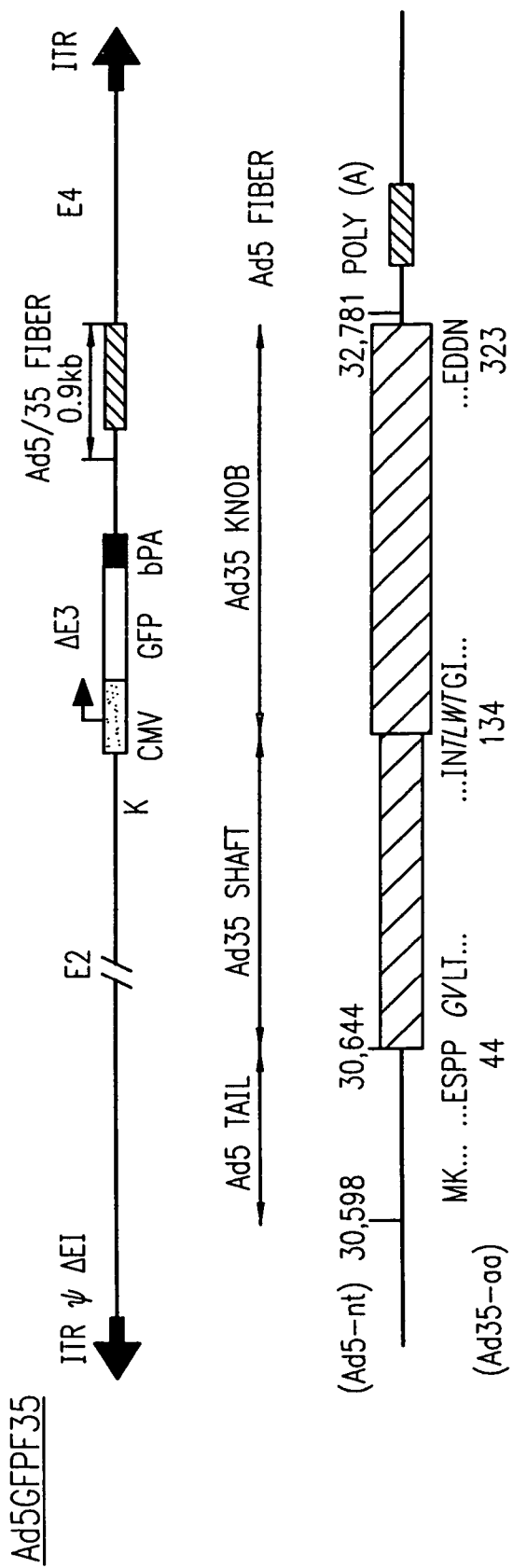
FIG. 18 shows the structure of Ad5/35. Schematic diagram of the original E1/E3 deleted Ad50based vector with GFP-expression cassette inserted into the E3 region (Ad5GFP) and the chimeric vector Ad5GFP/F35 containing the Ad5/35 fiber gene. The 2.2 kb Ad5 fiber gene was replaced by a 0.9 kb chimeric fiber gene encoding for the short shaft and knob of Ad35 by a technique that involved PCR-cloning and recombination in *E. coli* Kpn I (K) and Hind III (H) sites localized within or around the fiber genes are indicated. The lower panel shows the detailed structure of the chimeric fiber region. The Ad5 fiber tail [amino acids (aa): 1–44] were joined in frame to the Ad35 fiber shaft starting from its first two amino acids (GV), which are conserved among many serotypes. A conserved stretch of amino acids TLWT marks the boundary between the last β-sheet of Ad35 shaft and the globular knob. The Ad35 fiber chain termination codon is followed by the Ad5 fiber poly-adenylation signal.
Figure 19A:
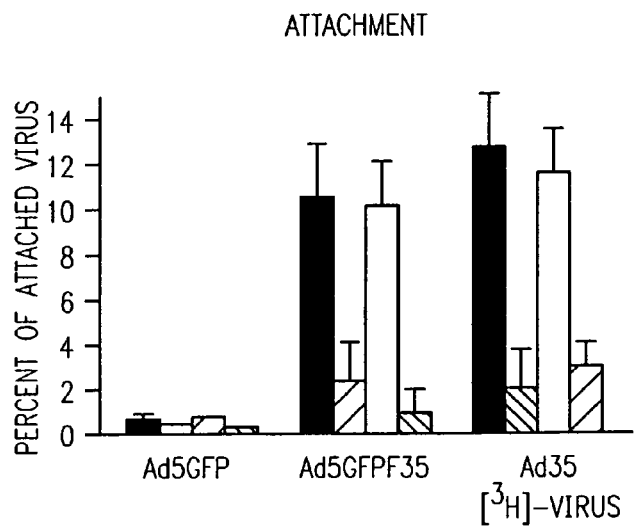
Figure 19B:
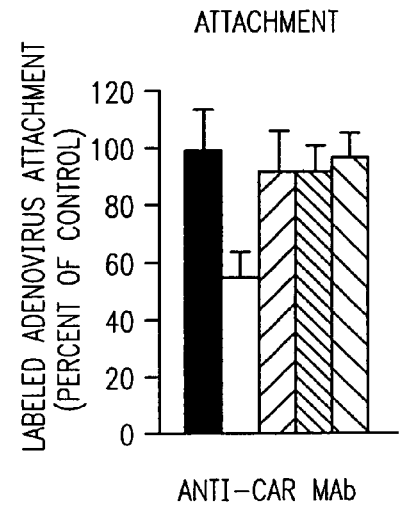
Figure 19C:
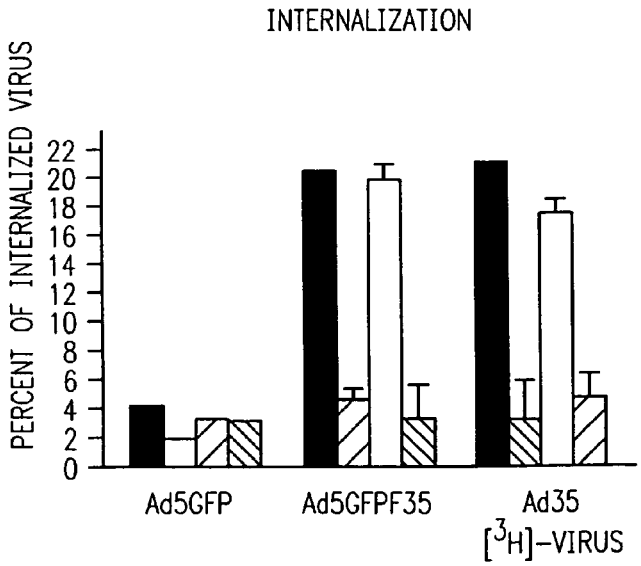
Figure 19D:
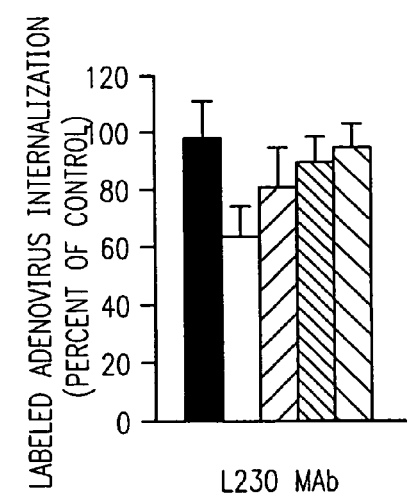

Competition Studies:

Cross-competition studies between Ad5, 35, and Ad5GFP/F35 (FIG. 18) for binding and internalization were performed in order to investigate in more detail the pathways which are used by the chimeric vector to infect target cells. Wild-type Ad35 and the chimeric vector Ad5GFP/F35 could recognize the same primary receptor as they competed with each other for the attachment to K562 cells (FIG. 19A, upper pane). This primary receptor is different from that used by Ad5, since neither Ad5 viral particles nor anti-CAR monoclonal antibodies (FIG. 19B, upper panel) were able to abrogate Ad35 or Ad5GFP/F35 binding. In competition studies for internalization, Ad35 and Ad5GFP/F35 competed with each other with equal efficiency. Ad5 and anti-$\alpha_v$-integrin monoclonal antibodies (L230) (FIGS. 19C, D; lower panel) did not inhibit internalization of Ad35 or the chimeric virus. To consolidate this data, K562 cells were infected with Ad5GFP and Ad5GFP/F35 after prior incubation of cells with anti-CAR or anti-$\alpha_v$-integrins monoclonal antibodies followed by analysis of GFP-expressing cells. The transduction data mirror the results obtained in adsorption/internalization studies. In summary, this demonstrated that Ad35 and Ad5GFP/F35 use a CAR and $\alpha_v$-integrin-independent pathway for infection of K562 cells; the structural elements which account for these specific properties are located within the Ad35 fiber and can be transplanted into Ad5 by fiber substitution.

Figure 20A:
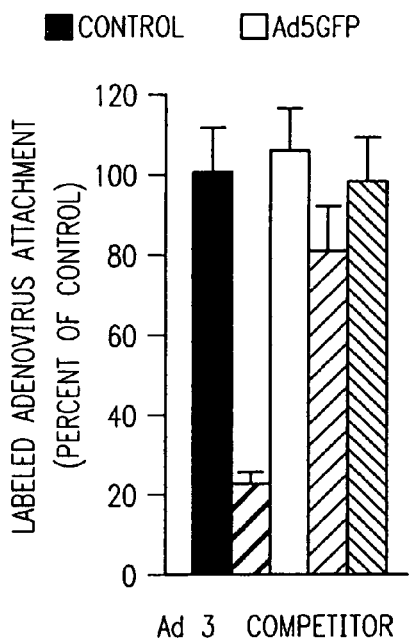
Figure 20B:
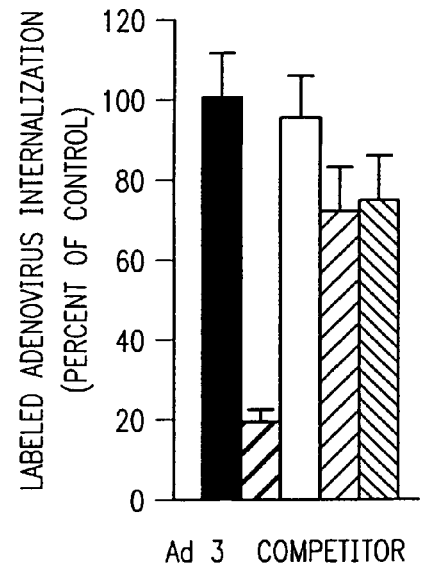
Figure 20C:
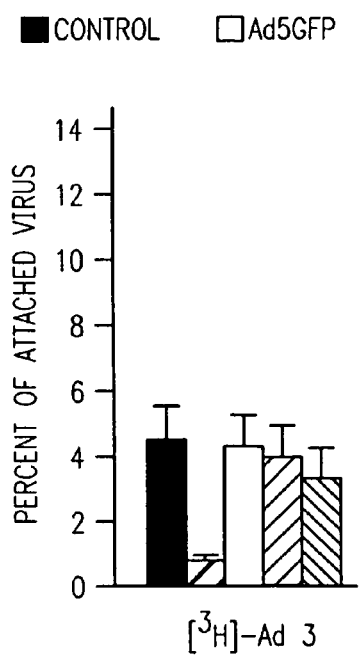
Figure 20D:
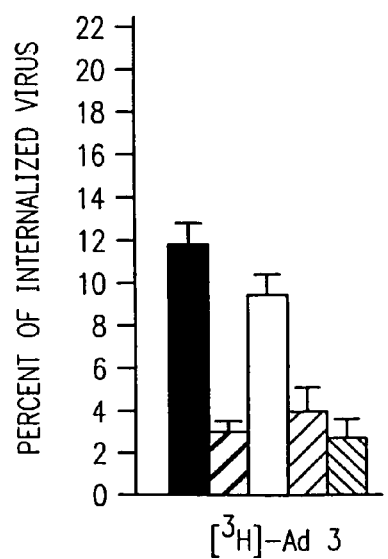

Ad3 can efficiently interact with K562 cells (FIG. 12), although Ad3 and Ad35 belong to the same subgroup (B), the homology between amino acid sequences of their fibers is only about 60%. Therefore, we decided to test whether Ad3 could compete with Ad35 and Ad5GFP/F35 for attachment and internalization (FIG. 20). These studies demonstrated that Ad35 binding was not inhibited by Ad3 indicating the use of different receptors. Interestingly, Ad3 slightly inhibited attachment of Ad5GFP/F35 (FIG. 20A, left panel). In addition to binding to the receptor common for the Ad35 and Ad5GFP/F35 fiber, the chimeric capsid (e.g. the Ad5 penton RGD motifs) may also interacts with a second cellular receptor that overlaps with elements involved in Ad3 binding. In cross-competition for internalization, pre-incubation of cells at 37° C. with Ad35 and with chimeric virus significantly decreased internalization of [$^3$H]-labeled Ad3 (FIG. 20D, right panel). In the reverse experiment, Ad3 as competitor decreased the level of internalization by 30% for both, Ad35 and the chimeric virus (FIG. 20B, right panel). As expected, Ad5 and Ad3 did not compete for adsorption or internalization. As shown before (FIG. 19B), anti-CAR and anti-$\alpha_v$-integrin antibodies did not block Ad3 interaction with K652 cells. In summary, we concluded that Ad35 and Ad5GFP/F35 bind to receptor/s different from that of Ad3, although they can use common structural elements for internalization, which are different from $\alpha_v$-integrins.

Infection Studies with Chimeric Virus:

It is established that Ad5GFP/F35 infected K562 cells by a CAR and $\alpha_v$-independent pathway. It is possible that this property allows for efficient transduction of non-cycling CD34+ cells, which express scarcely CAR and $\alpha_v$-integrins. To test this, the transduction properties of Ad5GFP and Ad5GFP/F35 vectors were analyzed on CD34+ cells, K562, and HeLa cells. FIG. 21 shows the percentage of transduced, GFP expressing cells depending on the MOI used for infection. Nearly 100% of HeLa cells were transduced with Ad5GFP and Ad5GFP/F35 at MOIs of >/=25. More than 95% of the K562 cells were transduced with Ad5GFP/F35 at MOIs of >/=100, whereas the transduction rate was significantly lower with Ad5 where it increased with the MOI reaching a plateau at ~70% GFP-positive cells after infection with an MOI of 400. Transduction of CD34+ cells was about three fold more efficient with Ad5GFP/F35 than with Ad5GFP at all MOIs analyzed. Interestingly, at higher MOIs, the transduction rate did not rise proportionally with the viral dose and soon reached a plateau indicating that in both cases only specific subset/s of CD34+ cells were permissive to infection. In order to characterize in more detail these specific, permissive subset/s, additional transduction studies were performed. First, the percentage of GFP expressing cells was determined in CD34+fractions that were stained for $\alpha_v$-integrins or CARs (FIG. 22). The low number of CAR positive CD34+ cells complicated accurate co-labeling studies, and there was no correlation between CAR expression and the proportion of transduced cells among CD34+ cells infected with Ad5GFP or Ad5GFP/F35. Interestingly, for Ad5GFP, 65% of all GFP expressing cells were positive for $\alpha_v$-integrins, whereas less than 22% of GFP positive cells infected with the chimeric virus stained positive for $\alpha_v$-integrin expression. While only 17% of the whole CD34+population expressed GFP after Ad5GFP infection, the percentage of GFP-expressing cells in the CD34+/□$_v$-integrins positive fraction was 50%. This indicates that Ad5GFP vector-mediated GFP expression was preferentially localized to $\alpha_v$-integrin positive CD34+subsets, whereas after infection with the Ad5GFP/F35 vector, GFP was expressed in a broader spectrum of CD34+ cells with most of them being $\alpha_v$-integrin-negative.

Next, transduced cells were simultaneously analyzed for GFP as well as for CD34 and CD117 markers. As mentioned before, only about 90% of all cells used in our analysis were positive for CD34 at the time of infection, hence the multiparameter analysis for CD34 and GFP. A population of CD34+ cells is extraordinarily heterogeneous in morphology and stem cell capacity. The subpopulation of CD34+ and CD 117+ cells resembles very primitive hematopoietic cells (Ikuta, K, Weissman, I. L. 1992 Proc. Natl. Acad. Sci. USA. 89:1502–1506; Simmons, P. J, et al. 1994. Expl. Hematology. 22.157–165). FIG. 23 summarizes the analyses of GFP expression in correlation with these specific stem cell markers. While 54% of cells infected with chimeric vector were positive for GFP and CD34+, only 25% of cells infected with Ad5GFP expressed the transgene and CD34+ marker (FIG. 23A, lower panel). More importantly, based on GFP expression, the chimeric virus transduced 80% of c-kit positive cells, whereas the Ad5-based vector transduced only 36% (FIG. 23A, middle panel). In an additional experiment, CD34+ cells were sorted for CD117 expression prior to infection with Ad5GFP or Ad5GFP/F35 and, 24 hours post-infection, GFP expression was analyzed in this specific fraction (FIG. 23B). This analysis revealed that the chimeric vectors transduced 4 fold more CD34+/CD117+ than the Ad5GFP vector.

In conclusion, these results demonstrated that the chimeric Ad5GFP/F35 vector was clearly superior to the Ad5GFP vector in targeting and transduction of CD34+ cells. Furthermore, the data suggest that the spectrum of CD34+ cell subsets permissive for Ad infection was significantly different for the chimeric vector than for the Ad5 vector.

Figure 24A:
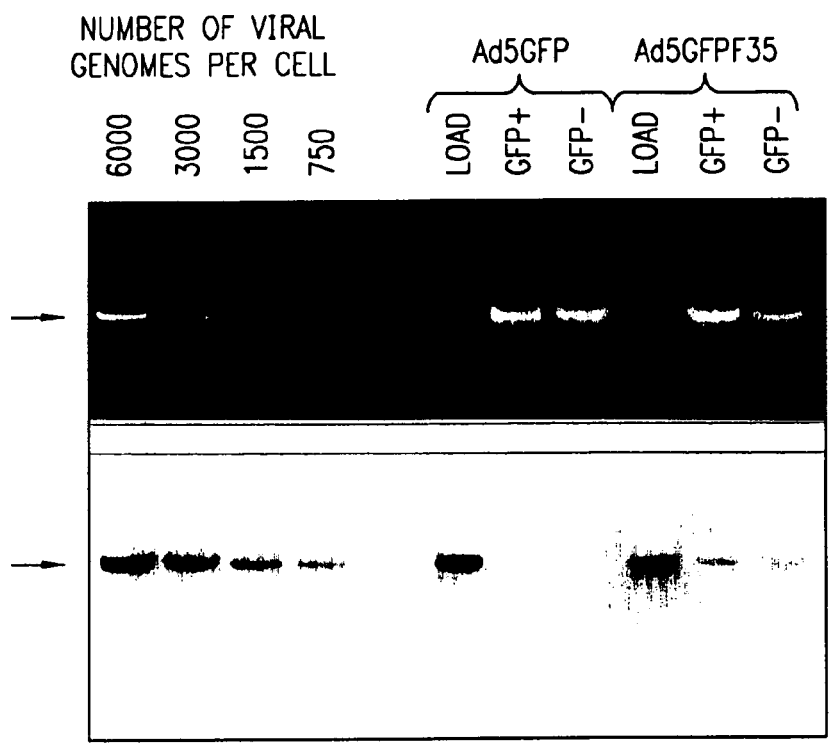

Analysis of Viral Genomes within CD34+ Cells Infected with the Ad5 and Chimeric Vectors:

So far, the transduction rate of CD34+ cells was measured based on GFP expression after infection with Ad5GFP and Ad5GFP/F35. Considering the extraordinary heterogeneity of CD34+ cells in morphological and functional parameters, GFP may not be expressed in all cell types that were efficiently infected. Reasons for this include that the CMV promoter may not be active in all cell types or that the regulation of transgene expression could differ between subsets on a post-transcriptional or post-translational level. To test this, we quantified the number of intracellular (transduced) viral genomes within GFP positive and GFP negative fractions of CD34+ cells infected with Ad5GFP and Ad5GFP/F35. To do this, twenty-four hours after infection, CD34+ cells were sorted for GFP positive and GFP negative fractions, which were subsequently used to isolate genomic DNA together with transduced viral DNA. The number of viral genomes was determined by quantitative Southern blot as described for FIG. 15. Per GFP-positive CD34+ cell, about 270 copies of the Ad5GFP/F35 viral genome were detected. Interestingly, a remarkable 200 copies of the Ad5GFP/F35 viral genome were found per GFP-negative CD34+ cell (FIGS. 24A and 25). This demonstrated that not all infected cells expressed GFP and implies that the actual transduction rate was higher than 54% (GFP-positive cells). We concluded that the CMV promoter was not active in all transduced CD34+ subsets. No Ad5GFP vector specific signal was detected within infected CD34+ (GFP positive or negative) fractions by Southern blot which had a detection limit of 14 viral genomes per cell. From this, we can conclude that the vector DNA concentration per transduced cell was at least 20 times higher for Ad5GFP/F35 than for Ad5GFP.

Figure 24B:
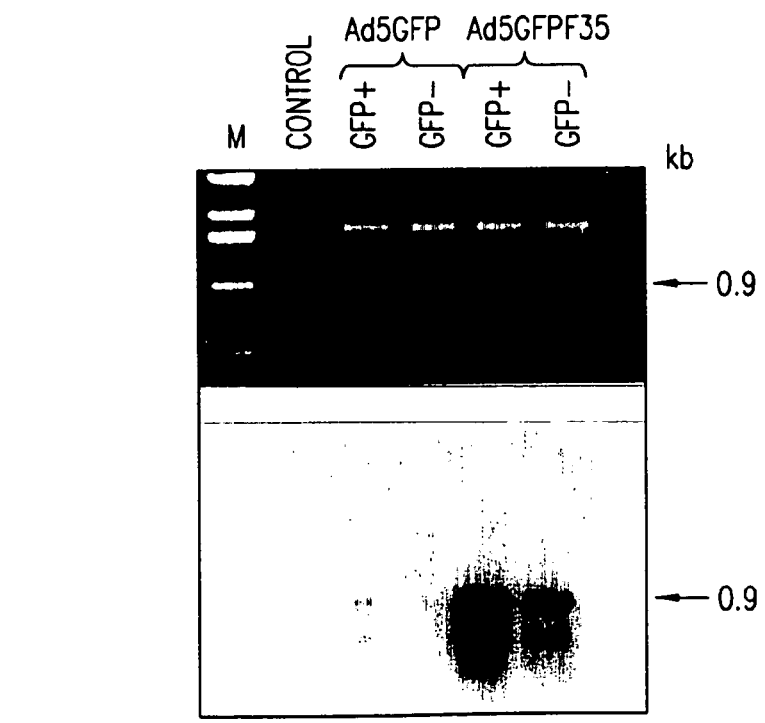

Ad5GFP DNA was only detectable in DNA samples from infected CD34+ cells by Southern blot after prior PCR amplification with vector specific primers (FIGS. 24B and 25). This indicates that the replication deficient Ad5 vector is present but at a very low copy number, which may be limited by intracellular genome stability. Using the PCR-Southern detection method, Ad5 vector DNA was also detected in GFP negative cells, supporting that the CMV promoter may not have been the optimal choice for transduction studies. It is notable that studies by others on viral genome analyses after infection of CD34+ cells with Ad5 vectors were performed only after prior PCR amplification (Mitani, K., et al. 1994. *Human Gene Therapy.* 5:941–948; Neering, S. J., et al. 1996. *Blood.* 88:1147–1155).

Discussion

The chimeric Ad5GFP/F35 vector has binding and internalization properties similar to Ad35. Therefore, the fiber substitution was sufficient to swap cell tropism from Ad5 to Ad35. The Ad5GFP/F35 capsid chimera contained the short-shafted Ad35 fiber incorporated into an Ad5 capsid, instead of the naturally occurring long-shafted Ad5 fiber. During Ad5 infection, interaction between the penton base and intergrins is required to induce viral internalization. For this interaction, the length of fiber shaft and the precise spatial arrangement of knob and RGD motifs are critical for the virus entry strategy. The natural spatial arrangement is disturbed when short-shafted heterologous fibers are inserted into the Ad5 capsid. Interestingly, the Ad5/35 capsid chimera allows for efficient infection, suggesting that the protruding RGD motives in the Ad5 penton base do not affect the interaction with the primary Ad35 receptor. So far, most of the chimeric viruses were generated by substituting only the Ad5 knob while maintaining the long Ad5 fiber shaft (Chillon, M., et al. 1999. *J. Virology.* 73:2537–2540; Krasnykh, V. N., et al. 1996. *J. Virology.* 70:6839–6846; Stevenson, S. C., et al. 1995. *J. Virology.* 69:2850–2857; Stevenson, S. C., et al. 1997. *J. Virology.* 71:4782–4790). The exception was an Ad5/7 chimeric virus (Gall, J., et al. 1996. *J. Virology.* 70:2116–2123), where the whole Ad5 fiber was substituted by the short-shafted Ad7 fiber. However, similar to the parental Ad5, the Ad5/7 chimera still required $\alpha_v$-integrins for infection.

This Ad5GFP/F35 chimera is the first demonstration that despite the presence of RGD motifs within the Ad5 penton, the chimeric virus uses cell entry pathways determined primarily by the receptor specificity of the short-shafted heterologous fiber. This does not exclude that interaction with a secondary receptor may increase binding affinity. The latter is supported by the observation that Ad35 and Ad5GFP/F35 slightly differed in their ability to compete with Ad5 or Ad3 for binding. It is possible that Ad5/35 attachment involves, in addition to the high affinity fiber binding, interaction between Ad5 capsid proteins (e.g. RGD motifs) and secondary receptor/s that overlap with those used by Ad3 and Ad5.

This data indicate that infection with Ad5-based vectors is restricted to a specific subset of CD34+ cells. The percentage of GFP expressing cells after Ad5GFP infection of CD34+ cells reached a plateau at MOIs higher than 100 indicating that only a limited fraction of CD34+ cells was permissive to Ad5. Also, strong replication of wild type Ad5 in infected CD34+ cells may be the result of preferential transduction of a specific subpopulation of CD34+ resulting in a expression of early viral genes at a level sufficient to initiate viral replication. The presence of a specific subpopulation of CD34+ cells permissive to Ad5-vector infection was suggested by others (Byk, T., et al. 1998. *Human Gene Therapy.* 9:2493–2502; Neering, S. J., et al. 1996. *Blood.* 88:1147–1155). In the present report, we further characterized this subpopulation and demonstrated that Ad5-based vectors preferentially infected $\alpha_v$-integrin positive CD34+ cells. Integrins (including $\alpha_v$) are thought to be important for homing and trafficking of transplanted hematopoietic cells, however little is known about the correlation between $\alpha_v$-integrin expression and the differentiation status of hematopoietic cells (Papayannopoulou, T., Craddock, C. 1997. *Acta Haematol.* 97:97–104; Roy, V., Verfaillie, C. M. 1999. *Exp. Hematol.* 27:302–312). There was no clear correlation between CAR and GFP expression suggesting that Ad5GFP may be able to use another membrane protein as a primary receptor. Alternatively, Ad5GFP transduction observed at an MOI of 200–400 could be the result of direct interaction between virus and $\alpha_v$-integrins triggering internalization, which may be the preferred pathway in the absence of CAR (Legrand, V., et al. 1999. *J. Virology.* 73:907–919). Importantly, infection with the chimeric Ad5GFP/F35 vector was not restricted to the $\alpha_v$-positive CD34+ subpopulation.

Among CD34+ cells, the subpopulation of CD34+ and CD117+ cells resembles very primitive hematopoietic cells (Ikuta, K., Weissman, I. L. 1992 *Proc. Natl. Acad. Sci. USA.* 89:1502–1506; Simmons, P. J., et al. 1994. *Expl. Hematology.* 22:157–165). The receptor for stem cell factor, CD117 (c-kit) belongs to a tyrosine kinase family. It was previously shown that c-kit+, CD34+ cord blood cells contain a high fraction (16%) of hematopoietic progenitors (Neu, S., et al. 1996. *Leukemia Research.* 20:960–971). Early in ontogeny 34+/CD117+ cells have long-term repopulating activity (Sanchez, M. J., et al. 1996. *Immunity.* 5:513–525). An average of 50–60% of CD34+ cells are reported to be CD117 positive (Ikuta, K., Weissman, I. L. 1992 *Proc. Natl. Acad. Sci. USA.* 89:1502–1506; Neu, S., et al. 1996. *Leukemia Research.* 20:960–971; Simmons, P. J., et al. 1994. *Expl. Hematology.* 22:157–165). In our studies, the chimeric vector expressed GFP in 54% CD34+ cells and 80% of CD34+/c-kit+ cells. The actual viral transduction rate could be even higher because transduced Ad5GFP/F35 vector DNA was also found in GFP-negative fractions of infected cells. This indicates that the CMV promoter used to drive GFP expression in our vectors was not active in all transduced cells. We selected the CMV promoter for transgene expression based on published data demonstrating that PGK and CMV promoters allowed for efficient transgene expression in CD34 cells whereas the HTLV-I and RSV promoter were almost inactive (Byk, T., et al. 1998. *Human Gene Therapy.* 9:2493–2502; Case, S. S., et al. 1999. *Proc. Natl. Acad. Sci. USA.* 96:2988–2993). On the other hand, studies by Watanabe et al. (Watanabe, T., et al. 1996. *Blood.* 87:5032–5039) suggest that the CMV promoter is not active or rapidly silenced in certain CD34+subsets. Our data underscore this observation. Considering retroviral transduction studies, the retroviral MLV promoter may have been a better candidate for transduction studies in hematopoietic cells (Bregni, M., et al. 1998. *Gene Therapy.* 5:465–472).

After having demonstrated that the Ad5GFP/F35 vector efficiently transduced cells carrying stem cell specific markers, the next logical step would be to perform colony assays with pre-sorted GFP positive/negative cells. However, this assay is complicated by the fact that infection with first generation Ad vectors is cytotoxic and affects the formation and growth of progenitor colonies in MC-cultures (Mitani, K., et al. 1994. *Human Gene Therapy.* 5:941–948; Watanabe, T., et al. 1996. *Blood.* 87:5032–5039). This side effect is caused by the expression of Ad proteins within transduced cells (Lieber, A., C.-Y. et al. 1996. *Journal of Virology.* 70:8944–8960; Schiedner, G., et al. 1998. *Nature Genetics.* 18:180–183; Yang, Y., et al. 1994. *Proc. Natl. Acad. Sci. USA.* 91:4407–4411). Some of these proteins (e.g E4-orf4, pTP, or E3-11.6k) have pro-apoptotic activity (Langer, S. J., Schaak, J. 1996. *Virology.* 221:172–179; Lieber, A., et al. 1998. *J. Virology.* 72:9267–9277; Shtrichman, R., Kleinberger, T. 1998. *J. Virology.* 72:2975–2983; Tollefson, A. E., A et al. 1996 *J. Virology.* 70:2296–2306). Clearly, this would affect the outcome of transduction studies with Ad5GFP/F35, which allows for the efficient transfer of viral genomes into CD34+ cells implying significant expression of viral proteins. Moreover, recently published data indicate that short-term colony assay mostly measure mature progenitors and do not represent a rigorous test for transduction of potential stem cells.

A definitive demonstration that Ad5GFP/F35 based vectors can transduce HSC requires colony assays or preferably, repopulation assays in SCID-NOD mice. We can perform these studies with gutless vectors (Steinwaerder, D. S., et al. 1999. *J. Virol* 73:9303–13) and integrating □Ad.AAV vectors devoid of all viral genes (Lieber, A., et al. 1999. *J Virol* 73:9314–24) generated based on Ad5GFP/F35 chimeric capsids. Alternatively, gutless, retargeted vectors could be used to transiently express a retroviral receptor on CD34+ cells to increase their susceptibility to infection with retroviral vectors based on an approach that we have published earlier (Lieber, A., et al., 1995. *Human Gene Therapy.* 6:5–11).

Our finding that Ad5GFP/F35 can efficiently transduce hematopoietic cells with potential stem cell capacity represents an important step towards stable gene transfer into HSCs and gene therapy of blood disorders. Furthermore, the virological aspects of this invention contribute to a better understanding of adenovirus cell interactions.

I: Retargeting of Ad5 Based Vectors with Modified Fibers Carrying Specific Ligand Peptides for HSC and Other Cell Types Another alternative to make Ad5-capsid-based vectors suitable for HSC gene therapy is to incorporate the coding sequence for HSC specific peptides into the H1 loop region of the Ad5 fiber gene. The modification of the H1-loop was successfully exercised by Krasnykh et al. with a 7 amino-acid long FLAG peptide (DYDDDDK) (SEQ ID NO.: 11). Using phage display peptide libraries (Pascqualini, R. et al., 1996, *Nature*, 380:364–66), Renata Pasqualini (La Jolla Cancer Research Center) reported recently, at the First Meeting of the American Society for Gene Therapy, the identification of small peptide ligands specific for bone marrow cells. The corresponding sequences encoding these peptides can be added to modify the H1 loop sequence employing site-directed mutagenesis. Optimally, the ligands should allow for the efficient internalization of adenoviral particles based on a CAR- and integrin independent pathway. Modified adenoviral vectors containing the AAVBG cassette can be produced and tested for HSC tropism as described above.

Adenovirus Peptide Display:

If order to retarget adenoviruses to any cell type of interest, a strategy is provided which involves creating a library of adenoviruses displaying random peptides in their fiber knobs as ligands and screening this library for adenovirus variants with tropism to a particular cell type in vitro and potentially in vivo.

The development of the adenovirus peptide display technique is based on the following ideas. (i) Although the tertiary structure of the Ad5 fiber knob is known, it remains unclear which domains are involved in receptor binding. There are data suggesting that receptor-binding domains partially overlap with hemagglutination domains, which are well characterized for a number of serotypes. Therefore, three intramolecular loop regions representing potential receptor binding sites can be substituted by random peptide libraries. Eight amino acid residues in the center of the FG, or GH loops can be substituted by octameric random peptides (FIGS. 26 and 27). These substitutions will replace CAR tropism and allow for infection of refractory cell types. (ii) To synthesize the oligonucleotides encoding the peptide library a novel technique to assemble pre-synthesized trinucleotides representing the codons for all 20 amino acids is employed. This avoids termination codons and assures optimal codon usage and translation in human cells. Synthesis of a completely randomized library is possible with all 20 amino acids being incorporated with the same probability and a partially randomized library with only three (in average) random amino acids substitutions per octamer at random positions with a random amino acid to maintain certain critical features of the tertiary knob structure while introducing variability. The last model is based on the distribution of amino acids present in the hypervariable CDR 1 or 2 region of immunoglobulins. (iii) To maintain a representative library size of about $10^{10}$ different octamers per modified loop, a new cloning strategy is employed to allow for insertion of the library into the wild-type Ad5 genome without introducing additional amino acids at the substitution site and without transformation into bacteria. This strategy is based on a "seamless" cloning technique available from Stratagen. (iv) In order to produce the library of viruses, viral genomic DNA containing the modified fiber sequences is transfected into 293 cells without reduction of the library size. This critical step is done by conjugating the viral library DNA to carrier Ad5-based adenovirus via poly-lysine to assure 100% transfection efficiency. This technique allows for coupling of ~1 µg of plasmid DNA (or ~$1 \times 10^{10}$ adenoviral genomes) to $10^{10}$ viral particles which can be used to infect 293/cre cells at an MOI of 10–100. Importantly, the carrier adenoviral genome has the packaging signal flanked by lox sites preventing the packaging of carrier viral DNA after infection of 293 cells that express cre recombinase (293/cre). This helper virus system is routinely used to produce so-called gutless adenoviruses. Therefore, the virus progeny represents library genomes packaged into capsids containing preferentially Ad5 fibers. This is important for the next infection step into 293 cells at a MOI of 1 to assure a homogeneous fiber population on the capsid where the fibers are encoded by the packaged genome.

J. Production of Adenovirus Vectors with Increased Tropism to Hepatocytes

An example of a G-H loop substitution to target Ad5 to hepacytes was successful. Preliminary tests demonstrated that two evolutionarily conserved regions within the malaria circumsporozoite surface protein (CS) termed RI and RII+ mediate specific interaction with hepatocytes but not with other organs (including spleen, lung, heart and brain), nor with Kupffer cells, liver endothelial cells or with other regions of the hepatocyte membrane (Cerami, C. et al., 1992, Cell, 70:1021–33; Shakibaei, M. and U. Frevert, 1996, J. Exp. Med., 184:1699–711). These regions are conserved among different species including Plasmodium berghei, P. cynomogli, and P. falciparum that infect mouse, monkey and human hepatocytes, respectively (Cerami, C. et al., 1992, Cell, 70:1021–33; Chattejee, S. et al., 1995, Infect Immun., 63:4375–81). Peptides derived from RI (KLKQPG) (SEQ ID NO.: 12) or RII (EWSPCSVTCGNGIQVRIK) (SEQ ID NO.: 13) blocked CS binding to hepatocytes and infection by sporozoites in vivo ((Cerami, C. et al., 1992, Cell, 70:1021–33; Chatterjee, S. et al., 1995, Infect Immun., 63:4375–81). R1 and R11+peptides were separately inserted into Ad5-fiber knob (H-I and G-H loop) containing mutation with abolished binding to CAR and alpha-v integrins (Kirby, L. et al., 2000, J. Virol., 74:2804–13; Wickham, T. J. et al., 1995, *Gene Ther.,* 2:750–6). Based on preliminary data, a short-shafted fiber was used so that the virus entry strategy predominantly depends on the interaction with the primary (hepatocyte-specific receptor). The hepatocyte-specific ligands are flanked by short glycine stretches to provide flexibility and embedded into a loop formed by two cystines. This is one of the classical strategies to incorporate ligands into a protein scaffold (Doi, N. and H. Yanagawa, 1998, *Cell Mol. Life Sci.,* 54:394–404; Koivunen, E. et al., 1995, *Biotechnology* (NY), 13:265–70) and to guarantee their presentation at the protein surface. The biodistribution of the best variants is tested in vivo in C57B1/6 mice based on Southern blots or PCR for vector DNA in different organs. This mouse strain in known to be susceptible to infection with *P. berghei* (Chatterjee, S. et al., 1995, *Infect Immun.,* 63:4375–81).

K. Production of Adenovirus Vectors with Increased Tropism to Tumor Cells

A similar strategy is to insert two peptides obtained after selection for tumor tropism by displaying random peptides on filamentous phages. The first double cyclic peptide (RGD-4) proved to bind specifically to integrins present on tumor vasculature (Ellerby H. M. et al., 1999, *Nat. Med.,* 5:1032–8). The second peptide targets specific matrix metalloproteinases associated with metastatic tumor cells as shown for the breast cancer cell line MDA-MB-435 (Koivunen, E. et al., 1999, *Nat. Biotechnol.,* 17:768–74). Tropism-modified vectors are tested in animal models with hepatic metastases derived from MDA-MB-435 cells (FIG. 28).

L. Development of a Peptide Display Technique Based on Adenoviruses

A synthetic peptide library is described that allows adenovirus vectors to express random peptides in the G-H loop of the fiber knob domain. The technique of a phage display library is optimized to generate a library of adenoviruses displaying random peptides in their fiber knob. This library of adenovirus variants is then screened for tropism to a particular cell type in vitro and potentially in vivo. The oligonucleotides encoding the peptide library employ a novel technique to assemble pre-synthesized trinucleotides representing the codons for all 20 amino acids. This will end the termination codons and assure optimal codon usage and translation in human cells. To maintain a representative library size, a new "seamless" cloning strategy that allows for insertion of the library into the wild-type Ad5 genome without introducing additional amino acids at the substitution site and without transformation into bacteria. Transfection into 293 cells is done by conjugating the viral library DNA to carrier Ad5-based adenovirus via polylysine to assure a 100% transfection efficiency. Importantly, the carrier adenoviral genome has its packaging signal flanked by lox sites preventing the packaging of carrier viral DNA after infection of 293 cells that express Cre recombinase (293/cre). The library is produced with E1-positive viruses depleted for CAR and integrin tropism. Only variant that have successfully infected the cell type of interest will replicate, resulting in de novo produced virus. The sequence of the peptide ligand that conferred the particular tropism will then be analyzed in do novo produced virus.

EXAMPLE III

Combination Novel Adenoviral Vector and Modified Fiber Protein

This example describes the following studies which combine the technology of the integrating adenovirus vector that is devoid of all adenoviral genes with the modified fiber protein that retargets the vector to quiescent HSC.

A. Transduction Studies with Re-Targeted Vectors in HSC:

In order to transduce quiescent HSC and integrate into chromosomal DNA, retargeted $\Delta\text{Ad.AAV}^{fx}$ vectors are tested for reporter gene expression, and vector integration simultaneously while analyzing their clonogenic capacity. The modified $\Delta\text{Ad.AAV}^{fx}$ hybrid vectors contain genomes devoid of all adenoviral genes (a "gutless" adenovirus vector) packaged into Ad5 capsids with modified fibers. Rep may be incorporated into these $\Delta\text{Ad.AAV}^{fx}$ vectors to allow for site-specific integration into AAVS1.

Transduction Studies:

Purified human CD34+ cells in IMDM/FCS+IL-3 and SCF are infected with different doses of $\Delta\text{Ad.AAV}^{fx}$-BG (1–$10^7$ genomes per cell). CD34+ cells infected with $\Delta\text{Ad.AAV}^{fx}$-βGal are cultured for 2 days in suspension and sort β-Gal+ cells by FACS using FDG as substrate. This determines the infection efficiency. β-gal expressing cells are then submitted to clonogenic assays in semi-solid cultures (in two dishes per MOI) in the presence of multiple cytokines. (IL-3, SCF, Epo, G-CSF, GM-CSF, IL-7, Tpo). A first set of semi-solid cultures can be evaluated after 7 days; another set can be analyzed after 14 days. Colonies that have formed in semisolid culture can be characterized by light microscopy and subsequently stained with X-Gal staining. Most of the vector genomes should remain episomal and can be lost with successive cell divisions. Thus, while most cells can be X-Gal positive at day 2 or day 7 after infection, most of the larger colonies (analyzed at day 14 p.i.) may not stain homogeneously for β-Gal. A representative number of X-Gal positive and X-Gal negative colonies can be picked and analyzed for episomal and integrated vector DNA. The outcome depends on the MOI used for infection and the integration status of the vector. These studies determine whether hybrid vectors can infect primitive progenitors.

Detailed Characterization of Hybrid Vector Integration:

CD34+ cells can be infected with $\Delta\text{Ad.AAV}^{fx}$-SNori (MOI 1–$10^7$) and subjected to G418 selection in methyl cellulose (MC) cultures in the presence of growth factors (IL-3 and SCF). The resulting colonies are a mixture of mainly myeloid cells. The number and morphology of G418 resistant colonies can be determined after 2 weeks of selection. This strategy may be disadvantageous in that the appropriate stem cell may not divide and form G418 resistant colonies under the specific culture condition used. Moreover, it may be difficult to perform G418 selection on a population of heterogenous cells, which vary in their sensitivity to G418. Therefore, another set of $\Delta\text{Ad.AAV}^{fx}$-SNori infected CD34+ cells can be cultured in methylcellulose (+IL-3, SCF) without G418 selection. After 2–3 weeks, single colonies can be picked from both (w/ and w/o G418) MC cultures, morphologically characterized, and analyzed for integrated vector using the modified protocol developed for integration studies in a small number of cells (see FIG. 8). This strategy allows the assessment of whether hybrid vectors integrate into the genome of CD34+ cells cultured in the presence of growth factors. This study gives us an idea about potential position effects affecting neo or βgal expression from integrated vector copies and about the structure of the integrated vector and the flanking chromosomal regions.

An Alternative Method to Confirm Vector Integration:

Fluorescence in situ hybridization (FISH) analysis, can be performed in individual cells from MC colonies. CD34+ cells are cultured in MC in the presence of growth factors to induce cell division and subsequently treated with colchicine. Metaphase chromosome spreads are analyzed with biotin-ATP labeled probe specific for the βGal or SNori gene and a dioxigenin-UTP labeled probe for the human X-chromosome as an internal control (provided by Christine Disteche, University of Washington). Specific hybridization can be visualized with corresponding anti-biotin or anti-DIG antibodies labeled with different fluorochromes (e.g. FITC and Texas Red). Hybrid vector DNA may integrate as concatemers, which would facilitate detection by FISH. This technique allows one to localize the chromosomal integration sites of hybrid vectors.

Test Transduction into Quiescent Bone Marrow Subpopulations:

Hybrid vectors described so far can be tested to see whether quiescent CD34+ cells can be stably transduced. To avoid significant cell proliferation, purified CD34+ cells are cultured in serum free IMDM supplemented with thrombopoietin (Tpo). Tpo can alone support the survival of stem cells without stimulating their active cell proliferation (Matsunaga, T. et al., 1998, *Blood*, 92:452–61; Papayannopoulou, T. et al., 1996, *Experimental Hematology*, 24:660–69). To analyze the proliferation status of CD34+ cells at the time point of infection with the hybrid vector $\Delta\text{Ad.AAV}^{fx}$BG, BrdU is added 2 hours before infection to the culture medium. One set of cells are maintained as suspension culture in IDAM containing Tpo only for two days. Another set of cells are grown in IDAM+Tpo supplemented with multiple cytokines. Forty eight hours after infection, CD34+ cells can be FACS sorted for beta Gal expression using FDG. FDG positive cells can be further analyzed for cellular DNA replication based on BrdU incorporation and for specific CD34+subset markers. To do this, cytospins from FDG+ cells can be submitted to immunofluorescence with BrdU specific antibodies and with antibodies to specific cell surface markers (e.g. CD38, CD41). Alternatively, consecutive paraffin sections of the same cell can be analyzed for (a) transgene expression by X-Gal staining, (b) DNA synthesis based on BrdU incorporation, and (c) specific surface markers. This allows one to confirm that the culture conditions with Tpo alone prevent significant genomic DNA replication and subsequent cell proliferation as well as to determine whether quiescent CD34+ cells can be infected based on beta Gal expression in cells where BrdU labeling is absent.

Test Hybrid Vectors Integration into Quiescent CD34+ Cells:

Two sets of CD34+ cells are infected. The first set of □Ad.AAV$^{fx}$SNori infected cells are cultured for 5–7 days in the presence of cytokines; the other set is cultured without cytokines. To maintain CD34+ cell viability without cytokines during this period, the cells are cultured in the presence of Tpo or underlaid with a stromal cell line (AFT024) (Moore, K. et al., 1997, *Blood,* 89:4337–47), which can maintain HSC viable for 4 to 7 weeks. After this specific time period, both sets are submitted to clonogenic assays (in the presence of multiple cytokines) either in combination with G418 selection or without selection. Single colonies are analyzed morphologically and submitted to genomic DNA analysis (FIG. 8) to determine the vector integration status. The ultimate proof for stem cell transduction is the in vivo survival/expansion assay. To do this, the CD34+ cells expressing beta Gal are used for transplantation experiments, If the number of FDG+ cells is not sufficient, total ΔAd.AAV$^{fx}$BG infected cells as well as all ΔAd.AAV$^{fx}$-SNori infected cells can be used directly without selection. Transplantation can be performed via tail vein injection into sublethally irradiated SCID NOD mice (Dao, M. A., et al., 1998, *Blood,* 4, 1243–1255; Matsunaga, T. et al., 1998, *Blood,* 92:452–61). At different time points after transplantation (4 to 8 weeks), mice can be sacrificed to obtain bone marrow cells which then can be cultured in suspension until various assays are performed for X-Gal and cell markers as described earlier. These cells also can be submitted to a secondary colony assay in MC or secondary transplantation into SCID NOD mice. Furthermore, MC colonies derived from these cells can be analyzed for the presence of integrated vector DNA by the method illustrated in FIG. 8. The expression and integration data together allow conclusions about the repopulation efficiency and about potential position effects.

B. Optimization of ΔAd.AAV$^{fx}$ Vectors for γ r-globin Expression in Hematopoietic Stem Cells:

One specific example of the invention is (a) to construct retargeted hybrid vector with the γ-globin as the transgene under the control of erythroid cell specific promoter, (b) to analyze the level and kinetics of γ-globin expression after transduction with hybrid vectors in in vitro and in vivo assays, (c) if required, to protect gene expression from position effects using γ-globin LCRs or insulators incorporated into hybrid vectors, and (d) to study whether γ-globin introns or heterologous introns can increase γ-globin expression.

Another central issue of the invention is to demonstrate that hybrid vectors can accommodate larger transgenes than rAAV and retroviruses. The insert size limitation of these vectors is 5 kb. Transgene cassettes up to 8 kb can be inserted into hybrid vectors as described. The maximal insert size may be about 14 kb, if hybrid vectors are produced on the basis of E2a and/or E4 deleted rAd vectors in corresponding packaging cell lines. The maximal insert size in hybrid vectors is dictated by the packaging limit of first generation vectors (Ad.AAV) (<36 kb) which are necessary intermediates for hybrid virus production at large scale. It is expected that stability and titer of Ad.AAV vectors with an 8 kb globin gene cassette is comparable to the vector containing the 2.5–3.5 kb cassette used in Ad.AAVBG, Ad.AAV1, and Ad.AAVSNori. The following example experiments address these issues.

Production of ΔAd.AAV$^{fx}$ with Large Globin Expression Cassettes:

In order to improve the condition of sickle cell disease, the expression level of the transferred γ-lobin gene must be at least 50% of that of each endogenous βgene. These levels of transgene expression can only be achieved by using optimal expression cassettes, including extended LCRs and intron containing gamma genes. (Forrester, W. C., et al., 1986, *Proc. Natl. Acad. Sci. USA* 83, 1359–1363; Fraser, P., et al., 1998, *Curr. Opinion in Cell Bio.,* 10, 361–365; Grosveld, F., et a.l, 1998, *Seminars in Hematology,* 35, 105–111; Martin, D. et al., 1996, *Current Opinion in Genetics and Development,* 6:488–95), So far, most of the γ-globin expression cassettes are designed for retroviral and rAAV vectors, thus, less than 5 kb and have to be devoid of internal splice sites or poly adenylation signals. With integrating vectors described herein, it is possible to go beyond this size limitation. This allows one to improve γ-globin expression in bone marrow cells in terms of an adequate expression level and long term persistence. For this purpose, γ-globin constructs developed by Li et al (Emery, D. W., et al. 1999 *Hum Gene Ther* 10:877–88; Li, Q., et al. 1999. *Blood* 93:2208–16) or by Ellis et al (Ellis, J., et al., 1996, *EMBO J.,* 15, 562–568; Ellis, J., et al., 1997, *Nucleic Acids Res.* 25, 1296–1302) is chosen.

(i) The first cassette contains a γ-globin expression unit used in retroviral vectors. This allows for a direct comparison between the two systems. This construct includes the beta promoter from –127 to the beta initiation codon, which is connected in frame with the gamma coding region. This beta promoter is combined with the 300 bp HS40 derived from the human alpha globin locus, which acts as a strong enhancer for globin expression. The globin gene is the 1.1 kb version with intron 1 and partially deleted intron 2. A second cassette is generated containing the HS40 beta promoter and gamma globin gene with the complete 3.3 kb gamma globin gene.

(ii) The second construct contains the 6.5 kb beta μLCR, which confer a dominant chromatin opening activity and an adequate level of gamma globin expression in transgenic mice. The LCR is linked to the short 1.1 kb version of the gamma globin gene or the complete 3.3 kb gamma gene.

(iii) Additional globin expression cassette can be generated which include insulators, MARs or SARs, as well as other elements that can improve transgene expression from integrated vectors or in transgenic animals, like introns derived from the HPRT or hGH genes (Chung, J. H., et al., 1997, *Proc. Natl. Acad. Sci. USA* 94, 575–580; Dunaway, M., et al, 1993, *Mol. Cell. Biol.,* 17, 182–189; Felsenfeld, G., et al., 1996, *Proc. Natl. Acad. Sci. USA* 93, 93840–9388; Klehr, D., et al., 1991, *Biochemistry,* 30, 1264–1270).

Transduction Studies with ΔAd.AAVfx-globin Vectors:

Transduction studies with globin-hybrid vectors are performed as described earlier (Steinwaerder, D. S., et al. 1999. *J Virol* 73:9303–13). Transduced CD34+ cells are submitted to differentiation in colony assays or analyzed in vivo expansion assays in SCID-NOD mice. MC-colonies or bone marrow cells from experimental mice are analyzed for globin expression. Gamma-globin expression is measured using fluorescent anti-gamma-globin antibodies. RNAase protection studies can be performed to specifically quantitate gamma globin mRNA in comparison with -globin RNA. For these studies around $10^4$–$10^5$ cells are needed per test.

Position Effects:

In the absence of the LCR, globin genes are subjected to strong position effects when they are transferred into cultured CD34+ cells or erythroleukemic lines (Fraser, P., et al., 1998, *Curr. Opinion in Cell Bio.,* 10, 361–365; Grosveld, F., et a.l, 1998, *Seminars in Hematology,* 35, 105–111). Another concern is that site-specific integration of ΔAd.AAV/rep vectors into AAVS1 may silence transgene expression. If silencing happens, it can be overcome by incorporating LCRs such as the 6.5 kb □ globin μLCR (Ellis, J., et al., 1996, *EMBO J.*, 15, 562–568; Grosveld, F., et a.l, 1998, *Seminars in Hematology*, 35, 105–111) or insulators into ☐Ad.AAV based expression units. Insulators are DNA elements that protect an integrated reporter gene from chromosomal position effects or that block enhancer activated transcription from a downward promoter. Insulator elements are known for *Drosophila melanogaster* genes (Gypsy, suppressor of Hairy wing, scs, scs', Fab-7), for the chicken beta-globin gene (HS4) and for the T cell receptor (BEAD1; 14, 21.25). Specifically, the *Drosophila* gypsy or the beta globin insulator can be inserted as two copies flanking the globin expression cassette into hybrid vectors. The position effects can be examined in transduced MC-colonies based on the analysis of integrated vector DNA (see FIG. 29) and gamma-globin mRNA quantification. Analogous studies can be performed on transduced human bone marrow cells obtained after transplantation of infected CD34+ cells into SCID-NOD mice.

Intron Effects on Gamma-Globin Expression:

A number of reports reveal that the deletion of globin introns, particularly the second intron of the beta and gamma genes, decrease globin mRNA stability and thus the expression level (Antoniou, M. et al., 1998, *Nucleic Acid Res.*, 26:721–9). RNA viruses such as onco-retro, lenti- and foami viruses are problematic as vehicles for intron-containing transgenes. Because ΔAd.AAV is a DNA virus, it should package globin introns and LCRs if necessary without the decreased titers and rearrangements observed with retroviral vectors.

APPENDIX I

Human and Animal Adenoviruses Available from American Type Culture Collection

1: Adenovirus Type 21 ATCC VR-1099
2: SA18 (Simian adenovirus 18) ATCC VR-943
3: SA17 (Simian adenovirus 17) ATCC VR-942
4: Adenovirus Type 47 ATCC VR-1309
5: Adenovirus Type 44 ATCC VR-1306
6: Avian adenovirus Type 4 ATCC VR-829
7: Avian adenovirus Type 5 ATCC VR-830
8: Avian adenovirus Type 7 ATCC VR-832
9: Avian adenovirus Type 8 ATCC VR-833
10: Avian adenovirus Type 9 ATCC VR-834
11: Avian adenovirus Type 10 ATCC VR-835
12: Avian adenovirus Type 2 ATCC VR-827
13: Adenovirus Type 45 ATCC VR-1307
14: Adenovirus Type 38 ATCC VR-988
15: Adenovirus Type 46 ATCC VR-1308
16: Simian adenovirus ATCC VR-541
17: SA7 (Simian adenovirus 16) ATCC VR-941
18: Frog adenovirus (FAV-1) ATCC VR-896
19: Adenovirus type 48 (candidate) ATCC VR-1406
20: Adenovirus Type 42 ATCC VR-1304
21: Adenovirus type 49 (candidate) ATCC VR-1407
22: Adenovirus Type 43 ATCC VR-1305
23: Avian adenovirus Type 6 ATCC VR-831
24: Avian adenovirus Type 3 (Inclusion body hepatitis virus)
25: Bovine adenovirus Type 3 ATCC VR-639
26: Bovine adenovirus Type 6 ATCC VR-642
27: Canine adenovirus ATCC VR-800
28: Bovine adenovirus Type 5 ATCC VR-641
29: Adenovirus Type 36 ATCC VR-913
30: Ovine adenovirus type 5 ATCC VR-1343
31: Adenovirus Type 29 ATCC VR-272
32: Swine adenovirus ATCC VR-359
33: Bovine adenovirus Type 4 ATCC VR-640
34: Bovine adenovirus Type 8 ATCC VR-769
35: Bovine adenovirus Type 7 ATCC VR-768
36: Adeno-associated virus Type 2 (AAV-2H) ATCC VR-680
37: Adenovirus Type 4 ATCC VR-4
38: Adeno-associated virus Type 3 (AAV-3H) ATCC VR-681
39: Peromyscus adenovirus ATCC VR-528
40: Adenovirus Type 15 ATCC VR-661
41: Adenovirus Type 20 ATCC VR-662
42: Chimpanzee adenovirus ATCC VR-593
43: Adenovirus Type 31 ATCC VR-357
44: Adenovirus Type 25 ATCC VR-223
45: Chimpanzee adenovirus ATCC VR-592
46: Chimpanzee adenovirus ATCC VR-591
47: Adenovirus Type 26 ATCC VR-224
48: Adenovirus Type 19 ATCC VR-254
49: Adenovirus Type 23 ATCC VR-258
50: Adenovirus Type 28 ATCC VR-226
51: Adenovirus Type 6 ATCC VR-6
52: Adenovirus Type 2 Antiserum: ATCC VR-1079
53: Adenovirus Type 6 ATCC VR-1083
54: Ovine adenovirus type 6 ATCC VR-1340
55: Adenovirus Type 3 ATCC VR-847
56: Adenovirus Type 7 ATCC VR-7
57: Adenovirus Type 39 ATCC VR-932
58: Adenovirus Type 3 ATCC VR-3
59: Bovine adenovirus Type 1 ATCC VR-313
60: Adenovirus Type 14 ATCC VR-15
61: Adenovirus Type 1 ATCC VR-1078
62: Adenovirus Type 21 ATCC VR-256
63: Adenovirus Type 18 ATCC VR-1095
64: Baboon adenovirus ATCC VR-275
65: Adenovirus Type 10 ATCC VR-11
66: Adenovirus Type 33 ATCC VR-626
67: Adenovirus Type 34 ATCC VR-716
68: Adenovirus Type 15 ATCC VR-16
69: Adenovirus Type 22 ATCC VR-257
70: Adenovirus Type 24 ATCC VR-259
71: Adenovirus Type 17 ATCC VR-1094
72: Adenovirus Type 4 ATCC VR-1081
73: Adenovirus Type 16 ATCC VR-17
74: Adenovirus Type 17 ATCC VR-18
75: Adenovirus Type 16 ATCC VR-1093
76: Bovine adenovirus Type 20 ATCC VR-314
77: SV-30 ATCC VR-203
78: Adenovirus Type 32 ATCC VR-625
79: Adenovirus Type 20 ATCC VR-255
80: Adenovirus Type 13 ATCC VR-14
81: Adenovirus Type 14 ATCC VR-1091
82: Adenovirus Type 18 ATCC VR-19
83: SV-39 ATCC VR-353
84: Adenovirus Type 11 ATCC VR-849
85: Duck adenovirus (Egg drop syndrome) ATCC VR-921
86: Adenovirus Type 1 ATCC VR-1
87: Chimpanzee adenovirus ATCC VR-594
88: Adenovirus Type 15 ATCC VR-1092
89: Adenovirus Type 13 ATCC VR-1090
90: Adenovirus Type 8 ATCC VR-1368
91: SV-31 ATCC VR-204
92: Adenovirus Type 9 ATCC VR-1086
93: Mouse adenovirus ATCC VR-550
94: Adenovirus Type 9 ATCC VR-10
95: Adenovirus Type 41 ATCC VR-930
96: CL ATCC VR-20

97: Adenovirus Type 40 ATCC VR-931
98: Adenovirus Type 37 ATCC VR-929
99: Marble spleen disease virus (Hemorrhagic enteritis virus)
100: Adenovirus Type 35 ATCC VR-718
101: SV-32 (M3) ATCC VR-205
102: Adenovirus Type 28 ATCC VR-1106
103: Adenovirus Type 10 ATCC VR-1087
104: Adenovirus Type 20 ATCC VR-1097
105: Adenovirus Type 21 ATCC VR-1098
106: Adenovirus Type 25 ATCC VR-1103
107: Adenovirus Type 26 ATCC VR-1104
108: Adenovirus Type 31 ATCC VR-1109
109: Adenovirus Type 19 ATCC VR-1096
110: SV-36 ATCC VR-208
111: SV-38 ATCC VR-355
112: SV-25 (M8) ATCC VR-201
113: SV-15 (M4) ATCC VR-197
114: Adenovirus Type 22 ATCC VR-1100
115: SV-23 (M2) ATCC VR-200
116: Adenovirus Type 11 ATCC VR-12
117: Adenovirus Type 24 ATCC VR-1102
118: Avian adenovirus Type 1 (Chicken-Embryo Lethal Orphan)
119: SV-11 (M5) ATCC VR-196
120: Adenovirus Type 5 ATCC VR-5
121: Adenovirus Type 23 ATCC VR-1101
122: SV-27 (M9) ATCC VR-202
123: Avian adenovirus Type 2 (GAL) ATCC VR-280
124: SV-1 (M1) ATCC VR-195
125: SV-17 (M6) ATCC VR-198
126: Adenovirus Type 29 ATCC VR-1107
127: Adenovirus Type 2 ATCC VR-846
128: SV-34 ATCC VR-207
129: SV-20 (M7) ATCC VR-199
130: SV-37 ATCC VR-209
131: SV-33 (MIO) ATCC VR-206
132: Avian adeno-associated virus ATCC VR-865
133: Adeno-associated (satellite) virus Type 4 ATCC VR-646
134: Adenovirus Type 30 ATCC VR-273
135: Adeno-associated (satellite) virus Type 1 ATCC VR-645
136: Infectious canine Hepatitis (Rubarth's disease)
137: Adenovirus Type 27 ATCC VR-1105
138: Adenovirus Type 12 ATCC VR-863
139: Adeno-associated virus Type 2 (molecularly cloned)
140: Adenovirus Type 7a ATCC VR-848

---

What is claimed is:

1. A recombinant, double-stranded, adenovirus vector, wherein the vector comprises:
   a. an adenovirus left inverted terminal repeat sequence;
   b. an adenovirus packaging sequence;
   c. a first adenoviral-associated inverted terminal repeat sequence;
   d. a first inverted repeat sequence;
   e. a heterologous promoter sequence which mediates transcription in a direction towards the adenoviral left inverted terminal repeat sequence in part a;
   f. a foreign gene sequence;
   g. a second inverted repeat sequence;
   h. a second adenoviral-associated inverted terminal repeat sequence;
   i. a gene sequence that mediates replication of an adenovirus in a transduced cell; and
   j. an adenovirus right inverted terminal repeat sequence;
   wherein the adenovirus packaging sequence is located on the one strand of the double-stranded vector; and wherein the other of the two strands of the double-stranded vector comprises a nucleotide sequence encoding a modified adenoviral fiber protein which alters the tropism of the adenovirus vector, and wherein the modified adenoviral fiber protein is a modified fiber knob, a modified fiber tail or a modified fiber shaft.

2. A recombinant, double-stranded, adenovirus vector wherein the vector comprises:
   a. an adenovirus left inverted terminal repeat sequence;
   b. an adenovirus packaging sequence;
   c. a first adenoviral-associated inverted terminal repeat sequence;
   d. a first inverted repeat sequence;
   e. a heterologous promoter sequence which mediates transcription in a direction away from the adenoviral left inverted terminal repeat sequence in part a;
   f. a foreign gene sequence;
   g. a second inverted repeat sequence;
   h. a second adenoviral-associated inverted terminal repeat sequence;
   i. a gene sequence that mediates replication of an adenovirus in a transduced cell; and
   j. an adenovirus right inverted terminal repeat sequence;
   wherein the adenovirus packaging sequence is located on one strand of the double-stranded vector of the vector; and wherein the other of the two strands of the double-stranded vector comprises a nucleotide sequence encoding a modified adenoviral fiber protein which alters the tropism of the adenovirus vector, and wherein the modified adenoviral fiber protein is a modified fiber knob, a modified fiber tail or a modified fiber shaft.

3. The adenoviral vector of claim 1 or 2, wherein the modified fiber knob, the modified fiber tail or the modified fiber shaft is from an adenoviral serotype that differs from the serotype of the left or right adenoviral inverted terminal repeat sequence.

4. The adenoviral vector of claim 1 or 2, wherein the modified fiber knob, the modified fiber tail or the modified fiber shaft is from adenoviral serotypes Ad3, Ad7, Ad9, Ad11 or Ad35.

5. The adenoviral vector of claim 1 or 2, wherein the modified fiber knob binds a cell surface protein on a target cell of interest.

6. The adenoviral vector of claim 1 or 2, wherein the modified fiber knob is modified in the G-H loop region or H-I loop region.

7. The adenoviral vector of claim 1 or 2, wherein the modified fiber knob comprises a heterologous peptide ligand which replaces the G-H loop region or H-I loop region.

8. The adenoviral vector of claim 7, wherein the heterologous peptide ligand is an RI or RII protein from malaria circumsporozoite surface protein (CS).

9. The adenoviral vector of claim 8, wherein the RI protein from malaria circumsporozoite surface protein (CS) comprises the amino acid sequence KLKQPG (SEQ ID NO.:12).

10. The adenoviral vector of claim 8, wherein the RII protein from malaria circumsporozoite surface protein (CS) comprises the amino acid sequence EWSPCSVTCGNGIQVRIK (SEQ ID NO.:13).

11. The adenoviral vector of claim 7, wherein the heterologous peptide ligand comprises the amino acid sequence:
   a. LGGKPDQ (SEQ ID NO.:15);
   b. LNGCGSC (SEQ ID NO.:16);
   c. LNGCGSGC (SEQ ID NO.:17); or
   d. LNGCGXXXXXXXXXXGC (SEQ ID NO.:18).

12. The adenoviral vector of claim 1 or 2 which infects hepatocytes, bone marrow cells, stem cells or breast cancer cells.

13. The adenoviral vector of claim 1 or 2, wherein the modified fiber shaft has a shortened length.

14. The adenoviral vector of claim 1 or 2, wherein the adenoviral packaging sequence and the left and right adenoviral inverted terminal repeat sequences are from the same adenoviral serotype.

15. The adenoviral vector of claim 1 or 2, wherein the adenoviral packaging sequence and the left and right adenoviral inverted repeat sequences are from serotype Ad5.

16. The adenoviral vector of claim 1 or 2, wherein the foreign gene sequence encodes a therapeutic gene product, a selectable gene product, or a reporter gene product.

17. The adenoviral vector of claim 1 or 2, wherein the therapeutic gene product is gamma globin or human alpha-1 antitrypsin.

18. The adenoviral vector of claim 1 or 2, wherein the selectable gene product is neomycin, ampicillin, penicillin, tetracycline or gentamycin.

19. The adenoviral vector of claim 1 or 2, wherein the reporter gene product is green fluorescent protein, beta galactosidase or alkaline phosphatase.

20. The adenoviral vector of claim 1 or 2, further comprising an insulator element sequence.

21. The adenoviral vector of claim 1 or 2, further comprising a bacterial origin of replication.

22. The adenoviral vector of claim 1 or 2, further comprising a nucleotide sequence encoding a rep78 protein.

23. The adenoviral vector of claim 1 or 2, wherein the gene sequence that mediates replication of an adenovirus in the transduced cell is selected from a group consisting of E2 and E4; E1, E2 and E4; and E2, E3 and E4.

24. The adenoviral vector of claim 1 or 2, wherein the foreign gene sequence comprises a 5' portion of the foreign gene sequence.

25. The adenoviral vector of claim 1 or 2, wherein the foreign gene sequence comprises a 3' portion of the foreign gene sequence.

* * * * *